United States Patent
Acton et al.

(10) Patent No.: US 6,632,830 B1
(45) Date of Patent: Oct. 14, 2003

(54) ACE-2 INHIBITING COMPOUNDS AND METHODS OF USE THEREOF

(75) Inventors: Susan L. Acton, Lexington, MA (US); Timothy D. Ocain, Framingham, MA (US); Alexandra E. Gould, Cambridge, MA (US); Natalie A. Dales, Arlington, MA (US); Bing Guan, Brighton, MA (US); James A. Brown, Framingham, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/561,759

(22) Filed: Apr. 28, 2000

Related U.S. Application Data

(60) Provisional application No. 60/171,052, filed on Dec. 16, 1999, and provisional application No. 60/132,034, filed on Apr. 30, 1999.

(51) Int. Cl.[7] .................. A61K 31/194; A61K 31/198; A61K 31/4172; C07C 229/16; C07D 231/12
(52) U.S. Cl. ............... 514/365; 514/400; 514/406; 514/561; 514/567; 548/204; 548/339.1; 548/339.5; 548/375.1; 562/443; 562/445; 562/568
(58) Field of Search ................ 514/400, 561, 514/567, 365, 406; 548/339.1, 204, 339.5, 375.1; 562/443, 445, 568

(56) References Cited

U.S. PATENT DOCUMENTS

| | | | | |
|---|---|---|---|---|
| 4,591,648 A | * | 5/1986 | Jones et al. ............... 548/334 |
| 5,110,799 A | * | 5/1992 | Tolman et al. ............. 514/19 |
| 5,338,649 A | * | 8/1994 | Inaba et al. ............... 430/430 |
| 5,481,018 A | * | 1/1996 | Athey et al. .............. 558/442 |
| 5,665,371 A | * | 9/1997 | Hoermann ................ 424/423 |
| 5,827,820 A | * | 10/1998 | du Moulin et al. ........ 514/2 |
| 6,194,556 B1 | * | 2/2001 | Acton et al. .............. 536/23.2 |
| 6,201,021 B1 | * | 3/2001 | Ohuchida et al. .......... 514/558 |

FOREIGN PATENT DOCUMENTS

DE 3219113 * 11/1983

OTHER PUBLICATIONS

Roberts et al. Basic Principles of Organic Chemistry, 2nd ed. Menlo Park: W.A. Benjamin, Inc. pp. 1208–1210, 1977.*

* cited by examiner

*Primary Examiner*—Jeffrey E. Russel
(74) *Attorney, Agent, or Firm*—Fish & Richardson PC

(57) ABSTRACT

ACE-2 inhibiting compounds are disclosed. These compounds include compounds of formula (IV):

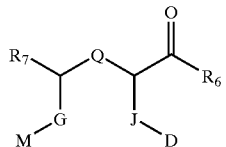

wherein the variables are as described in the specification. Pharmaceutical compositions containing the compounds are also discussed. The pharmaceutical compositions may contain an effective amount of a compound of the invention to treat ACE-2 associated disorders such as a blood pressure related disease or disorder, cell proliferation disorder, kidney disorder, kinetensin associated disorder, inflammation associated disorder, or an allergic disorder.

145 Claims, 5 Drawing Sheets

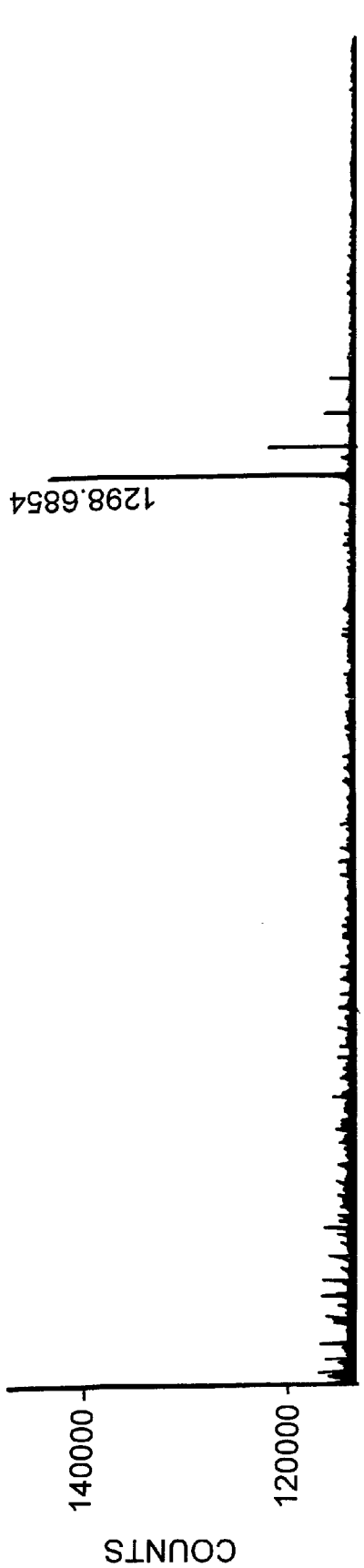
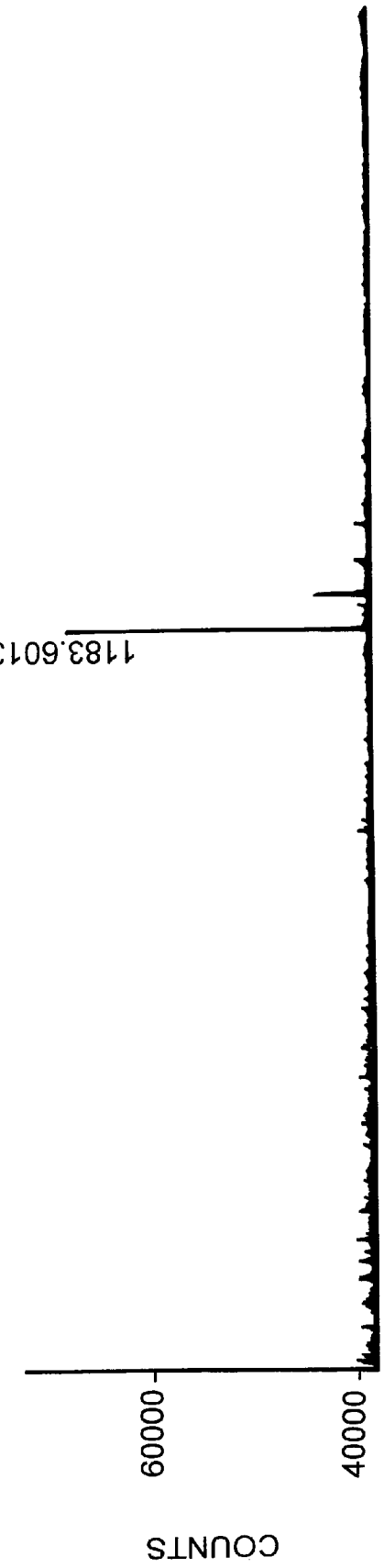
FIG. 1A
FIG. 1B

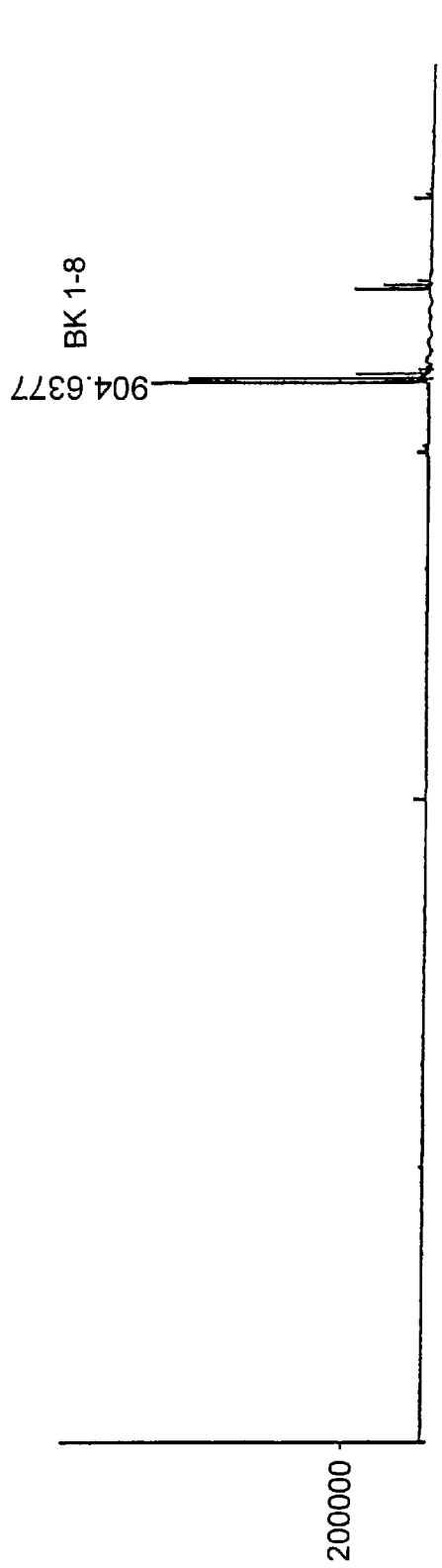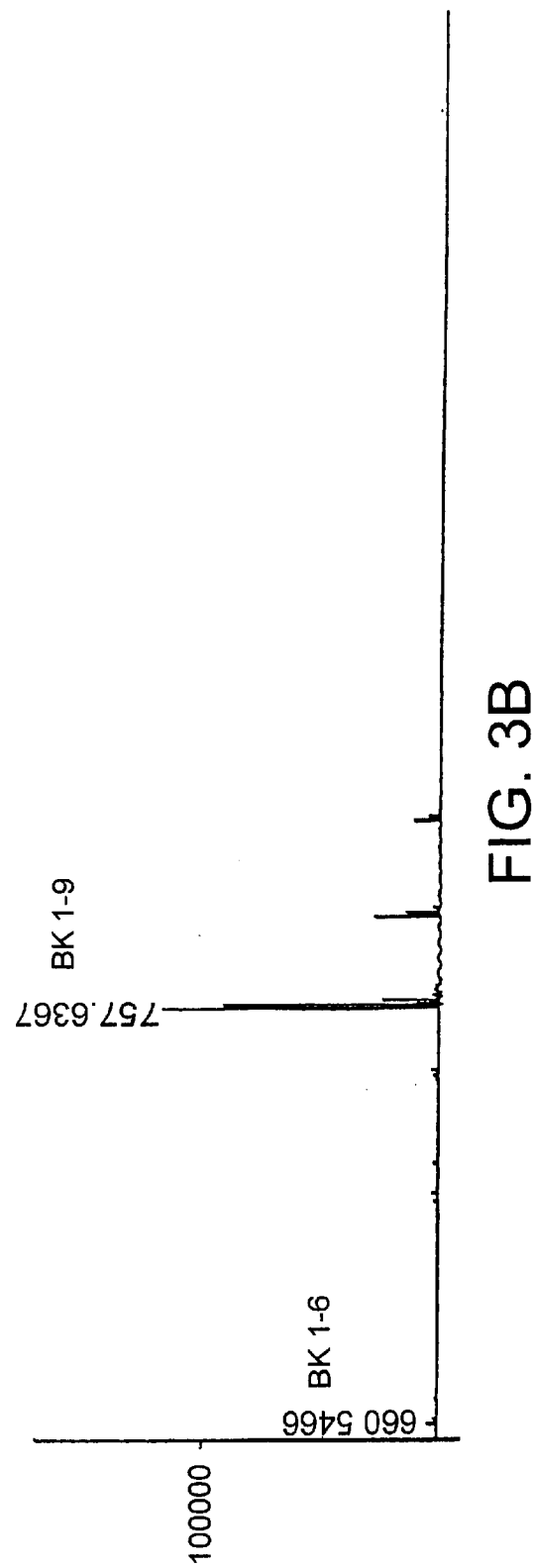

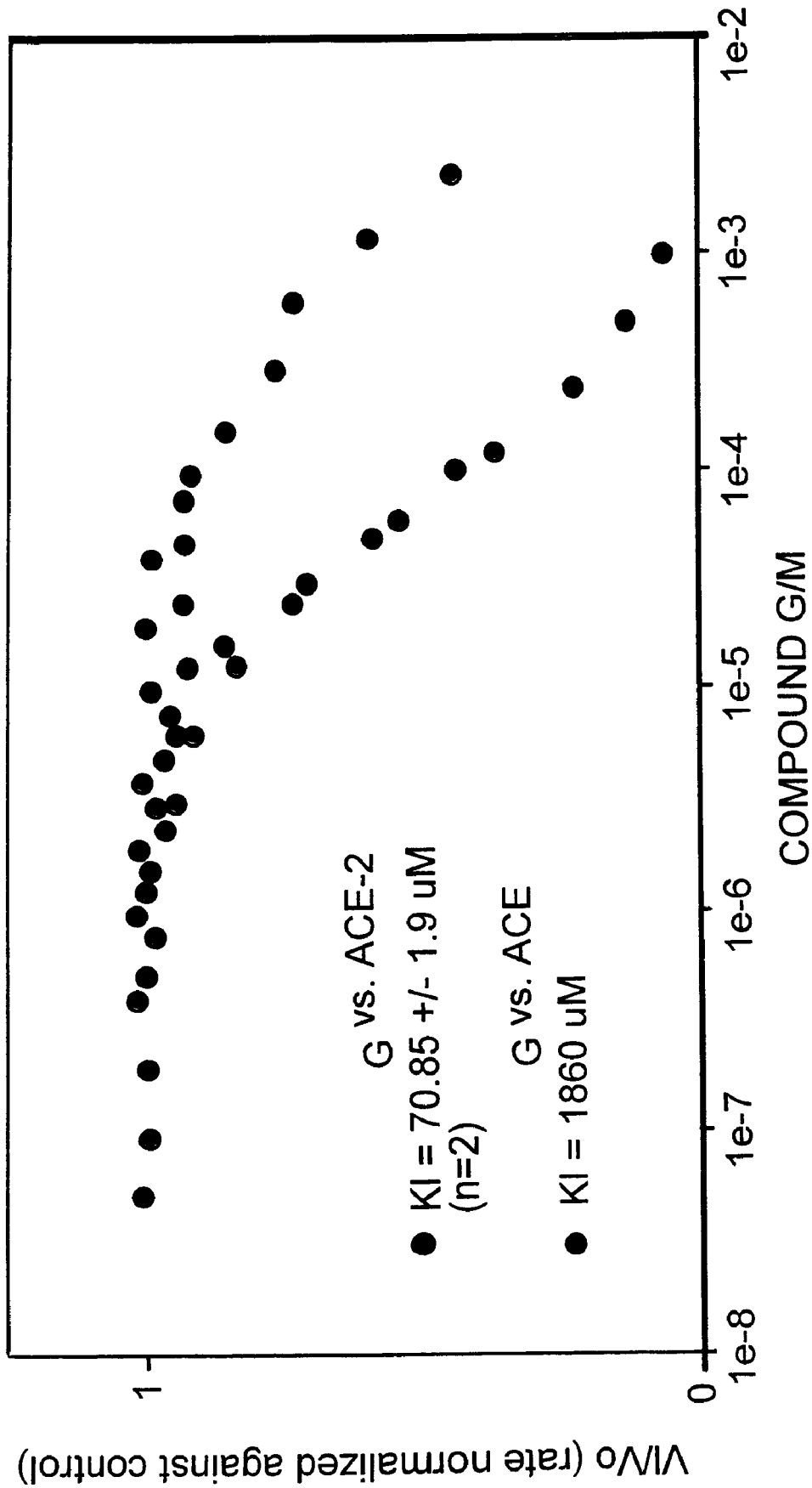

```
                              SEQUENCE LISTING

<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 7
<223> OTHER INFORMATION: Xaa = Lysine tagged with anti-dinitrophenol

<400> SEQUENCE: 1

Tyr Val Ala Asp Ala Pro Xaa
 1               5
```

ACE-2 INHIBITING COMPOUNDS AND METHODS OF USE THEREOF

RELATED APPLICATIONS

This application claims priority to U.S. Provisional Application Ser. No. 60/171,052, entitled "ACE-2 Inhibiting Compounds and Methods of Use Thereof," filed on Dec. 16, 1999 and U.S. Provisional Application Ser. No. 60/132,034, entitled "ACE-2 Inhibiting Compounds and Methods of Use Thereof," filed on Apr. 30, 1999. The entire contents of both of the aforementioned applications are hereby expressly incorporated herein by reference.

BACKGROUND OF THE INVENTION

Hypertension, or high blood pressure, is the most common disease affecting the heart and blood vessels. Statistics indicate that hypertension occurs in more than 50 million Americans. The prevalence of hypertension increases with age. Between 85 and 90% of cases are primary (i.e., essential) hypertension, i.e., a persistently elevated blood pressure that cannot be attributed to any particular organic cause. The remaining percentage of cases are secondary hypertension, i.e., elevated blood pressure having an identifiable underlying cause such as kidney disease and adrenal hypersecretion.

Hypertension is of considerable concern because of the harm it can do to the heart, brain, and kidneys if it remains uncontrolled. The heart is most commonly affected by high blood pressure. When blood pressure is high, the heart uses more energy in pumping against the increased resistance caused by the elevated arterial blood pressure. Because of the increased effort, the heart muscle thickens and the heart becomes enlarged and needs more oxygen. If it cannot meet the demands put on it, angina pectoris or even myocardial infarction may develop. Hypertension can result in numerous complications including left ventricular failure; atherosclerotic heart disease; retinal hemorrhage, exudates, papilledema, and vascular accidents; cerebrovascular insufficiency with or without stroke; and renal failure. An untreated hypertensive patient is at great risk of developing disabling or fatal left ventricular failure, myocardial infarction, cerebral hemorrhage or infarction, or renal failure at an early age. Hypertension is the most important risk factor predisposing to stroke and is an important risk factor predisposing to coronary atherosclerosis.

An abnormal blood pressure can also result from specific conditions or diseases, such as heart failure. Heart failure is a chronic or acute state that results when the heart is not capable of providing sufficient cardiac output to satisfy the metabolic needs of the body. Heart failure is commonly referred to as congestive heart failure (CHF), since symptoms of increased venous pressure (pulmonary congestion with left heart failure and peripheral edema with right heart failure) are often predominant. Symptoms and signs of CHF include fatigue, peripheral and pulmonary edema, and visceral congestion (e.g., dyspnea). These symptoms are produced by diminished blood flow to the various tissues of the body and by accumulation of excess blood in the various organs, that results from the heart being incapable of pumping out the blood. Heart failure can result from several underlying diseases, most commonly in industrialized nations from atherosclerotic coronary artery disease with myocardial infarction. Myocardidis, various cardiomyopathies, and valvular and congenital defects may also result in heart failure (Anderoli et al., Cecil: Essentials of Medicine, Third Edition, WB Saunders Company, 1993).

A major problem in CHF is the inability of the failing left ventricle to maintain a normal blood pressure, thus resulting in increased pre- and afterload, and leading to progressive ventricular dilation with wall remodeling. Vasodilators which induce a reduction in pre- and afterload, i.e., reduction of the systemic vascular resistance and reduction of the peripheral vascular resistance, respectively, are currently used to treat CHF (Lionel H. Opie, Drugs for the Heart, Third Edition, WB Saunders Company, 1991).

One important system involved in regulating blood pressure is the renin-angiotensin-aldosterone system. In this system, renin, a proteolytic enzyme formed in the granules of the juxtaglomerular apparatus cells catalyzes the conversion of angiotensinogen (a plasma protein) into angiotensin I, a decapeptide. This inactive product is then cleaved by a converting enzyme, termed angiotensin converting enzyme (ACE) mainly in the lung, but also in the kidney and brain, to an octapeptide, angiotensin II, which is a potent vasoconstrictor and also stimulates the release of aldosterone. Aldosterone is an adrenal cortex hormone that promotes the retention of salt and water by the kidneys and thus increases plasma volume, resulting in an increase in blood pressure. Angiotensin II also stimulates the release of norepinephrine from neural cells which interacts with specific receptors on blood vessels, thereby resulting in an increase in calcium and vasocontriction. Another mechanism by which angiotensin II induces vasoconstriction is by interacting with specific receptors on blood vessels, thereby resulting in an opening of calcium channels and an increase in calcium, resulting in vasoconstriction.

ACE, also referred to as peptidyl dipeptidase A (EC 3.4.15.1) and kininase II is a metallopeptidase, more particularly a zinc peptidase which hydrolyses angiotensin I and other biologically active polypeptides, such as kinins, e.g., bradykinin. Bradykinin is a vasodilator, which acts at least in part by inducing release of vasodilator prostaglandins, and which is inactivated upon hydrolysis by ACE. Thus, ACE increases blood pressure at least in part by producing angiotensin II, a vasoconstrictor; and by inactivating bradykinin, a vasodilator. Bradykinin is also involved in other biological activities including mediation of pain and inflammatory reactions.

The role of ACE in regulating blood pressure is further demonstrated at least by the efficacy of ACE inhibitors in reducing hypertension and treating CHF in individuals. ACE inhibitors have major roles as vasodilators in hypertension and CHF and are among the most efficient drugs for treating these disorders (see, e.g., Opie et al., Angiotensin Converting Enzyme Inhibitors and Conventional Vasodilators, in Lionel H. Opie, Drugs for the Heart, Third Edition, WB Saunders Company, 1991, p106). Several clinical trials indicate that ACE inhibitors prolong survival in a broad spectrum of patients with myocardial infarction and heart failure, ranging from those who are asymptomatic with ventricular dysfunction to those who have symptomatic heart failure but are normotensive and hemodynamically stable. For example, one study demonstrated a 40% reduction in mortality at 6 months in patients with severe heart failure (The CONSENSUS Trial Study Group, N. Engl. J. Med. 316:1429 (1987); The CONSENSUS Trial Study Group, N. Engl. J. Med. 325:293 (1991)).

Several ACE inhibitors are currently available on the market (e.g., CAPTOPRIL, ENALAPRIL, FOSINOPRIL, LINSINOPRIL, and RAMIPRIL). However, ACE inhibitors in large doses can cause a variety of undesirable secondary effects including nephrotic syndrome, membraneous glomerulonephritis, nephritis, and leukopenia, as well as angioedema. Therefore, it would be advantageous to identify alternate therapies useful for treating blood pressure disorders, (e.g., hypertension) to avoid the side effects and improve the efficacy associated with the ACE inhibitors currently available.

SUMMARY OF INVENTION

The invention pertains to, at least in part, compounds and methods for modulating the activity of ACE-2. In one embodiment, the invention features an ACE-2 inhibiting compound of the formula (I):

wherein Z is a zinc coordinating moiety, and L is an amino-acid mimicking moiety. In one embodiment, L is an amino acid mimic containing a non-polar side chain. In an advantageous embodiment, Z is a carboxylic acid or a cleavable prodrug moiety.

In another embodiment, the invention features an ACE-2 inhibiting compound of the formula (II):

wherein Z is a zinc coordinating moiety, E is an enzyme coordinating moiety, A is an auxiliary ACE-2 pocket binding moiety, and B is an ACE-2 side chain pocket binding moiety.

In another embodiment, the invention pertains to an ACE-2 inhibiting compound of the formula (III):

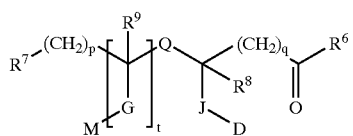

wherein $R^6$ is hydroxyl or a protecting prodrug moiety; $R^7$ is a carboxylic acid, arylaminocarboxy, aroyl, alkylaminocarboxy, aminocarboxy, alkenylaminocarboxy, aryl, a protecting prodrug moiety, hydroxyl, heterocycle, alkoxy, ether, thiol or an amine; $R^8$ is hydrogen, or alkyl, and optionally linked to D to form a cyclic structure; $R^9$ is lower alkyl or hydrogen; Q is a bond, O, S, CHOH, CHSH, $CHNH_2$, $CHNHR^3$, $CHNR^3R^4$, NH, $NR^3$, $(CH_2)_n$, $O(CH_2)_n$, $(CH_2)_nO(CH_2)_n$, wherein n is either 0, 1, 2, or 3, and $R^3$ and $R^4$ are each independently substituted or unsubstituted $C_1$–$C_5$ branched or straight chain alkyl, $C_2$–$C_5$ branched or straight chain alkenyl, substituted or unsubstituted acyl, aryl, $C_3$–$C_8$ ring, optionally substituted with up to four heteroatoms; G is a linking moiety; M is an anchor moiety; J is a bond, an alkyl, alkenyl, or alkynyl moiety; D is hydrogen, alkyl, amine, hydroxy, alkenyl, alkynyl, aryl, or heteroaryl, optionally linked to G , M or Q to form a ring; t is 0, 1, 2, or 3; p is 0, 1, 2, 3, 4, or 5; q is 0, 1, 2, or 3.

The present invention also features a method of treating an ACE-2 associated state in a patient, e.g., a human, by administering to the patient a therapeutically effective amount of an ACE-2 inhibiting compound, such that the ACE-2 associated state is treated. In a further embodiment, the patient is suffering from a blood pressure related disease or disorder, such as, preferably, congestive heart failure or hypertension.

The invention also pertains to a pharmaceutical composition comprising a pharmaceutically acceptable carrier and an effective amount of an ACE-2 inhibiting compound to treat an ACE-2 associated state.

The invention also involves a method for treating an ACE-2 associated state in a patient, by administering to the patient an effective amount of an ACE-2 inhibiting compound and an effective amount of an ACE inhibitor.

In yet another embodiment, the invention features a method for inhibiting the hydrolysis of an ACE-2 target peptide by contacting ACE-2 with an ACE-2 inhibiting compound and an ACE-2 target peptide, thereby inhibiting the hydrolysis of the ACE-2 target peptide.

As described in detail below, ACE-2 is a protein having regions of substantial homology to ACE, and having angiotensin cleaving activity. Administration of an ACE-2 modulating compound e .g., an ACE-2 inhibitor, alone or in combination with a known ACE inhibitor may be useful for treating ACE-2 associated disorders, (e.g., hypertension, congestive heart failure). By combining the compound with a known ACE inhibitor it is believed that the effective dose of the ACE inhibitor will be reduced, thus decreasing the risk for potentially harmful side effects. In addition to such combination therapies, use of ACE-2 inhibitors alone may be more efficacious and provide alternative therapies over existing ones.

BRIEF DESCRIPTION OF THE DRAWINGS

FIGS. 1A and 1B show that ACE-2 hydrolyzes Angiotensin I (1–10) (FIG. 1A) to Ang (1–9) (FIG. 1B).

FIGS. 3A and 3B show that ACE-2 catalyzes the hydrolysis of des-Arg bradykin (1–8) (FIG. 3A) to des-Arg bradykinin (1–7) (FIG. 3B).

FIG. 4 depicts a graph of the activity of ACE-2 and ACE when treated with Compound G.

DETAILED DESCRIPTION OF THE INVENTION

Figures 2A, 2B:
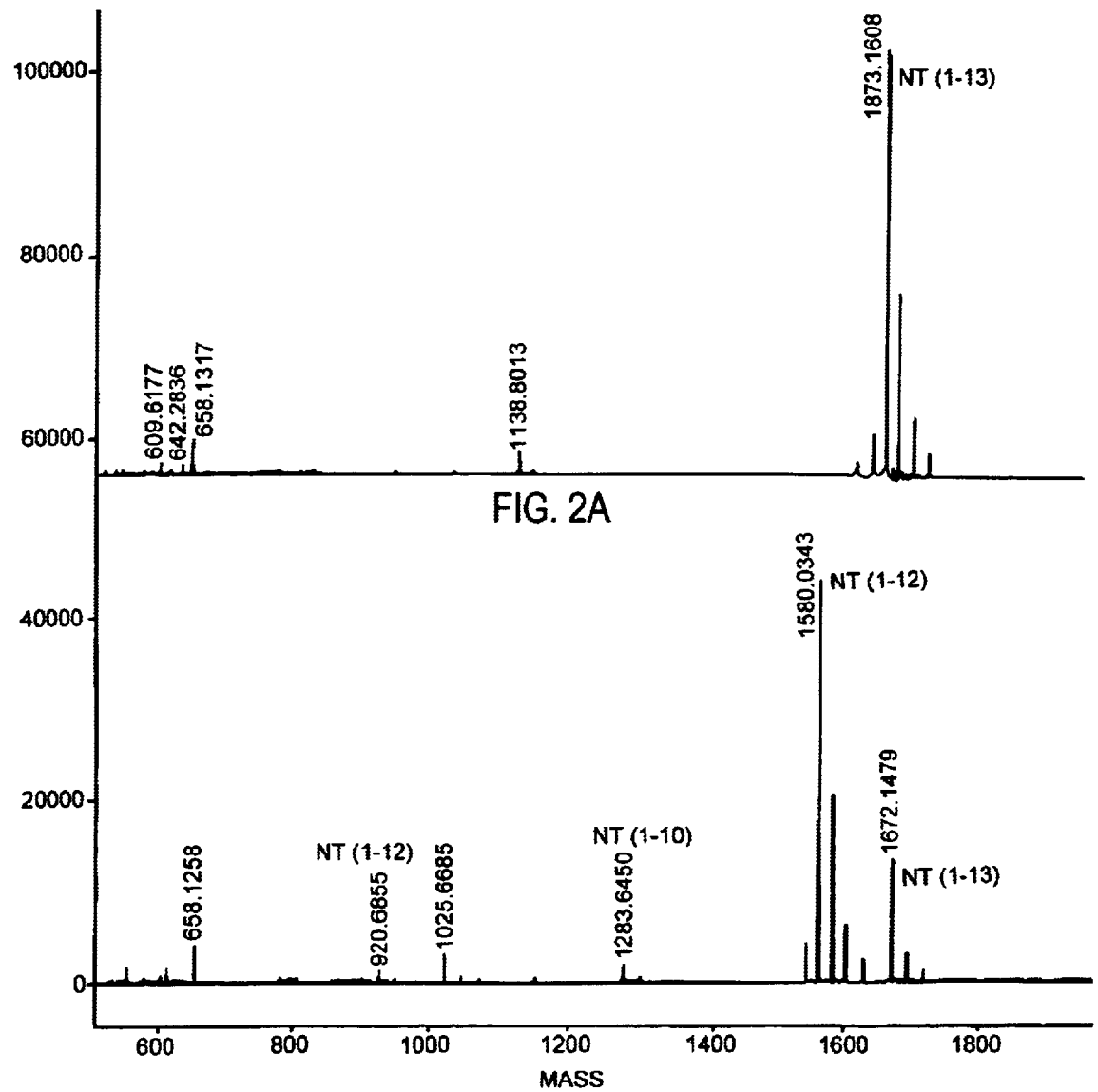
FIGS. 2A and 2B depict mass spectroscopy data for the ACE-2 catalyzed hydrolysis of Neurotensin (1–13) (FIG. 2A) to Neurotensin (1–12) (FIG. 2B).

The present invention pertains to compounds and methods which inhibit the activity of ACE-2.

ACE-2 is a protein having regions which are significantly homologous to regions of known angiotensin converting enzymes (ACEs). The sequence of the full length cDNA encoding ACE-2 was determined from a clone obtained from a cDNA library prepared from mRNA of a human heart of a subject who had congestive heart failure. The cDNA encoding the full length human ACE-2 protein and comprising 5' and 3' untranslated regions is 3396 nucleotides long (See U.S. patent application Ser. No. 09/163,648 for the complete nucleic acid and amino acid sequence). The mature ACE-2 protein has 787 amino acids and has the amino acid sequence from amino acid 19 to amino acid 805.

ACE-2 protein comprises several functional domains. It comprises a zinc binding domain (ZBD) from amino acid 374 to amino acid 378 which is referred to herein as minimum zinc binding domain. It is proposed that at least some of the adjacent amino acids participate in binding zinc. This minimum zinc binding domain has an amino acid sequence which is identical to that of the zinc binding domain that is present in all ACE proteins which have been identified as being located in the catalytic site of the enzyme (Lattion et al. *FEBS Letters* (1989) 252:99). In addition, many of the amino acids which have been reported as interacting with the zinc atom or involved in catalysis in ACE, are present in ACE-2.

ACE-2 has a hydrophobic region in its C-terminal domain from about amino acid 741 to about amino acid 765. This hydrophobic region is thought to be a transmembrane domain, similar to that present in ACE proteins. A BLAST search (Altschul et al. *J. Mol. Biol.* (1990) 215:403) of the nucleic acid and the amino acid sequences of ACE-2 revealed that certain portions of the ACE-2 protein and cDNA have a significant homology to certain regions of previously identified angiotensin converting enzymes. Two forms of ACE proteins have been described previously: a larger form, referred to as endothelial or somatic ACE, since it is present in numerous somatic tissues, including vascular endothelium, renal tubular epithelium, ciliated gut epithelium, stimulated macrophages, areas of the brain and testis. The smaller form of ACE is referred to as the testicular form, since it is found essentially only in developing sperm cells in the testis.

ACE-2 is capable of hydrolyzing angiotensin I by cleaving the C-terminal amino acid (i.e., leucine) from angiotensin I. This 9 amino acid peptide ("Ang.(1–9)") can be further hydrolyzed by ACE into a 5 amino acid peptide containing the first five amino acids from angiotensin I. ACE-2 is also known to catalyze the hydrolysis of other peptides, such as desArg Bradykinin, and thus may be involved in regulating blood pressure in a similar manner as endothelial ACE protein.

ACE-2 is characterized by the presence of a transmembrane domain in the carboxy terminal portion of the protein. Thus, ACE-2 can be in a membrane bound form. ACE proteins have also been found in a soluble form, which may result either from leakage of the protein from the surface or, from specific hydrolysis by a protease, or the soluble form may be encoded by a differentially spliced mRNA. Accordingly, ACE-2 is believed also to exist in a soluble form.

The overall similarity of ACE-2 proteins compared with ACE proteins is relatively weak. The overall percent identity and similarity between human ACE-2 and the human testicular ACE protein (which is the ACE protein with which ACE-2 has the highest overall similarity) is about 42.9% and 62% respectively. At the nucleotide level, human ACE-2 and human testicular ACE have about 50.8% identity.

The invention pertains, at least in part, to ACE-2 modulating compounds, e.g., ACE-2 inhibitors, of the formula (I):

Z—L     (I)

wherein Z is a zinc coordinating moiety and L is an amino-acid mimicking moiety.

The language "ACE-2 modulating compound" refers to compounds which modulate, e.g., inhibit, promote, or otherwise alter the activity of ACE-2. ACE-2 modulating compounds include both ACE-2 agonists and antagonists.

The language "ACE-2 inhibiting compound" includes compounds which reduce the activity of ACE-2, e.g., the ability of ACE-2 to hydrolyze substrate, in vivo or in vitro. Preferably, the ACE-2 inhibiting compounds are ACE-2 antagonists.

The language "zinc coordinating moiety" includes moieties which interact with metals, e.g., zinc, associated with ACE-2. Although not wishing to be bound by theory, it is thought that the zinc coordinating moiety interacts with at least one zinc atom which is associated with the zinc binding domain of ACE-2, as discussed above. Examples of zinc coordinating moieties include, for example, groups which are either capable of coordinating to zinc (e.g., electron donating groups, e.g., an ester, a guanidine, a carboxylic acid, hydroxyalkyl, an alkyl group, an amide, an amine, a hydroxyl, a thiol, a ketone, an aldehyde, carboxylate, sulfonate, sulfide, imidazolyl, or other heterocyclic moieties) or are capable of being converted into groups capable to coordinating to zinc, e.g., cleavable carboxylic acid prodrug moieties or other ester prodrug capable of releasing the free acid upon administration. Furthermore, in certain embodiments, the zinc-coordinating moiety may be a hydrogen atom. The language "zinc coordinating moiety" includes all moieties which coordinate to zinc or other metal atoms associated with ACE-2 and allow the compounds of the invention to perform their intended function, e.g., modulating ACE-2 activity.

The term "interact" includes any interactions which allow the compound to perform its intended function. Examples of interactions include ionic interactions, hydrophobic interactions, covalent interactions, hydrogen bond interactions, and combinations thereof.

Prodrugs are compounds which are converted in vivo to active forms (see, e.g, R. B. Silverman, 1992, "The Organic Chemistry of Drug Design and Drug Action", Academic Press, Chp. 8). Prodrugs can be used to alter the biodistribution (e.g., to allow compounds which would not typically enter the reactive site of the protease) or the pharmacokinetics for a particular compound. For example, a carboxylic acid group, can be esterified, e.g., with a methyl group or an ethyl group to yield an ester. When the ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

The language "cleavable carboxylic acid prodrug moieties" includes moieties which can be metabolized in vivo to a group capable of coordinating to zinc or another enzyme binding site. The prodrug moieties may be metabolized in vivo by esterases or by other mechanisms to carboxylic acids. Examples of prodrugs and their uses are well known in the art (See, e.g., Berge et al. (1977) "Pharmaceutical Salts", *J. Pharm. Sci.* 66:1–19). The prodrugs can be prepared in situ during the final isolation and purification of the compounds, or by separately reacting the purified compound in its free acid form with a suitable derivatizing agent. Carboxylic acids can be converted into esters via treatment with an alcohol in the presence of a catalyst. Examples of cleavable carboxylic acid prodrug moieties include substituted and unsubstituted, branched or unbranched lower alkyl ester moieties, (e.g., ethyl esters), lower alkenyl esters, di-lower alkyl-amino lower-alkyl esters (e.g., dimethylaminoethyl ester), acylamino lower alkyl esters, acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. In certain embodiments of the invention, the prodrug moiety itself may coordinate to the zinc without being converted prior to coordination.

The term "substituted" includes substituents which can be placed on the moiety and which allow the molecule to perform its intended function. Examples of substituents include alkyl, alkenyl, alkynyl, aryl, NR'R", CN, NO$_2$, F, Cl, Br, I, CF$_3$, CCl$_3$, CHF$_2$, CHCl$_2$, CONR'R", S(O)NR'R", CHO, $OCF_3$, $OCCl_3$, $SCF_3$, $SCCl_3$, COR', $CO_2R'$, and OR' wherein R' and R" are each independently hydrogen, $C_1$–$C_4$ alkyl, $C_2$–$C_4$ alkenyl, $C_2$–$C_4$ alkynyl or optionally substituted aryl. Preferably, substitutions enhance the ability of the ACE-2 modulating compound to perform its intended function, e.g., modulate ACE-2 activity.

The language "protecting prodrug moiety" includes moieties attached by a linkage, e.g., an ester linkage, to the ACE-2 modulating compound and which can be metabolized in vivo to yield an active drug. Examples of protecting prodrug moieties include amino acids (e.g., glycine, alanine), branched or unbranched, substituted or unsubstituted lower alkyls (e.g., methyl, ethyl, propyl groups), lower alkenyl groups, di-lower amino-lower alkyl groups, acylamino lower alkyl groups, acyloxy lower alkyl groups, aryl groups, aryl lower alkyl groups, and substituted aryl and aryl lower alkyl groups.

The language "amino acid mimicking moiety" includes moieties which are the same or are structurally similar to an N-linked terminal natural or unnatural amino acid (e.g., leucine, histidine) and which interact with ACE-2 resulting in inhibition or modulation of ACE-2 activity. Although not wishing to be bound by theory, it is thought that the amino acid mimicking moiety may interact with a binding pocket region of ACE-2. In one embodiment, the amino acid mimicking moiety is comprised of at least one natural or unnatural amino acid, or a derivative thereof, containing, for example, a charged, an uncharged, a polar or non-polar side chain (e.g., the side chains of alanine, valine, arginine, leucine, isoleucine, phenylalanine, tryptophan, methionine, glycine, serine, proline, threonine, cysteine, tyrosine, histidine, asparagine, glutamine, lysine, glutamic acid, and aspartic acid).

In certain embodiments, the amino acid mimicking moiety may be comprised of two or more amino acids which interact with ACE-2. These amino acid mimicking moieties may be linked by a functional group, for example, an amine group. For example, in a further embodiment, the amino acid mimicking moiety may comprise a side, chain pocket binding moiety (J—D) and an auxiliary pocket binding moiety (G—M) linked by a group (Q).

The group Q may be, for example, a bond, O, S, CHOH, CHSH, $CHNH_2$, $CHNHR^3$, $CHNR^3R^4$, NH, $NR^3$, $(CH_2)_n$, $O(CH_2)_n$, $(CH_2)_nO(CH_2)_n$, wherein n is either 0, 1, 2, or 3, and $R^3$ and $R^4$ are each independently substituted or unsubstituted $C_1$–$C_5$ branched or straight chain alkyl, $C_2$–$C_5$ branched or straight chain alkenyl, arylalkyl, substituted or unsubstituted acyl, aryl, $C_3$–$C_8$ ring, optionally substituted with up to four heteroatoms. Preferably, Q is NH or $NR^3$. In other embodiments, the $R^3$ side chain may be bonded to the J or D groups or alternatively bonded to the G or M group to form a cyclic structure.

The term "side chain pocket" includes a region of ACE-2 which interacts with side chain pocket binding moieties.

The language "side chain pocket binding moiety" includes moieties which interact with the side chain pocket. Examples of possible side chain pocket binding moieties include hydrogen, branched or straight chain, substituted or unsubstituted lower alkyl, lower alkenyl, lower alkynyl, aryl, or heteroaryl moieties or amino acid side chains of a natural or unnatural amino acids. Examples of preferred side chain pocket binding moieties include substituted or unsubstituted, branched or straight chain alkyl groups, and uncharged or charged amino acid side chains such as those of alanine, valine, leucine, isoleucine, phenylalanine, tryptophan, methionine, glycine, serine, threonine, cysteine, tyrosine, asparagine, proline, arginine, glutamic acid, aspartic acid, lysine, histidine and glutamine. Also included are non-natural amino acid side chains, e.g., derived from substituted natural amino acids, analogs of natural amino acids, derivatives of natural amino acids, and other non-naturally occurring amino acids. The side chain pocket binding moieties may also include substituted or unsubstituted heterocyclic moieties which may include imidazoles, thiazoles, pyrazoles, and benzimidiazoles.

Furthermore, the side chain pocket binding moiety may be of the formula:

wherein
$R^8$ is hydrogen, or alkyl, and optionally may be linked to form a cyclic structure with the D group;
J is selected from the group consisting of a bond, O, S, CHOH, CHSH, $CHNH_2$, $CHNHR^3$, $CHNR^3R^4$, NH, $NR^3$, $(CH_2)_n$, $O(CH_2)_n$, $(CH_2)_pO(CH_2)_n$, a chain of 1 to 5 atoms (e.g., carbon) optionally substituted by $C_1$–$C_6$ alkyl, halogens, wherein n is either 0, 1, 2, or 3, and p is 0, 1, 2, or 3; and $R^3$ and $R^4$ are each independently substituted or unsubstituted $C_1$–$C_6$ branched or straight chain alkyl, $C_1$–$C_6$ branched or straight chain alkenyl, substituted or unsubstituted acyl, alkynyl, aralkyl, aryl, $C_3$–$C_8$ ring, optionally substituted with up to four heteroatoms; and
D is hydrogen, alkyl, alkenyl, amine, hydroxy, alkynyl, aryl, or heteroaryl, any of which optionally may be branched or substituted.

In one embodiment, J is a bond and D is alkyl (e.g., methyl, ethyl, isopropyl, n-propyl, isobutyl, n-butyl, t-butyl, pentyl, etc.) or alkynyl. Furthermore, D may be phenyl, or heteroaryl, e.g., pyridinyl or imidazolyl. In certain embodiments, J and D are unsubstituted alkyl, alkynyl, aryl, or alkenyl.

The term "auxiliary pocket" includes a region of ACE-2 which interacts with auxiliary pocket binding moieties.

The term "auxiliary pocket binding moiety" includes moieties which interact with the auxiliary pocket of ACE-2. Examples of possible auxiliary pocket binding moieties include hydrogen, branched or straight chain, substituted or unsubstituted alkyl, aryl, aralkyl, heteroarylalkyl, alkenyl, alkynyl, or heteroaryl moieties, or amino acid side chains of a natural or unnatural amino acid. In certain embodiments, auxiliary pocket binding moieties may interact with metals associated with ACE-2, e.g., zinc.

Examples of "auxiliary pocket binding moieties" include moieties of the formula:

wherein $R^9$ is lower alkyl, or preferably, hydrogen, G is a linking moiety; and M is anchor moiety.

The term "linking moiety" or "G" includes moieties which link the anchor moiety with the ACE-2 modulating compound. For example, the term "linking moiety" includes covalent bonds, $C_1$–$C_6$ alkyl, alkenyl, alkynyl, ether, ester, thioether, amine, and carbonyl moieties. In another embodiment, the linking moiety is a covalent bond, amine $C_1$–$C_6$, $C_1$–$C_5$, $C_1$–$C_4$, $C_1$–$C_3$, or $C_1$–$C_2$ alkyl. The linking moiety may be substituted with up to three, four, five, or six heteroatoms.

The term "anchor moiety" or "M" includes moieties which interact with the auxiliary binding pocket of ACE-2. In certain embodiments, these moieties may also interact with metals, e.g., zinc, associated with ACE-2. The term "anchor moiety" includes moieties which allow the ACE-2 interacting compound to perform its intended function. Examples of anchor moieties include, for example, hydrogen atoms, unsubstituted or substituted alkyl, alkenyl, alkynyl, carbocyclic groups, e.g., substituted or unsubstituted phenyl, or heterocyclic, e.g., substituted or unsubstituted furanyl, imidazolyl, benzothiophenyl, benzofuranyl, quinolinyl, isoquinolinyl, benzodioxazolyl, benzoxazolyl, benzothiazolyl, benzoimidazolyl, thiazolyl, isothiazolyl, oxazolyl, isooxazolyl, methylenedioxyphenyl, indolyl, thienyl, pyrimidyl, pyrazinyl, pyrazolyl, purinyl, or deazapurinyl, naphthyl, napthridinyl, or indolizinyl. Examples of substituents include alkyl, alkenyl, alkynyl, aryl, NR'R", CN, $NO_2$, F, Cl, Br, I, $CF_3$, $CCl_3$, $CHF_2$, $CHCl_2$, CONR'R", $S(O)_2NR'R"$, CHO, $OCF_3$, $OCCl_3$, $SCF_3$, $SCCl_3$, COR', $CO_2R'$, and OR' and wherein R' and R" are each independently hydrogen, $C_1$–$C_6$ alkyl, $C_2$–$C_6$ alkenyl, $C_2$–$C_6$ alkynyl or optionally substituted aryl.

In one advantageous embodiment, the anchor moiety ("M") is substituted with at least one subanchor moiety. Each subanchor moiety ("L") may optionally be linked to the anchor moiety through a sublinking moiety ("K")

The term "subanchor moiety" or "L" includes hydrogen, alkyl, alkenyl, alkynyl, carbocyclic groups, aryl groups, e.g., substituted or unsubstituted phenyl, biphenyl, or heterocyclic, heteroaryl groups e.g., substituted or unsubstituted furanyl, imidazolyl, benzothiophenyl, benzofuranyl, quinolinyl, isoquinolinyl, benzodioxazolyl, benzoxazolyl, benzothiazolyl, benzoimidazolyl, thiazolyl, isothiaozolyl, oxazolyl, isooxazolyl, methylenedioxyphenyl, indolyl, thienyl, pyrimidyl, pyrazinyl, purinyl, or deazapurinyl, biphenyl, naphthyl, indazolyl, napthridinyl, or indolizinyl. In one advantageous embodiment, the subanchor moiety is aliphatic or aromatic, e.g., unsubstituted or substituted carbocyclic, heterocyclic, or phenyl. Preferably, the subanchor moiety allows the ACE-2 inhibiting compound to perform its intended function, e.g., inhibit ACE-2 function. In certain embodiments, a molecule of the invention may comprise one or more subanchor moieties.

Examples of subanchor moieties include, for example, 4-chlorophenyl, biphenyl, 3-chlorophenyl, 3,5-dichlorophenyl, 3-methylphenyl, 3,5-dimethylphenyl, 3-$CF_3$-phenyl, 2,5-dichlorophenyl, m-fluorophenyl, m-iodophenyl, methylenedioxyphenyl, m-trifluoromethylphenyl, 2,3-dichlorophenyl, 2,3-difluorophenyl, 2,3-dimethoxyphenyl, p-fluorophenyl, p-nitrophenyl, p-t-butylphenyl, p-isopropyl phenyl, p-trifluoromethoxyphenyl, 3,4-dimethylphenyl, 4-cyanophenyl, 3,4-chlorophenyl, 4-methylphenyl, and 4-trifluoromethylphenyl.

The term "sublinking moiety" or "K" includes moieties which link the subanchor moiety with the anchor moiety. For example, the term "sublinking moiety" includes covalent bonds, $C_1$–$C_6$ alkyl, alkenyl, alkynyl, ether, ester, thioether, amine, amide and carbonyl moieties. In another embodiment, the linking moiety is a covalent bond, amine or $C_1$–$C_6$ alkyl. A subanchor moiety may be connected to the anchor moiety through one or more sublinking moieties. Examples of sublinking moieties also include O, S, CHOH, $(CH_2)_n$—$SO_2$, $CHNH_2$, $CHNHR^3$, $CHNR^3R^4$, NH, $NR^3$, $(CH_2)_n$, $O(CH_2)_n$, $(CH_2)_nO(CH_2)_n$, a chain of 1 to 6 atoms optionally substituted by $C_1$–$C_6$ alkyl, halogens, wherein n is either 0, 1, 2, or 3, and $R^3$ and $R^4$ are each independently substituted or unsubstituted $C_1$–$C_6$ branched or straight chain alkyl, aryl, aralkyl, substituted or unsubstituted acyl, $C_3$–$C_8$ ring, optionally substituted with up to four heteroatoms. In a further embodiment, the sublinking moiety is a covalent bond, an ether, an amine, or $C_1$–$C_3$ alkyl (e.g., —$CH_2$—, —$CH_2CH_2$—, etc.).

For example, in one embodiment, the anchor moiety includes cyclic.moieties of the formula:

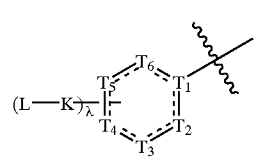

wherein

λ is, 1, 2, 3, 4, or 5;

$T_1$, $T_2$, $T_3$, $T_4$, and $T_5$ are each independently carbon, nitrogen, sulfur, or oxygen, optionally bound to hydrogen;

$T_6$ is carbon, nitrogen, sulfur, oxygen or a covalent bond (such that a five membered ring is formed);

each K is an independently selected sublinking moiety; and each L is an independently selected subanchor moiety. The sublinking and subanchor moieties may be attached to any available atom of the aromatic or heteroaromatic ring. Furthermore, two or more sublinking moieties may be attached to the same subanchor moiety, forming a bicyclic or tricyclic ring system.

Examples of anchor moieties include moieties wherein $T_2$ and $T_4$ are nitrogen, $T_1$, $T_3$ and $T_5$ are carbon and $T_6$ is a covalent bond. Another example of an anchor moiety includes the moiety wherein $T_2$ and $T_3$ are nitrogen, $T_1$, $T_4$, $T_5$ are each carbon, and $T_6$ is a covalent bond. Another example of an anchor moiety includes the moiety wherein $T_1$, $T_3$, and $T_5$ are each carbon, $T_2$ is nitrogen, and $T_4$ is sulfur.

For example, in one embodiment, the anchor moiety is substituted or unsubstituted pyrazolyl, thioazolyl, or oxazolyl or imidazolyl. In a further embodiment, the imidazolyl anchor moiety is substituted with one or more subanchor moieties ("L"), linked to the imidazolyl anchor moiety through sublinking moieties ("K"). In one embodiment, the imidazolyl anchor moiety is represented by the formula:

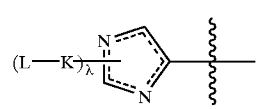

wherein

λ is 0, 1, 2, 3, or 4;

each K is an independently selected sublinking moiety; and each L is an independently selected subanchor moiety. The sublinking and subanchor moieties may be attached to any available atom of the imidazole ring.

Furthermore, two or more sublinking moieties may be attached to the same subanchor moiety, forming a bicyclic or tricyclic ring system.

In one embodiment, the imidazolyl anchor moiety is of the formula:

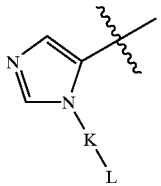

In an embodiment, K is a covalent bond, aminocarbonyl, $(CH_2)_n$ or $(CH_2)_pO(CH_2)_n$, wherein n is 0, 1, 2, 3, 4, or 5 and p is 0, 1, 2, 3, 4, or 5. In another embodiment, L is a subanchor moiety, such as, but not limited to, unsubstituted or substituted phenyl, alkyl or cyclic alkyl. L, e.g., phenyl or another subanchor moiety, can be substituted with one or more substituents that allow the compound to perform its intended function, e.g., modulate ACE-2 activity. Examples of substituents include alkyl, alkenyl, alkynyl, aryl, NR'R", CN, $NO_2$, F, Cl, Br, I, $CF_3$, $CCl_3$, $CHF_2$, $CHCl_2$, CONR'R", S(O)NR'R", CHO, $OCF_3$, $OCCl_3$, $SCF_3$, $SCCl_3$, COR', $CO_2R'$, and OR' and wherein R' and R" are each independently hydrogen, $C_1$–$C_4$ alkyl, or optionally substituted aryl. In one embodiment, L is phenyl and is substituted with a nitro group. In other embodiments, L is 4-chlorophenyl, biphenyl, 3-chlorophenyl, 3,5-dichlorophenyl, 3-methylphenyl, 3,5-dimethylphenyl, 3-$CF_3$-phenyl, 2,5-dichlorophenyl, m-fluorophenyl, m-iodophenyl, methylenedioxyphenyl, m-trifluoromethylphenyl, 2,3-dichlorophenyl, 2,3-difluorophenyl, 2,3-dimethoxyphenyl, p-fluorophenyl, p-nitrophenyl, p-t-butylphenyl, p-isopropyl phenyl, p-trifluoromethoxyphenyl, 3,4-dimethylphenyl, 4-cyanophenyl, 3,4-chlorophenyl, 4-methylphenyl, and 4-trifluoromethylphenyl.

The ACE-2 modulating compound of the invention, e.g., ACE-2 inhibitors, may be identified through assays which determine the compound's $K_i$. An example of such an assay is the ACE-2 Competitive Substrate Assay (ACS Assay). The ACS assay determines the ability of a compound to inhibit the activity of ACE-2 by having a test compound compete with a known ACE-2 substrate and determining the amount of known substrate converted by ACE-2 to its cleaved products. The ACE-2 assay is described in greater detail in Example 8. The invention includes ACE-2 inhibiting compounds which interact with ACE-2 with a $K_i$ of 50 $\mu$M or less, 40 $\mu$M or less, 20 $\mu$M or less, 10 $\mu$M or less, 1 $\mu$M or less, 0.75 $\mu$M or less, 0.1 $\mu$M or less, 0.50 $\mu$M or less, 0.25 $\mu$M or less, 0.10 $\mu$M or less, 0.075 $\mu$M or less, 0.050 $\mu$M or less, 0.040 $\mu$M or less, 0.030 $\mu$M or less, 0.025 $\mu$M or less, 0.01 $\mu$M or less, 0.0075 $\mu$M or less, 0.005 $\mu$M or less, 0.0025 $\mu$M or less, or, advantageously, 0.0015 $\mu$M or less.

The invention also pertains to an ACE-2 inhibiting compound of the formula (II):

Z—A—B—E (II)

wherein Z is a zinc coordinating moiety, E is an enzyme coordinating moiety, A is a auxiliary pocket binding moiety; and B is a side chain binding pocket moiety. Preferably, the compound is an ACE-2 inhibiting compound.

The language "enzyme coordinating moiety" or "E" includes, preferably, carboxylic acids, hydrogen, and cleavable carboxylic acid prodrug moieties. It includes electron rich moieties which are able to coordinate to the enzyme to facilitate inhibition of ACE-2. The enzyme coordinating moiety also includes prodrugs which can be hydrolyzed in vivo to an active form. The language "enzyme coordinating moiety" includes any moiety, which, in vivo and/or in vitro, allows for interactions to occur between the ACE-2 modulating compound and ACE-2. In one embodiment, E is a carboxylic acid or a carboxylic acid equivalent.

The language "carboxylic acid equivalent" includes moieties which allow the ACE-2 modulating compound to perform its intended function, e.g., modulate ACE-2 function. Examples of carboxylic acid equivalents include, for example, $—SO_3H$, $—PO_3H$, $—SO_2NH_2$, $—SO_2NHCH_3$, $—CONHSO_2R$, $—SO_2NHCF_3$, $—NHSO_2CH_3$, $—NHSO_2CF_3$, —CONHOH, —CONHCN, and other carboxylic acid isoteres. In one embodiment, E is $CO_2H$, $CO_2—R^5$, $CONH_2$, $CONHR^5$, $CONR^5R^5$, or hydrogen, wherein $R^5$ is substituted or unsubstituted $C_1$–$C_5$ branched or straight chain alkyl, $C_2$–$C_5$ branched or straight chain alkenyl, aryl, $C_3$–$C_8$ ring, optionally substituted with up to four heteroatoms.

In another embodiment, the invention pertains to an ACE-2 inhibiting compound of the formula (III):

(III)

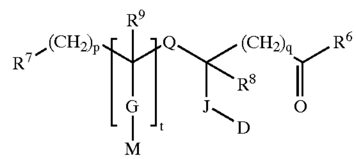

wherein $R^6$ is hydroxyl or a protecting prodrug moiety;

$R^7$ is an hydrogen atom, carboxylic acid, arylaminocarboxy, aroyl, aryl, alkylaminocarboxy, aminocarboxy, alkenylaminocarboxy, a protecting prodrug moiety, hydroxyl, heterocycle, alkoxy, ether, thiol or an amine;

Q is a bond, O, S, CHOH, CHSH, $CHNH_2$, $CHNHR^3$, $CHNR^3R^4$, NH, $NR^3$, $(CH_2)_n$, $O(CH_2)_n$, $(CH_2)_nO(CH_2)_n$, wherein n is either 0, 1, 2, or 3, and $R^3$ and $R_4$ are each independently substituted or unsubstituted $C_1$–$C_5$ branched or straight chain alkyl, $C_2$–$C_5$ branched or straight chain alkenyl, substituted or unsubstituted acyl, aryl, $C_3$–$C_8$ ring, optionally substituted with up to four heteroatoms;

G is a linking moiety;

M is an anchor moiety;

J is a bond, an alkyl, alkenyl, or alkynyl moiety;

D is hydrogen, alkyl, alkenyl, alkynyl, aryl, or heteroaryl, optionally linked to G, M or Q to form a ring;

t is 0, 1, 2, or 3;

p is 0, 1, 2, 3, 4, or 5; and q is 0, 1, 2, or 3.

In a further embodiment, $R^6$ is hydroxyl, an amino acid (e.g., glycine, alanine), branched or unbranched, substituted or unsubstituted lower alkyls (e.g., methyl, ethyl, propyl groups), lower alkenyl groups (e.g., ethenenyl, propenyl, butenyl, pentenyl), di-lower amino-lower alkyl groups (dimethylamino, diethylamino, diisopropylamino, di-n-propylamino, methylethylamino, methylpropylamino, etc.) acylamino lower alkyl groups, acyloxy lower alkyl groups, aryl groups (e.g., phenyl, furanyl, biphenyl, napthridinyl, pyrazolyl, etc.), aryl lower alkyl groups, and substituted aryl or aryl lower alkyl groups.

In a further embodiment, $R^8$ is hydrogen, or alkyl (e.g., methyl, ethyl, propyl, butyl), optionally linked to D to form a ring.

In a further embodiment, $R^9$ is lower alkyl (e.g., methyl, ethyl, propyl, or butyl) or hydrogen.

In a further embodiment, Q is a bond, O, S, CHOH, CHSH, $CHNH_2$, $CHNHR^3$, $CHNR^3R^4$, NH, $NR^3$, $(CH_2)_n$, $O(CH_2)_n$, $(CH_2)_nO(CH_2)_n$, wherein n is either 0, 1, 2, or 3, and $R^3$ and $R^4$ are each independently substituted or unsubstituted $C_1-C_5$ branched or straight chain alkyl, $C_2-C_5$ branched or straight chain alkenyl, substituted or unsubstituted acyl, aryl, $C_3-C_8$ ring, optionally substituted with up to four heteroatoms.

In a further embodiment, G is a bond, $C_1$, $C_2$, $C_3$, $C_4$, $C_5$ or $C_6$ alkyl, alkenyl, alkynyl, ether, ester, thioether, amine, or carbonyl, optionally substituted with up to three, four, five, or six heteroatoms.

In a further embodiment, M is a hydrogen atom, alkyl (straight, branched or cycloalkyl), alkenyl, alkynyl, heterocyclic, carbocyclic, aryl, e.g., phenyl, biphenyl, heteroaryl, e.g., furanyl, imidazolyl, benzothiophenyl, benzofuranyl, quinolinyl, isoquinolinyl, benzodioxazolyl, benzoxazolyl, benzothiazolyl, benzoimidazolyl, thiazolyl, isothiazolyl, oxazolyl, benzothiazolyl, isooxazolyl, methylenedioxyphenyl, indolyl, thienyl, pyrimidyl, pyrazinyl, pyrazolyl, purinyl, deazapurinyl, naphthyl, napthridinyl, or indolizinyl, wherein in M is optionally substituted with, for example, alkyl, alkenyl, alkynyl, aryl, NR'R", CN, $NO_2$, F, Cl, Br, I, $CF_3$, $CCl_3$, $CHF_2$, $CHCl_2$, CONR'R", $S(O)_2NR'R"$, CHO, $OCF_3$, $OCCl_3$, $SCF_3$, $SCCl_3$, COR', $CO_2R'$, and OR' and wherein R' and R" are each independently hydrogen, $C_1-C_6$ alkyl, $C_2-C_6$ alkenyl, $C_2-C_6$ alkynyl or substituted or unsubstituted aryl.

Various groups can be linked to form rings. For example, in a further embodiment, $R^8$ and $R^9$ are hydrogen or alkyl. In another further embodiment, $R^8$ is alkyl and is linked to D to form a ring. In another further embodiment, $R^9$ is alkyl and is linked with M to form a ring. In yet another further embodiment, D and Q are linked to form a ring. In another embodiment, the invention pertains to an ACE-2 inhibiting compound of the formula (IV):

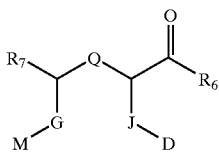

(IV)

wherein $R_6$ is —OH or a protecting prodrug moiety; $R_7$ is an hydrogen atom, carboxylic acid, an amide, a protecting prodrug moiety, hydroxyl, thiol, heterocycle (e.g., imidazole, thiazole, oxazole), ether, alkoxy, or an amine; Q is $CH_2$, O, NH, or $NR^3$; G is a linking moiety as described above, a covalent bond, $C_1-C_5$ alkyl, alkenyl, alkynyl, ether, thioether, amine, or carbonyl; M is an anchor moiety as described above, alkyl, hydrogen, aryl, heteroaryl, heterocyclic, or carbocyclic; J is a bond, alkyl, alkenyl, or alkynyl moiety; and D is alkyl, alkenyl, alkynyl, aryl, or heteroaryl, optionally linked to G or M to form a ring. In a further embodiment, M comprises a subanchor moiety, as defined above.

In an embodiment, $R_7$ is a carboxylic acid group; G is a covalent bond, $C_1-C_3$ alkyl, or aminoalkyl; and M is phenyl, or heteroaryl (e.g., thienyl, triazolyl, thiazolyl, or imidazolyl). In another embodiment, J is a covalent bond or alkynyl. D may be alkyl (e.g., n-propyl, methyl, isopropyl, ethyl, cycloalkyl, or butyl), a side chain of a natural or unnatural amino acid, or heteroaryl (e.g., pyridinyl or imidozlyl).

In one embodiment, the ACE-2 compounds of the invention do not include compound BD, 2-(1-carboxy-ethylamino)-3-(1H-imidazol-4-yl)-propionic acid.

Examples of ACE-2 inhibiting compounds include:

2-{1-Carboxy-2-[3-(3-nitro-benzyl)-3H-imidazol-4-yl]-ethylamino}-4-methyl-pentanoic acid;

2-[2-(3-Benzyl-3H-imidazol-4-yl)-1-carboxy-ethylamino]-hexanoic acid;

2-[2-(3-Benzyl-3H-imidazol-4-yl)-1-carboxy-ethylamino]-4-methyl-pentanoic acid;

2-[1-Carboxy-2-(1H-imidazol-4-yl)-ethylamino]-4-phenyl-butyric acid;

2-[2-(3-Benzyloxymethyl-3H-imidazol-4-yl)-1-carboxy-ethylamino]-4-methyl-pentanoic acid;

2-[1-Carboxy-2-(methyl-phenyl-amino)-ethylamino]-4-methyl-pentanoic acid;

2-[1-Carboxy-2-(1H-imidazol-4-yl)-ethylamino]-4-methyl-pentanoic acid;

2-[2-(1-Benzyl-1H-imidazol-4-yl)-1-carboxy-ethylamino]-4-methyl-pentanoic acid;

2-(1-Carboxy-2-phenyl-ethylamino)-3-(3H-imidazol-4-yl)-propionic acid;

2-[1-Carboxy-2-(1H-imidazol-4-yl)-ethylamino]-4-methyl-pentanoic acid;

2-[1-Carboxy-2-(4-hydroxy-phenyl)-ethylamino]-3-(1H-imidazol-4-yl)-propionic acid;

2-[1-Carboxy-2-(1H-imidazol-4-yl)-ethylamino]-4-phenyl-butyric acid;

2-[1-Carboxy-2-(1H-imidazol-4-yl)-ethylamino]-pentanoic acid;

2-[2-(1H-Imidazol-4-yl)-1-methoxycarbonyl-ethylamino]-4-methyl-pentanoic acid;

2-(1-Carboxy-3-phenyl-propylamino)-5-pyridin-2-yl-pent-4-ynoic acid;

2-{1-Carboxy-2-[1-(4-chloro-benzyl)-1H-imidazol-4-yl]-ethylamino}-4-methyl-pentanoic acid;

2-[2-(1-Benzyl-1H-imidazol-4-yl)-1-carboxy-ethylamino]-4-methyl-pentanoic acid;

2-[1-Carboxy-2-(1H-imidazol-4-yl)-ethylamino]-pentanoic acid;

2-[1-Carboxy-2-(1H-imidazol-4-yl)-ethylamino]-hexanoic acid;

2-(1-Carboxy-2-thiophen-2-yl-ethylamino)-4-methyl-pentanoic acid;

6-Amino-2-(1-carboxy-3-phenyl-propylamino)-hexanoic acid;

2-[1-Carboxy-2-(1H-imidazol-4-yl)-ethylamino]-3-methyl-pentanoic acid;

2-[(Carboxy-phenyl-methyl)-amino]-4-methyl-pentanoic acid;

2-{1-Carboxy-2-[1-(2,4-dinitro-phenyl)-1H-imidazol-4-yl]-ethylamino}-4-methyl-pentanoic acid;

2-(1-Carboxy-2-thiazol-2-yl-ethylamino)-4-methyl-pentanoic acid;

2-(1-Carboxy-2-pyridin-2-yl-ethylamino)-4-methyl-pentanoic acid;

2-(1-Carboxy-ethylamino)-3-(1H-imidazol-4-yl)-propionic acid;

2-(1-Carboxy-3-methylsulfanyl-propylamino)-4-phenyl-butyric acid;

2-(1-Carboxy-3-methyl-butylamino)-succinic acid;

2-(1-Carboxy-3-methyl-butylamino)-hexanoic acid;

2-(1-Carboxy-3-methylsulfanyl-propylamino)-4-methyl-pentanoic acid;

2-[1-Carboxy-2-(3-methyl-3H-imidazol-4-yl)-ethylamino]-4-methyl-pentanoic acid;

2-(1-Carboxy-3-phenyl-propylamino)-4-methyl-pentanoic acid;

2-(1-Carboxy-2-phenyl-ethylamino)-4-methyl-pentanoic acid;

2-(1-Carboxy-2-phenyl-ethylamino)-pentanoic acid;

2-(1-Carboxy-2-phenyl-ethylamino)-4-phenyl-butyric acid;

2-(1-Carboxy-3-phenyl-propylamino)-4,4-dimethyl-pentanoic acid;

2-(1-Carboxy-ethylamino)-3-(1H-imidazol-4-yl)-propionic acid;

2-(1-Carboxy-2-thiophen-2-yl-ethylamino)-pentanoic acid;

2-[1-Carboxy-2-(1H-[1,2,4]triazol-3-yl)-ethylamino]-4-methyl-pentanoic acid;

2-(1-Carboxy-2-cyclopropyl-ethylamino)-4-phenyl-butyric acid;

2-[1-Carboxy-2-(4-hydroxy-phenyl)-ethylamino]-3-(1H-imidazol-4-yl)-propionic acid;

2-[2-(1-Benzyl-1H-imidazol-4-yl)-1-carboxy-ethylamino]-4-methyl-pentanoic acid;

2-(1-Carboxy-2-cyclohexyl-ethylamino)-4-phenyl-butyric acid;

2-(1-Carboxy-3-phenyl-propylamino)-5-phenyl-pent-4-ynoic acid;

2-[2-(1H-Imidazol-4-yl)-1-methoxycarbonyl-ethylamino]-4-methyl-pentanoic acid;

2-{1-Carboxy-2-[1-(4-methoxy-benzyl)-1H-imidazol-4-yl]-ethylamino}-4-methyl-pentanoic acid;

2-{1-Carboxy-2-[1-(4-trifluoromethyl-benzyl)-1H-imidazol-4-yl]-ethylamino}-4-methyl-pentanoic acid;

2-[(Carboxy-phenyl-methyl)-amino]-4-methyl-pentanoic acid;

2-(1-Carboxy-propylamino)-4-methylsulfanyl-butyric acid; and

2-[1-Carboxy-2-phenyl-ethylamino]-4-methyl-pentanoic acid;

2-[2-(1H-Imidazol-4-yl)-1-methoxycarbonyl-ethylamino]-4-methyl-pentanoic acid;

2-{1-Carboxy-2-[1-(4-methoxy-benzyl)-1H-imidazol-4-yl]-ethylamino}-4-methyl-pentanoic acid;

2-{1-Carboxy-2-[1-(4-trifluoromethyl-benzyl)-1H-imidazol-4-yl]-ethylamino}-4-methyl-pentanoic acid;

2-[(Carboxy-phenyl-methyl)-amino]-4-methyl-pentanoic acid;

2-(1-Carboxy-propylamino)-4-methylsulfanyl-butyric acid;

2-(1-Carboxy-3-phenyl-propylamino)-5-pyridin-2-yl-pent-4-ynoic acid;

2-{1-Carboxy-2-[3-(4-trifluoromethyl-benzyl)-3H-imidazol-4-yl]-ethylamino}-4-methyl-pentanoic acid;

2-[1-Carboxy-2-(3-naphthalen-1-ylmethyl-3H-imidazol-4-yl)-ethylamino]-4-methyl-pentanoic acid;

2-[1-Carboxy-2-[3-(4-chloro-benzyl)-3H-imidazol-4-yl]-ethylamino]-4-methyl-pentanoic acid;

4-{5-[2-Carboxy-2-(1-carboxy-3-methyl-butylamino)-ethyl]-imidazol-1-ylmethyl}-benzoic acid;

4-{5-[2-Carboxy-2-(1-carboxy-3-methyl-butylamino)-ethyl]-imidazol-1-ylmethyl}-benzoic acid;

2-[1-Carboxy-2-(2-phenyl-thiazol-4-yl)-ethylamino]-4-methyl-pentanoic acid;

2-[2-(1-Benzyl-1H-benzoimidazol-2-yl)-1-carboxy-ethylamino]-4-methyl-pentanoic acid;

2-[2-(Benzyl-phenyl-amino)-1-carboxy-ethylamino]-4-methyl-pentanoic acid;

2-[2-(2-Amino-thiazol-4-yl)-1-carboxy-ethylamino]-4-methyl-pentanoic acid;

2-{1-Carboxy-2-[3-(3,4-dichloro-benzyl)-3H-imidazol-4-yl]-ethylamino}-4-methyl-pentanoic acid;

2-[1-Carboxy-2-(2-methyl-thiazol-4-yl)-ethylamino]-4-methyl-pentanoic acid;

2-{1-Carboxy-2-[3-(4-cyano-benzyl)-3H-imidazol-4-yl]-ethylamino}-4-methyl-pentanoic acid;

2-{1-Carboxy-2-[3-(3-chloro-benzyl)-3H-imidazol-4-yl]-ethylamino}-4-methyl-pentanoic acid;

'2-{1-Carboxy-2-[3-(3,5-dichloro-benzyl)-3H-imidazol-4-yl]-ethylamino}-4-pentanoic acid 2-{1-Carboxy-2-[3-(4-methyl-benzyl)-3H-imidazol-4-yl]-ethylamino}-4-methyl-pentanoic acid;

2-{2-[3-(4-Butyl-benzyl)-3H-imidazol-4-yl]-1-carboxy-ethylamino}-4-methyl acid;

2-{1-Carboxy-2-[3-(3,4-dimethyl-benzyl)-3H-imidazol-4-yl]-ethylamino}-4-methyl-pentanoic acid;

2-[2-(2-Benzylamino-thiazol-4-yl)-1-carboxy-ethylamino]-4-methyl-pentanoic acid;

2-{1-Carboxy-2-[3-(3-methyl-benzyl)-3H-imidazol-4-yl]-ethylamino}-4-methyl-pentanoic acid;

2-{1-Carboxy-2-[3-(3,5-dimethyl-benzyl)-3H-imidazol-4-yl]-ethylamino}-4-methyl-pentanoic acid;

2-{1-Carboxy-2-[3-(4-trifluoromethoxy-benzyl)-3H-imidazol-4-yl]-ethylamino -4-methyl-pentanoic acid;

2-{1-Carboxy-2-[3-(4-isopropyl-benzyl)-3H-imidazol-4-yl]-ethylamino}-4-methyl-pentanoic acid;

2-{1-Carboxy-2-[3-(2-methyl-benzyl)-3H-imidazol-4-yl]-ethylamino}-4-methyl-pentanoic acid;

2-{2-[3-(4-tert-Butyl-benzyl)-3H-imidazol-4-yl]-1-carboxy-ethylamino}-4-methyl-pentanoic acid;

2-{2-[3-(2-Benzenesulfonylmethyl-benzyl)-3H-imidazol-4-yl]-1-carboxy-ethylamino}-4-methyl-pentanoic acid;

2-{1-Carboxy-2-[3-(4-nitro-benzyl)-3H-imidazol-4-yl]-ethylamino}-4-methyl-pentanoic acid;

2-[2-(3-Biphenyl-2-ylmethyl-3H-imidazol-4-yl)-1-carboxy-ethylamino]-4-methyl-pentanoic acid;

'2-{2-[3-(3,5-Bis-trifluoromethyl-benzyl)-3H-imidazol-4-yl]-1-carboxy-ethylamino}-4-methyl-pentanoic acid;

2-{1-Carboxy-2-[3-(4-fluoro-benzyl)-3H-imidazol-4-yl]-ethylamino}-4-methyl-pentanoic acid;

2-{1-Carboxy-2-[3-(4-fluoro-benzyl)-3H-imidazol-4-yl]-ethylamino}-4-methyl-pentanoic acid;

2-[1-Carboxy-2-(2-phenyl-thiazol-4-yl)-ethylamino]-4-methyl-pentanoic acid;

2-[1-Carboxy-2-(5-methyl-isoxazol-3-yl)-ethylamino]-4-methyl-pentanoic acid;

2-[2-(1-Benzyl-1H-pyrazol-3-yl)-1-carboxy-ethylamino]-4-methyl-pentanoic acid;

2-{1-Carboxy-2-[3-(2,3-dimethoxy-benzyl)-3H-imidazol-4-yl]-ethylamino}-4-methyl-pentanoic acid;

2-{1-Carboxy-2-[3-(2-methyl-biphenyl-3-ylmethyl)-3H-imidazol-4-yl]-ethylamino}-methyl-pentanoic acid;

'2-{1-Carboxy-2-[3-(2-methoxy-naphthalen-1-ylmethyl)-3H-imidazol-4-yl]-ethylamino}-4-methyl-pentanoic acid;

2-{1-Carboxy-2-[3-(2,3-difluoro-benzyl)-3H-imidazol-4-yl]-ethylamino}-4-methyl-pentanoic acid;

2-{1-Carboxy-2-[1-(2,3-difluoro-benzyl)-1H-imidazol-4-yl]-ethylamino}-4-methyl-pentanoic acid;

2-{1-Carboxy-2-[3-(2,3-dichloro-benzyl)-3H-imidazol-4-yl]-ethylamino}-4-methyl-pentanoic acid;

'2-{1-Carboxy-2-[-(3-trifluoromethyl-benzyl)-3H-imidazol-4-yl]-ethylamino-4-methyl-pentanoic acid;

2-{1-Carboxy-2-[3-(2,5-dichloro-benzyl)-3H-imidazol-4-yl]-ethylamino}-4-methyl-pentanoic acid; and 2-{1-Carboxy-2-[3-(2,6-dichloro-benzyl)-3H-imidazol-4-yl]-ethylamino}-4-methyl-pentanoic acid.

4-Methyl-2-[1-methylcarbamoyl-2-(3-phenylamino-3H-imidazol-4-yl)-ethylamino]-pentanoic acid;

2-[2-(4-Benzyl-furan-3-yl)-1-carboxy-ethylamino]-4-methyl-pentanoic acid;

2-[1-Carboxy-2-(3-phenyl-3H-imidazol-4-yl)-ethylamino]-4-methyl-pentanoic acid;

2-[1-Carboxy-2-(3-phenethyl-3H-imidazol-4-yl)-ethylamino]-4-methyl-pentanoic acid;

2-{1-Carboxy-2-[3-(pyridin-3-yloxy)-3H-imidazol-4-yl]-ethylamino}-4-methyl-pentanoic acid;

2-{1-Carboxy-2-[3-(4-nitro-phenoxy)-3H-imidazol-4-yl]-ethylamino}-4-methyl-pentanoic acid;

2-[1-Carboxy-2-(3-phenoxy-3H-imidazol-4-yl)-ethylamino]-4-methyl-pentanoic acid;

2-{1-Carboxy-2-[3-(2-nitro-benzyl)-3H-imidazol-4-yl]-ethylamino}-4-methyl-pentanoic acid;

2-{1-Carboxy-2-[3-(3-nitro-benzyl)-3H-imidazol-4-yl]-ethylamino}-4-methyl-pentanoic acid;

2-{1-Carboxy-2-[3-(2-trifluoromethyl-benzyl)-3H-imidazol-4-yl]-ethylamino}-4-methyl-pentanoic acid;

2-{1-Carboxy-2-[3-(3-trifluoromethyl-benzyl)-3H-imidazol-4-yl]-ethylamino}-4-methyl-pentanoic acid;

2-{1-Carboxy-2-[3-(2-methyl-benzyl)-3H-imidazol-4-yl]-ethylamino}-4-methyl-pentanoic acid;

2-{1-Carboxy-2-[3-(3-methyl-benzyl)-3H-imidazol-4-yl]-ethylamino}-4-methyl-pentanoic acid;

2-{1-Carboxy-2-[3-(2-chloro-benzyl)-3H-imidazol-4-yl]-ethylamino}-4-methyl-pentanoic acid;

2-{1-Carboxy-2-[3-(3-chloro-benzyl)-3H-imidazol-4-yl]-ethylamino}-4-methyl-pentanoic acid;

2-{1-Carboxy-2-[3-(2-hydroxy-benzyl)-3H-imidazol-4-yl]-ethylamino}-4-methyl-pentanoic acid;

2-{1-Carboxy-2-[3-(3-hydroxy-benzyl)-3H-imidazol-4-yl]-ethylamino}-4-methyl-pentanoic acid;

2-{1-Carboxy-2-[3-(2-fluoro-benzyl)-3H-imidazol-4-yl]-ethylamino}-4-methylpentanoic acid;

2-[2-(3-Benzyl-3H-imidazol-4-yl)-1-carboxy-ethylamino]-4-methyl-pentanoic acid;

2-[1-Carboxy-2-(3-phenylamino-3H-imidazol-4-yl)-ethylamino]-4-methyl-pentanoic acid;

2-{[2,3-Dioxo-1-(3-phenylamino-3H-imidazol-4-ylmethyl)-butyl]-methyl-amino}-4-methyl-pentanoic acid;

2-{[2,3-Dioxo-1-(4-phenylamino-furan-3-ylmethyl)-butyl]-methyl-amino}-4-methyl-pentanoic acid;

2-[2,3-Dioxo-1-(4-phenylamino-furan-3-ylmethyl)-butylamino]-4-methyl-pentanoic acid;

2-[1-Carboxy-2-(4-phenylamino-furan-3-yl)-ethylamino]-4-methyl-pentanoic acid;

2-[1-Carboxy-2-(2-o-tolyl-2H-isoindol-1-yl)-ethylamino]-4-methyl-pentanoic acid;

2-[2-(2-Benzyl-2H-isoindol-1-yl)-1-carboxy-ethylamino]-4-methyl-pentanoic acid;

2-[1-Carboxy-2-(2-phenyl-2H-isoindol-1-yl)-ethylamino]-4-methyl-pentanoic acid;

2-[1-Carboxy-2-(2-pyridin-2-yl-2H-isoindol-1-yl)-ethylamino]-4-methyl-pentanoic acid;

2-{1-Carboxy-2-[2-(3-nitro-phenyl)-2H-isoindol-1-yl]-ethylamino}-4-methyl-pentanoic acid;

2-{1-Carboxy-2-[2-(4-nitro-phenyl)-2H-isoindol-1-yl]-ethylamino}-4-methyl-pentanoic acid;

2-{1-Carboxy-2-[2-(4-nitro-benzyl)-2H-isoindol-1-yl]-ethylamino}-4-methyl-pentanoic acid;

2-({Carboxy-[3-(4-nitro-phenyl)-naphthalen-1-yl]-methyl)}-amino)-4-methyl-pentanoic acid;

2-({Carboxy-[3-(4-nitro-benzyl)-naphthalen-1-yl]-methyl}-amino)-4-methyl-pentanoic acid;

'2-{1-Carboxy-2-[3-(3-trifluoromethyl-benzyl)-3H-imidazol-4-yl]-ethylamino}-4-methyl-pentanoic acid;

2-{1-Carboxy-2-[3-(2,5-dichloro-benzyl)-3H-imidazol-4-yl]-ethylamino}-4-methyl-pentanoic acid;

2-{1-Carboxy-2-[3-(2,6-dichloro-benzyl)-3H-imidazol-4-yl]-ethylamino}-4-methyl-pentanoic acid;

2-[1-Carboxy-2-(3-cyclohexylmethyl-3H-imidazol-4-yl)-ethylamino]-4-methyl-pentanoic acid;

2-[1-Carboxy-2-(3-phenethyl-3H-imidazol-4-yl)-ethylamino]-4-methyl-pentanoic acid;

2-{1-Carboxy-2-[3-(2-ethyl-butyl)-3H-imidazol-4-yl]-ethylamino}-4-methyl-pentanoic acid;

2-{1-Carboxy-2-[3-(3-iodo-benzyl)-3H-imidazol-4-yl]-ethylamino}-4-methyl-pentanoic acid;

2-{1-Carboxy-2-[3-(3-fluoro-benzyl)-3H-imidazol-4-yl]-ethylamino}-4-methyl-pentanoic acid;

2-{1-Carboxy-2-[3-(3-fluoro-benzyl)-3H-imidazol-4-yl]-ethylamino}-4-methyl-pentanoic acid;

2-[1-Carboxy-2-(2-phenylethynyl-1H-imidazol-4-yl)-ethylamino]-4-methyl-pentanoic acid;

2-[1-Carboxy-2-(1-methyl-2-phenylethynyl-1H-imidazol-4-yl)-ethylamino]-4-methyl-pentanoic acid;

2-[1-Carboxy-2-(2-phenethyl-1H-imidazol-4-yl)-ethylamino]-4-methyl-pentanoic acid;

2-[1-Carboxy-3-(3-phenyl-3H-imidazol-4-yl)-propylamino]-4-methyl-pentanoic acid;

2-[1-Carboxy-2-(3-phenyl-3H-imidazol-4-yl)-ethylamino]-4-methyl-pentanoic acid;

2-[2-(3-Benzyl-2,5-dimethyl-3H-imidazol-4-yl)-1-carboxy-ethylamino]-4-methyl-pentanoic acid;

2-[1-Carboxy-4-(3-phenyl-3H-imidazol-4-yl)-butylamino]-4-methyl-pentanoic acid;

2-[2-(2-Benzyl-thiazol-4-yl)-1-carboxy-ethylamino]-4-methyl-pentanoic acid; and

2-[2-(5-Benzyl-2-methyl-thiazol-4-yl)-1-carboxy-ethylamino]-4-methyl-pentanoic acid.

Preferred examples of ACE-2 inhibiting compounds include those having the structures shown below:
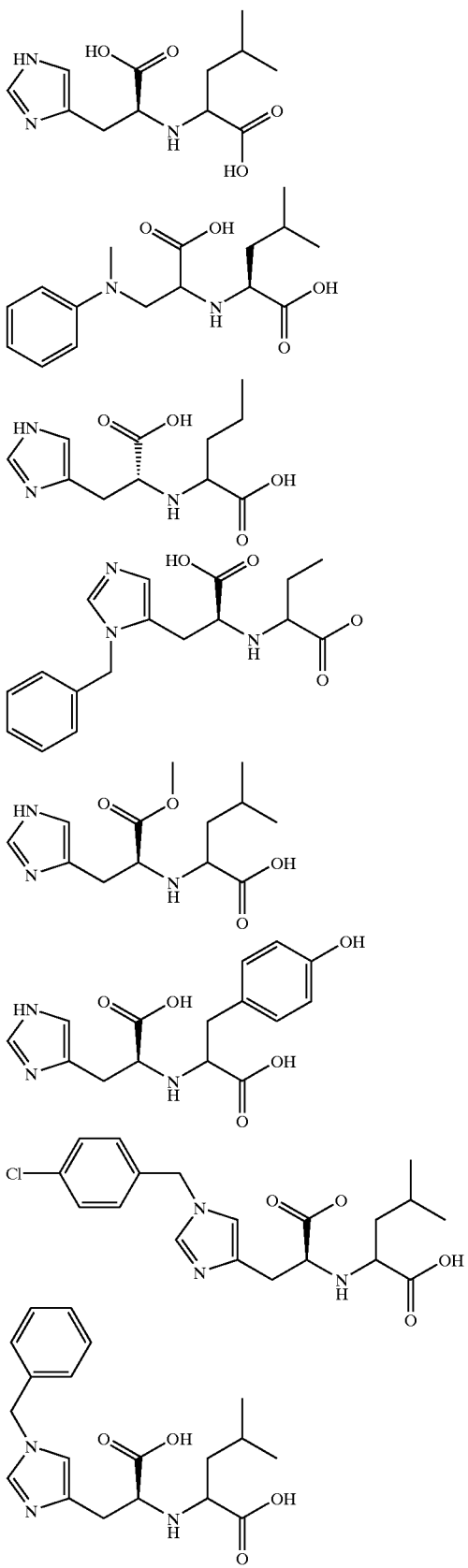
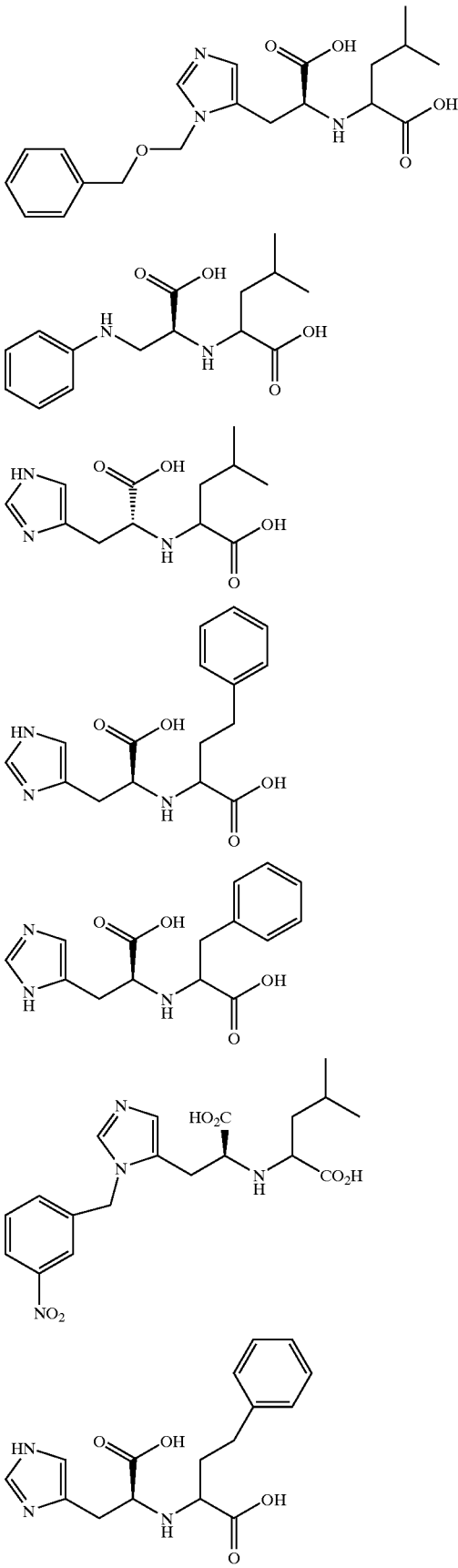

21
-continued
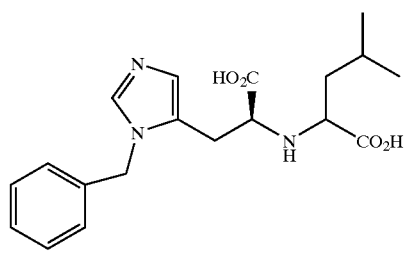
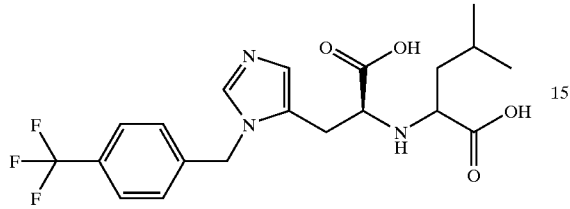
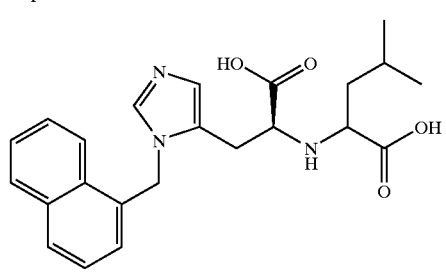
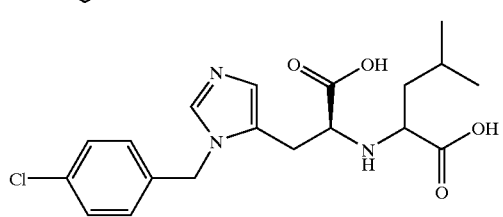
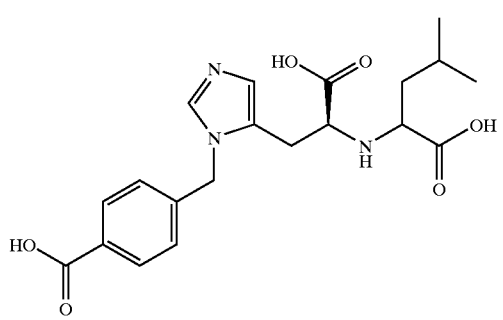
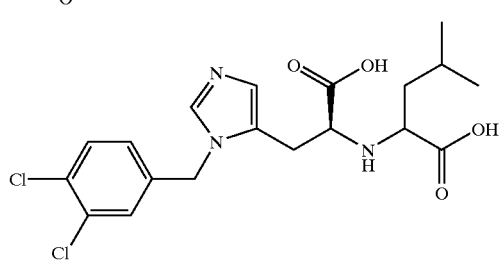
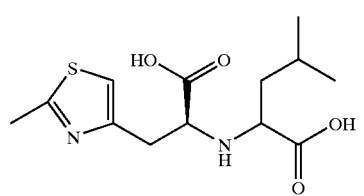
22
-continued
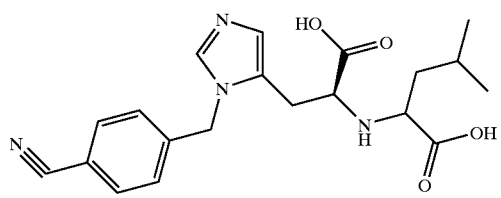
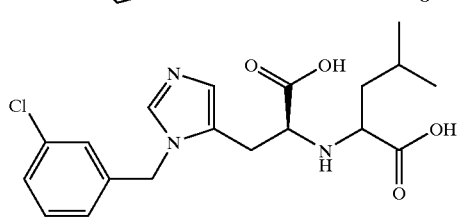
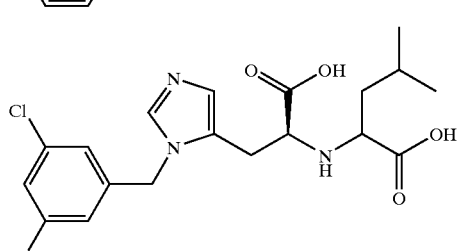
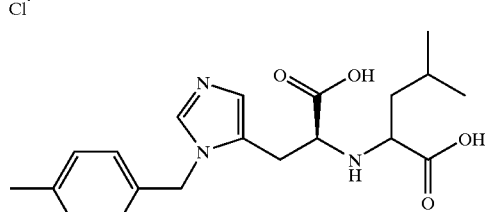
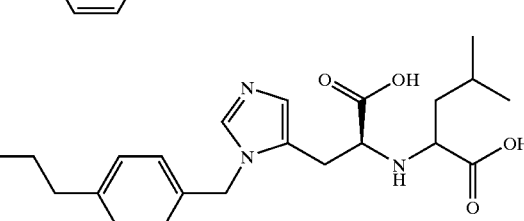
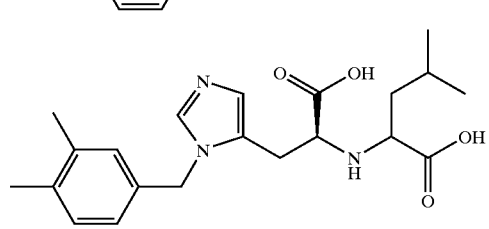
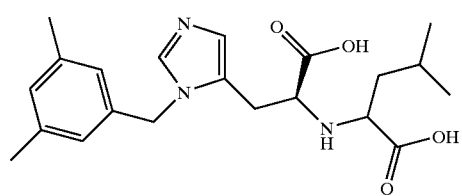

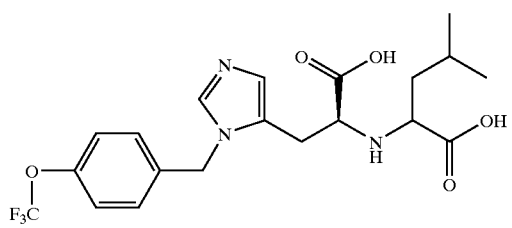
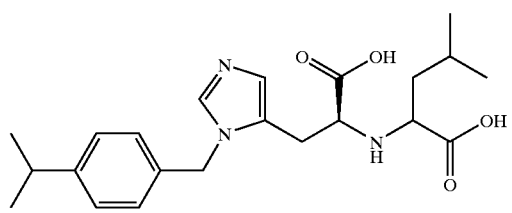
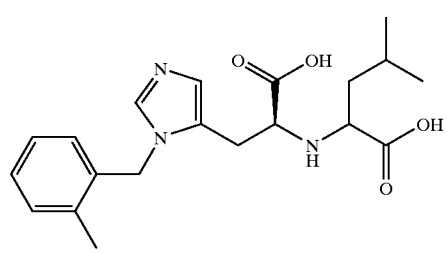
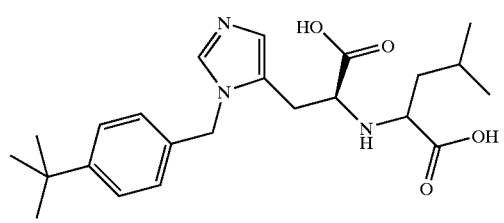
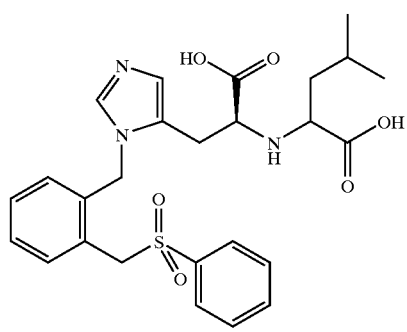
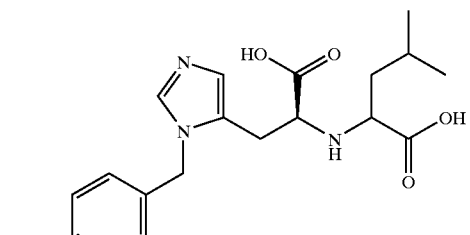
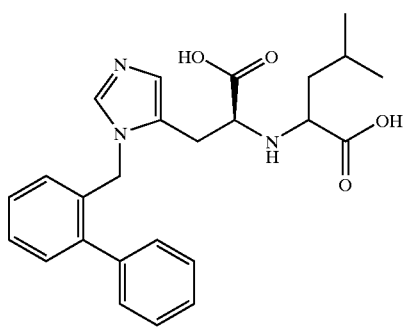
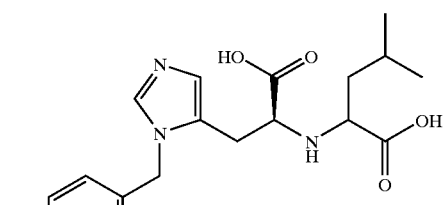
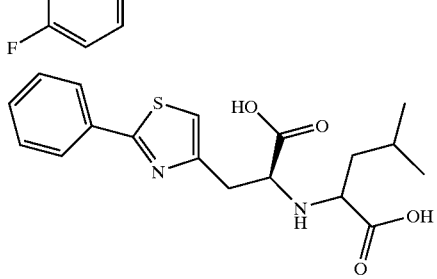
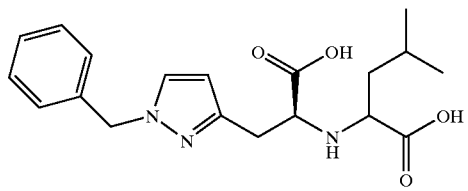
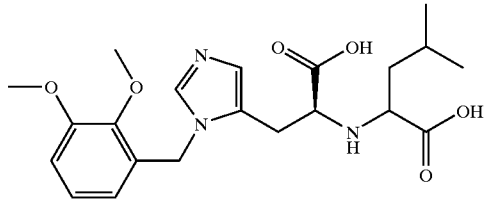
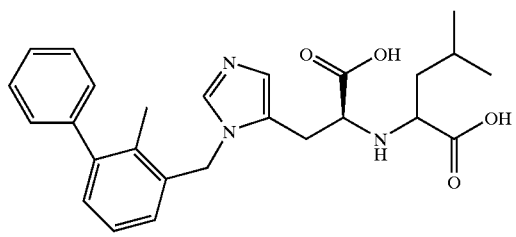
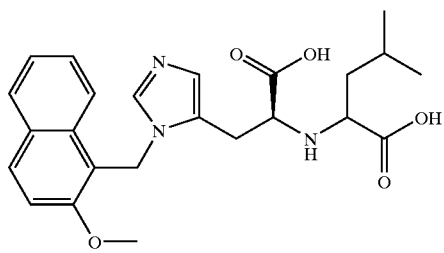

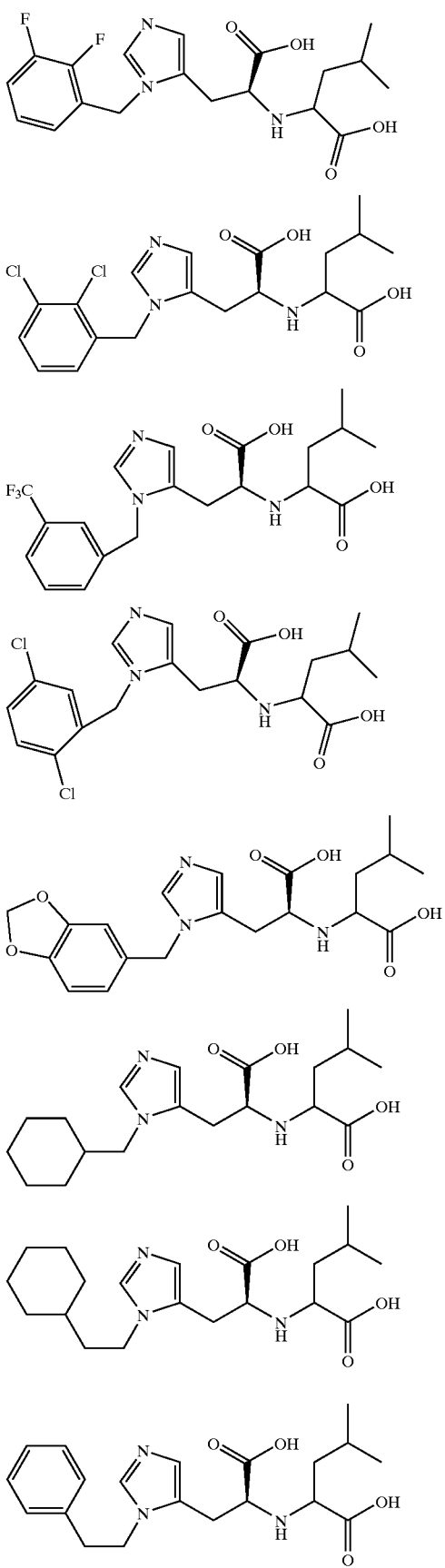
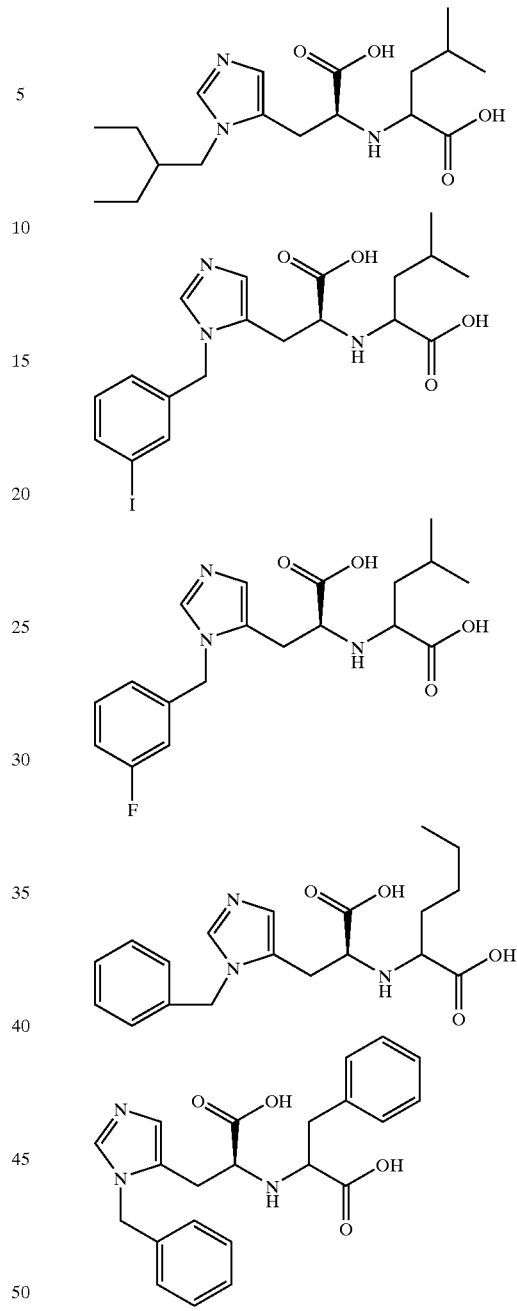

Other exemplary compounds are discussed in the Example section and Table 2.

The term "alkyl" includes saturated aliphatic groups, including straight-chain alkyl groups (e.g., methyl, ethyl, propyl, butyl, pentyl, hexyl, heptyl, octyl, nonyl. decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$–$C_6$ for straight chain, $C_3$–$C_6$ for branched chain), and more preferably 4 or fewer. Likewise, preferred cycloalkyls have from 3–8 carbon atoms in their ring structure, and more preferably have 5 or 6 carbons in the ring structure. The term $C_1$–$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$–$C_6$ for straight chain, $C_3$–$C_6$ for branched chain). Likewise, cycloalkenyl groups may have from 3–8 carbon atoms in their ring structure, and more preferably have 5 or 6 carbons in the ring structure. The term $C_2$–$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$–$C_6$ for straight chain, $C_3$–$C_6$ for branched chain). The term $C_2$–$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2–5 carbon atoms.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarboxy" includes compounds or moieties which contain a nitrogen atom which is bound to the carbon of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and "alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

The compounds of the invention can be synthesized by methods known to those of skill in the art from compounds which are commercially available. Scheme 1 depicts a general method of synthesizing compounds of the present invention, wherein Q is NH.

through treatment with the corresponding alcohol. The diastereomers prepared here can be separated by conventional means.

The thiol compounds of the invention, wherein Q is CHSH, can be synthesized by methods well known in the art. A sample synthesis is outlined below in Scheme 2.

Scheme 2

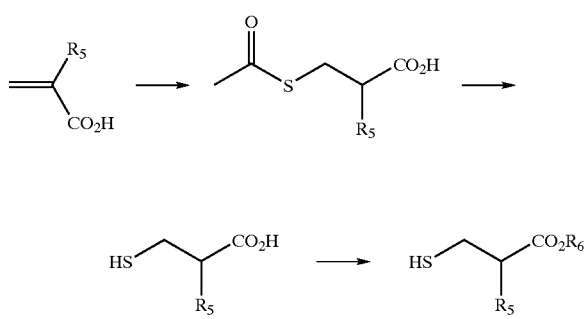

The thiol can be synthesized, for example, by heating thiolacetic acid with an appropriately substituted acrylic acid to form the thioester. The thioester can be hydrolyzed to the thiol by treatment with base. If desired, the ester can be formed by treating the acid compound with the appropriate alcohol to form the desired ester. One of skill in the art would be able to separate resulting enantiomers through conventional means such as, for example, chiral HPLC chromatography.

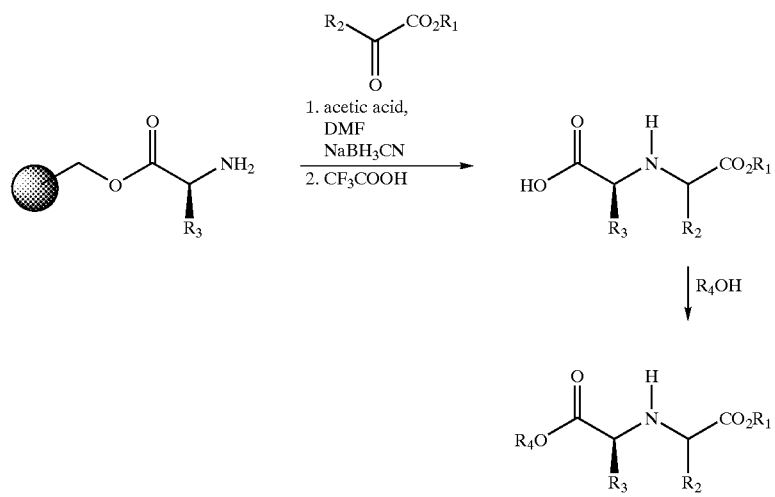

Scheme 1

Resin bound FMOC protected amino acids are commercially available from Novabiochem. The amino terminus can be deprotected by treatment with 20% piperidine in DMF for 30 minutes. The amine can then be treated with acetic acid in DMF and various commercially available α-ketoesters. The resulting Schiff base can then be treated with a hydride agent such as NaBH$_3$CN to be converted into the corresponding secondary amine. The acids can be removed from the resin through treatment with a strong acid, e.g., trifluoroacetic acid. The resulting acid can be esterified, if desired, Scheme 3

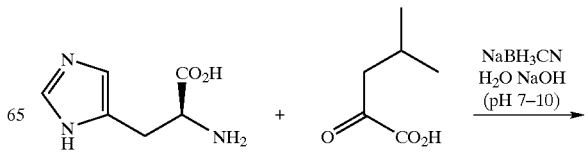

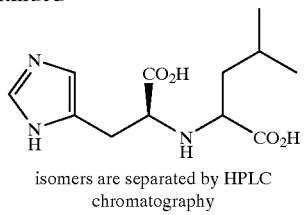

isomers are separated by HPLC chromatography

The imidazole compounds of the invention can be synthesized using the procedure outlined in Scheme 3. In a neutral to basic solution, the amine reacts with the carbonyl of the α-ketoacid to form the Schiff base, which is readily converted into the secondary amine, forming the product. Substituted imidazole compounds of the invention can be synthesized, for example, by treating α-protected histidine with a suitable halogenenated compound, such as benzyl bromide. The substituted histidine derivatives can then be used in place of histidine in the synthesis shown in Scheme 3.

Compounds of the invention can also be synthesized using the procedure outlined in Scheme 4. In Scheme 4, a phenyl ACE-2 inhibiting compound is synthesized by treating an ethyl ester with triflic anhydride and 2,6-lutidine in methylene chloride at −78° C. To this mixture, leucine methyl ester was added forming the secondary amine. The ester was then treated with aqueous base to form the resulting diacid. Further synthetic examples are given in the Example section.

aberrant levels of ACE-2 activity, and/or levels of ACE-2 substrate and/or ACE-2 metabolic products. ACE-2 associated states may include, for example, high blood pressure, high blood pressure related diseases and disorders, and, in particular, arterial hypertension. Other ACE-2 associated states include congestive heart failure (CHF).

Blood pressure refers to the pressure exerted by the blood upon the walls of the blood vessels, e.g., arteries, and is usually measured on the radial artery by means of a sphygmomanometer, and expressed in millimeters of mercury. The following ranges of blood pressure are usually used as a standard for normal versus abnormal blood pressure: a normal blood pressure corresponds to a diastolic blood pressure of less than 85 mm Hg; a high normal blood pressure corresponds to a diastolic blood pressure between 85 and 89 mm Hg; a mild hypertension corresponds to a diastolic blood pressure between 90–104 mm Hg; a moderate hypertension corresponds to a diastolic blood pressure between 105 and 114 mm Hg; and severe hypertension corresponds to a diastolic blood pressure higher than 115 mm Hg. Abnormal blood pressure can also be determined based on the systolic blood pressure (when the diastolic pressure is less than 90 mm Hg). Thus, a normal blood pressure corresponds to a systolic blood pressure of less than 140 mm Hg; a borderline systolic hypertension corresponds to a systolic blood pressure between 140 and 159 mm Hg; and isolated systolic hypertension corresponds to a systolic blood pressure higher than 160 mm Hg. This classification is borrowed from *Cecil: Essentials of Medicine*, Third Edition by Andreoli et al. W.B. Saunders Company (1993). A diagnosis of hypertension, also referred to herein as

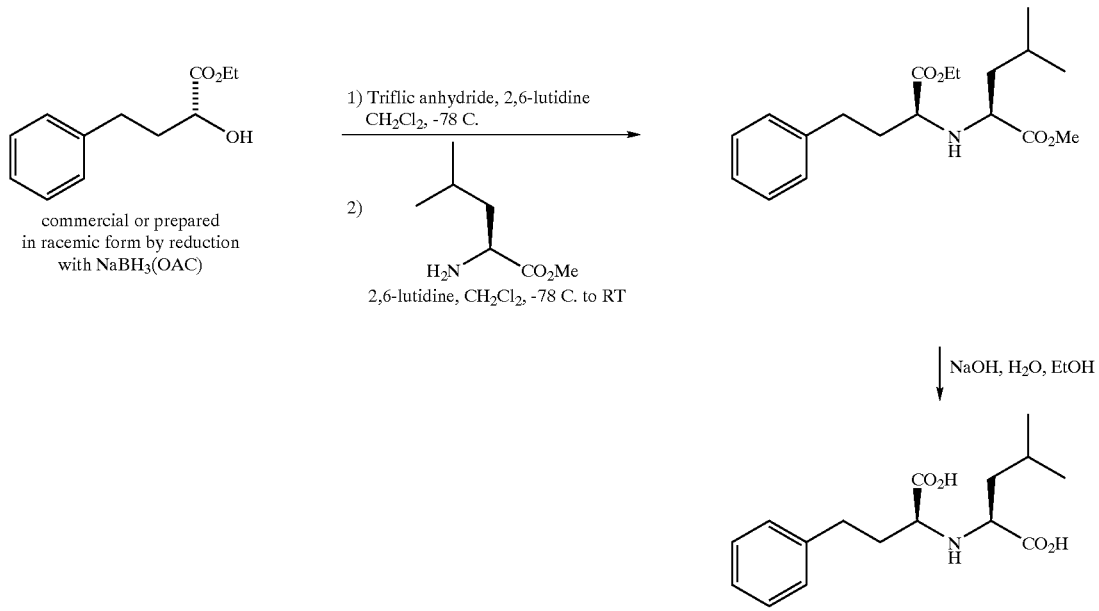

Scheme 4

The invention also pertains to a method of treating an ACE-2 associated state in a patient, by administering to the patient a therapeutically effective amount of an ACE-2 inhibiting compound, such that the ACE-2 associated state is treated.

The language "ACE-2 associated state" includes those states which are associated with ACE-2, ACE-2 substrates, or the products of its metabolic pathways. ACE-2 associated disorders also include disorders which are characterized by "abnormally high blood pressure", is usually made in an adult over 18 years of age if the average of two or more blood pressure measurements on at least two subsequent visits is 90 mm Hg or higher diastolic or 140 mm Hg systolic. Since children and pregnant women have a lower blood pressure, a blood pressure over 120/80 (i.e., 120 mm Hg systolic blood pressure/80 mm Hg diastolic blood pressure), is considered abnormal. Isolated systolic hypertension (ISH) refers to a condition in which the systolic blood pressure is greater than 160 mm Hg and the diastolic blood pressure is less than 85 mm Hg. ISH is associated with enhanced morbidity.

ACE-2 associated states also include other blood pressure related diseases or conditions, e.g., CHF (congestive heart failure), chronic heart failure, left ventricular hypertrophy, acute heart failure, myocardial infarction, and cardiomyopathy.

A preferred ACE-2 associated state is CHF. CHF is characterized by the inability of the left ventricle to maintain a normal blood pressure. This results in a baroflex-mediated reflex increase in sympathetic discharge, which stimulates the myocardium to beat faster and stronger, yet increases peripheral vasoconstriction so that the afterload rises and the load on the failing myocardium augments (Lionel H. Opie, Drugs for the Heart, Third Edition, W.B. Saunders Co., 1991). Excess adrenergic activity also results in enhanced activity of the renin-angiotensin system, further increasing peripheral vascular resistance and contributing to fluid retention (edema) by stimulation of the secretion of aldosterone. In addition, angiotensin promotes the release of vasopressin to contribute to abnormal volume regulation and hyponatremia in severe CHF. Overloading of the left ventricle also results in hypertrophy of the ventricular muscle, resulting in a decrease in its contractility, further contributing to the condition.

Previously it has been discovered that vasodilators such as ACE-inhibitors are efficient in treating CHF and reducing mortality. The present invention contemplates therapeutic methods and compositions which ACE-inhibiting compounds are administered to a patient concurrently or separately with ACE-2 modulating compounds. ACE inhibiting compounds are particularly preferred therapeutics for treating CHF since they are able to inhibit the deleterious neurohumoral viscious circle involving angiotensin-renin-aldosterone. Thus, it is believed that ACE-2 inhibiting compounds, which also modulate angiotensin hydrolysis, will also be useful for treating and preventing CHF.

ACE-2 associated states also include states which are associated with regulating cell proliferation, such as smooth cell proliferation. Smooth muscle cell proliferation in the intima of muscular arteries is a primary cause of vascular stenosis in atherosclerosis, after vascular surgery, and after coronary angioplasty. Several animal studies have indicated that the renin-angiotensin system plays an important role in this vascular response to injury. The stimulatory effect of angiotensin II on cell growth and replication in the cardiovascular system, which may result in myocardial hypertrophy and hypertrophy or hyperplasia of conduit and resistance vessels in certain subjects is mediated through angiotensin II receptors (subtype AT1) (Rosendorff C. *J. Am. Coll. Cardiol.* (1996)28: 803). The importance of ACE in atherosclerosis is further described, e.g., in Malik et al. *Am. Heart J*. (1997) 134:514. It has also been shown, that angiotensin caused myocyte hypertrophy and fibroblast proliferation associated with the induction of mRNA for several early response genes (c-fos, c-jun, jun B, Egr-1 and c-myc), angiotensinogen and transforming growth factor beta (TGFβ) (Rosendorff *J. Am. Coil. Cardiol.* (1996) 28: 803–12; Paquet et al. *J. Hypertens.* (1990) 8: 565–72).

Accordingly, in one embodiment, the invention pertains to methods for reducing or inhibiting smooth muscle cell proliferation, comprising administering to a subject an efficient amount of a composition by administering an ACE-2 inhibiting compound. ACE-2 inhibiting compounds may be administered systemically or locally, e.g., at a site of vascular injury.

Other examples of ACE-2 associated states include kidney diseases or disorders, e.g., renal failure. Angiotensin and ACEs are important in the development and for the maintenance of the functional and structural integrity of the adult kidney (see, e.g., Hilgers et al. *Semin. Nephrol.* (1997) 17:492). Chronic renal disease evolves to end-stage renal failure through events, including enhanced intraglomerular pressure and plasma protein ultrafiltration, mediated at least in part by angiotensin II. It has been reported that ACE inhibitors reduce intracapillary pressure and ameliorate glomerular size-selective function (see, e.g., Ruggenenti and Remuzzi *Curr. Opin. Nephrol. Hypertens.* (1997) 6:489). Thus, based at least in part on the fact that ACE-2 is expressed in kidney and is homologous to ACE, ACE-2 modulating compounds may be used for treating and preventing renal diseases or disorders, either alone or in combination with known ACE inhibitors.

The language "in combination with" another therapeutic agent includes co-administration of the ACE-2 inhibitor and the other therapeutic agent, administration of the ACE-2 inhibitor first, followed by the other therapeutic agent and administration of the other therapeutic agent first, followed by the ACE-2 inhibitor. The other therapeutic agent may be any agent which is known in the art to treat, prevent, or reduce the symptoms of a ACE-2 associated state. Furthermore, the other therapeutic agent may be any agent of benefit to the patient when administered in combination with the administration of an ACE-2 inhibiting compound. Furthermore, ACE-2 compounds can also be administered in combination with other known therapies for ACE-2 associated states. Other methods of treating ACE-2 associated states, e.g., cardiovascular disorders, renal disorders, inflammation, etc. are known to those skilled in the art. In one embodiment, the other therapeutic agent may be an ACE inhibitor.

ACE-2 associated states also include various other hyperadrenergic states, such as acute myocardial infarction (AMI) and some ventricular arrthythmias. The invention further provides methods for treating kinetensin associated conditions. As described herein, ACE-2 cleaves the C-terminal amino acid (leucine) from kinetensin. Kinetensin is a nine amino acid peptide having SEQ ID NO: 23 (see U.S. Ser. No. 09/163,648) which has been reported to induce a dose-dependent release of histamine from mast cells, as well as induce a dose-dependent increase in vascular permeability when injected intradermally (Sydbom et al. *Agents Actions* (1989) 27: 68) into rats. Accordingly, modulating the plasma and/or tissue level of kinetensin, such as by modulating the hydrolysis of the C-terminal amino acid from kinetensin, should be useful for treating conditions that are caused by, or contributed to by, an abnormal kinetensin level. Such conditions include those caused by, or contributed to by, an abnormal histamine release from mast cells and/or by an abnormal vascular permeability. Since excessive histamine release is associated with local or systemic allergic reactions, including exzema, asthma, anaphylactic shock, these conditions are included in the definition of "ACE-2 associated states."

Other examples of ACE-2 associated states include, for example, SIRS (Systemic Inflammatory Response Syndromes), sepsis, polytrauma, inflammatory bowel disease, acute and chronic pain, bone destruction in rheumatoid and osteo arthritis and periodontal disease, dysmenorrhea, premature labor, brain edema following focal injury, diffuse axonal injury, stroke, reperfusion injury and cerebral vasospasm after subarachnoid hemorrhage, allergic disorders including asthma, adult respiratory distress syndrome, wound healing and scar formation.

Based at least on the presence of ACE-2 in testis, ACE-2 associated states may also include infertility or other disorders relating to gamete maturation. In addition, ACE-2 associated states may also include cognitive disorders, and disorders associated with bradykinin and des-Arg bradykinin.

The term "treating" includes curing as well as ameliorating at least one symptom of the state, disease or disorder.

The term "administering" includes routes of administration which allow the ACE-2 inhibiting compound to perform its intended function, e.g. inhibiting the function of ACE-2 and/or treating an ACE-2 associated state. Examples of routes of administration which can be used include parental injection (e.g., subcutaneous, intravenous, and intramuscular), intraperitoneal injection, oral, inhalation, and transdermal. The injection can be bolus injections or can be continuous infusion. Depending on the route of administration, the ACE-2 inhibiting compound can be coated with or disposed in a selected material to protect it from natural conditions which may detrimentally effect its ability to perform its intended function. The ACE-2 inhibiting compound can be administered alone or with a pharmaceutically acceptable carrier. Further, the ACE-2 inhibiting compound can be administered as a mixture of ACE-2 inhibiting compounds, which also can be coadministered with a pharmaceutically acceptable carrier. The ACE-2 inhibiting compound can be administered prior to the onset of an ACE-2 mediated state, or after the onset of a ACE-2 mediated state. The ACE-2 inhibiting compound also can be administered as a prodrug which is converted to another form in vivo.

The language "therapeutically effective amount" of the compound is that amount necessary or sufficient to treat or prevent an ACE-2 associated state, e.g. prevent the various morphological and somatic symptoms of a ACE-2 associated state. The effective amount can vary depending on such factors as the size and weight of the subject, the type of illness, or the particular ACE-2 inhibiting compound. For example, the choice of the ACE-2 inhibiting compound can affect what constitutes an "effective amount". One of ordinary skill in the art would be able to study the aforementioned factors and make the determination regarding the effective amount of the ACE-2 inhibiting compound without undue experimentation.

The effective amount can be determined through consideration of the toxicity and therapeutic efficacy of the ACE-2 inhibiting compounds by standard pharmaceutical procedures in cell cultures or experimental animals, e.g., for determining the $LD_{50}$ (The Dose Lethal To 50% Of The Population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The invention also relates to a pharmaceutical composition containing a pharmaceutically acceptable carrier and an effective amount ACE-2 inhibiting compound to treat an ACE-2 associated state.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can performs its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, certain embodiments of the present compounds can contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

While it is possible for a compound of the present invention to be administered alone, it is preferable to administer the compound as a pharmaceutical composition.

The regimen of administration can affect what constitutes an effective amount. The ACE-2 inhibiting can be administered to the subject either prior to or after the onset of an ACE-2 associated state. Further, several divided dosages, as well as staggered dosages, can be administered daily or sequentially, or the, dose can be continuously infused, or can be a bolus injection. Further, the dosages of the ACE-2 inhibiting compound(s) can be proportionally increased or decreased as indicated by the exigencies of the therapeutic or prophylactic situation.

The invention also involves a method for treating an ACE-2 associated state in a patient, by administering to said patient an effective amount of an ACE-2 inhibiting compound in combination with an effective amount of an ACE inhibitor. Preferred ACE-2 associated states include, for example, congestive heart failure, blood pressure disorders, cell proliferation disorders, kidney disorders, kinetensin associated disorders, inflammation associated disorders, or allergic disorders. Preferably the ACE-2 associated state is a blood pressure related disorder.

The term "ACE inhibitor" is intended to include compounds which reduce the activity of ACE. Examples of ACE inhibitors are well known in the art. Preferred ACE inhibitors, include, for example, CAPTOPRIL, ENALAPRIL, FOSINOPRIL, LINSINOPRIL, and RAMIPRIL.

The language "in combination with" ACE inhibitors includes simultaneous administration of the ACE-2 inhibitor and the ACE inhibitor, administration of the ACE-2 inhibitor first, followed by the ACE inhibitor and administration of the ACE inhibitor first, followed by the ACE-2 inhibitor. Any of the therapeutically useful ACE inhibitors known in the art can be used in the methods of the invention.

The invention further pertains to a method for inhibiting the hydrolysis of an ACE-2 target peptide by contacting ACE-2 with an ACE-2 inhibiting compound and an ACE-2 target peptide, thereby inhibiting the hydrolysis of the ACE-2 target peptide.

The term "target peptide" is intended to include compounds which are capable of being hydrolyzed by ACE-2. Examples of target peptides include angiotensin, kinin, and kinetensin.

This invention is further illustrated by the following examples which should not be construed as limiting. The contents of all references and published patents and patent applications cited throughout the application are hereby incorporated by reference.

EXEMPLIFICATION OF THE INVENTION

EXAMPLE 1

Production of ACE and ACE-2 Polypeptides

ACE and ACE-2 polypeptides were produced in CHO cells as follows. Full length ACE-2 expression vector (pFLA-2) was generated by ligating an EcroRI/Afl III fragment of a 5' RACE clone (cchr002) and an Afl III/Not I fragment of the original library clone into the EcoRI/Not I sites of pcDNA3.1 (Invitrogen). An expression vector for secreted ACE-2 (pMD37) was generated by subcloning into pACE-2 a small PCR fragment which has a stop codon inserted after the serine immediately preceding the transmembrane domain. Testicular ACE cDNA was obtained from James Riordan and was subcloned into pcDNA3.1 for expression. For the transfections, CHO K1 cells, which are maintained in serum-free Ultra CHO medium (Biowhittaker) at 37° C. in a humidified 5% $CO_2$ incubator, were seeded at $1\times10^6$ cells/10 cm dish on day 0 and transfected with lipofectamine on day 1 as per manufacturers' instructions. Briefly, 10 $\mu$g of DNA were combined with 40 $\mu$l of lipofectamine in Opti-MEM medium and the mixture was incubated on the cells for 5–6 hours. Ultra CHO medium was then added to the cells and they were incubated overnight at 37° C. On day 2, the medium was changed and on day 4 the media were collected. For the examples below, the conditioned media containing the secreted ACE-2 protein was concentrated in Centriplus 30 concentrators (Amicon).

EXAMPLE 2

Purification of ACE-2

The following protocol is an example of a protocol that was used for the purification of ACE-2 for use in the subsequent examples.

ACE-2 CHOK1 cell supernatant was dialyzed into 50 mM BisTrisPropane/Tris HCl overnight at pH 6.5 and 4° C. The dialyzed supernatant was then filtered using a 0.2 $\mu$m filter unit. The filtrate was then loaded on to a MonoQ anion exchange column and eluted with a 0–250 mM NaCl gradient. The fractions containing ACE-2 (as determined by Coumassie Blue stained SDS-Page gel or Western blot) were pooled and 1M $Am_2SO_4$ was added until the final concentration was about 1M. The fractions were then centrifuged, and the supernatant was retained. The supernatant was then loaded on to a phenyl superose hydrophobic column and eluted with 1M–0.5M $Am_2SO_4$ reverse gradient in 100 mM NaPi at pH 7. The ACE-2 containing fractions were then pooled and dialyzed into 20 mM HEPES/15 mM NaCl at pH 7 at 4° C. overnight. The dialyzed fractions were then filtered for a final time through a 0.2 $\mu$m syringe.

EXAMPLE 3

Synthesis of Compounds D and E

Scheme 5

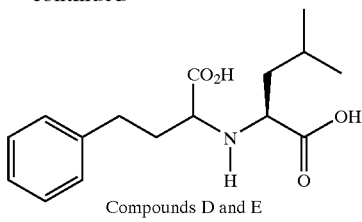

Compounds D and E

Fmoc-Leu-Wang resin (commercially available from Novabiochem, loading 0.8 mmol/g, 2.61 g, 2.09 mmol) was treated with 20% piperidine in DMF (ca. 100 mL) for thirty minutes. The resin was then filtered and washed well with DMF, THF, $CH_2Cl_2$, and methanol. The resin was then suspended in 52 mL of DMF, and acetic acid (6.5 mL) and ethyl 2-oxo-4-phenylbutyrate (9.8 mL, 52.20 mmol) were added. This slurry was shaken for 10 minutes and the $NaBH_3CN$ (5.26 g, 83.60 mmol) was added which resulted in the evolution of heat and gas (Blackburn et al. *Biorg. and Med. Chem. Lett.* (1997) 7(7):823–828). The reaction mixture was sealed and shaken for two days. The resin was then separated from the reaction mixture by filtration and was subsequently washed well with methanol, $CH_2Cl_2$, 10% acetic acid in THF, THF, DMF and methanol. The resin was then suspended in ca. 10 mL of 50% trifluoroacetic acid in $CH_2Cl_2$ and shaken for thirty minutes. The resin was separated from the reaction mixture by filtration, and the resin was again treated with 100 mL of 50% trifluoroacetic acid in $CH_2Cl_2$ for 30 minutes. After filtration, the resin was washed well with 50 mL 50% trifluoroacetic acid in $CH_2Cl_2$. Combined filtrates were concentrated to give a tan oil. Purification of this oil by column chromatography ($SiO_2$, 7.5:2:0.5, $CH_2Cl_2$: EtOAc:methanol with 0.1% acetic acid) provided 2 sets of material—172 mg of desired product and 192 mg of desired product contaminated with a material of higher Rf (desired product Rf: 0.45, contaminant Rf: 0.55 in 7:2:1 $CH_2Cl_2$:EtOAc:methanol with 0.1% acetic acid.) Both sets of material were clean by $^1H$ NMR. The 172 mg of desired material was further purified by HPLC (C18 column, gradient elution starting with 100% of 95% $H_2O$, 1% acetonitrile, 0.1% formic acid, ending with 60% of 95% $H_2O$, 1% acetonitrile, 0.1% formic acid and 40% of 95% acetonitrile, 0.5% $H_2O$, 0.1% formic acid 30 mL/min.). This HPLC method separated the 2 diastereomers of the monoester to give 37 mg of a white powder (retention time 11.5 minutes,) and 58 mg of a white powder (retention time 13.2 minutes,). Both compounds are clean and single isomers by $^1H$ NMR.

A round bottomed flask containing 18 mg of the earlier eluted monoester was dissolved in 1 mL of 95% ethanol, and 400 µL of aqueous 1N NaOH solution was added. The reaction mixture was stirred for eighteen hours. The reaction mixture was then dried in vacuo and redissolved in water. A 2N HCl solution was added dropwise until a pH of 1 was reached and a white precipitate had appeared. The white precipitate was triturated with water and ethyl acetate and then concentrated under vacuum to give 12 mg of white solid, Compound D).

A round-bottomed flask containing 18 mg of the later eluted monoester was dissolved in 1 mL of 95% ethanol and 200 µL of aqueous 1N NaOH solution was added. The reaction mixture was stirred for 18 hours and was not complete by TLC. Another 100 µL of aqueous NaOH was added, and the reaction mixture was stirred for 48 additional hours. The reaction mixture was then dried in vacuo and redissolved in water. 1N HCl solution was added until a pH of 1 was reached and a white precipitate had appeared. Ethyl acetate was added and the two phase mixture was extracted twice with ethyl acetate (containing 2.5% THF). The combined organic phases were extracted with brine, dried over $Na_2SO_4$, filtered and concentrated to give a white solid (Compound E).

EXAMPLE 4

Synthesis of Compound G

Scheme 6

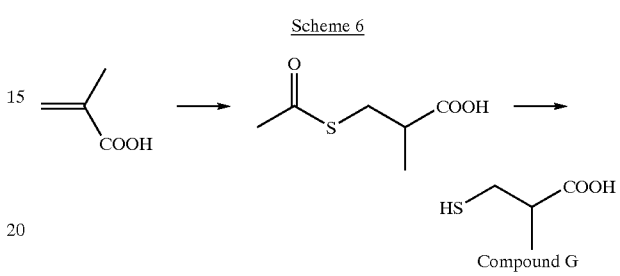

Compound G

Compound G was synthesized by heating thiolacetic acid with methacrylic acid to form the thioester (Neustadt et al., *J. Med. Chem.* (1994) 37:2461–2476). The thioester was then treated with 1N NaOH (aq) and MeOH and hydrolyzed to the thiol (Compound G).

EXAMPLE 5

Synthesis of Compounds EA and EB

Propargyl glycine (1 equiv) was dissolved in a 50:50 mixture of benzene and methanol, and a solution of TMS-diazomethane in hexane (2M, 1.5 equiv) was added to the reaction mixture dropwise. This reaction mixture was stirred at room temperature for 6 hours, and then it was concentrated. The residue was dissolved in dichloromethane, and the resulting solution was washed with saturated $NaHCO_3$ solution, dried over $MgSO_4$, filtered, and concentrated to give the desired ester as an oil.

Ethyl 4-phenyl-2-hydroxy-butyrate (prepared in racemic form from the $LiAlH_4$ reduction of ethyl 4-phenyl-2-oxo-butyrate) was dissolved in dichloromethane, and the solution was cooled to −78° C. Trifluoromethane sulfonic anhydride (1.05 equiv) and 2,6-lutidine (1.1 equiv) were then added dropwise. The reaction mixture was stirred at −78° C. for 1 hour and then allowed to warm to room temperature. Water was added to the reaction mixture, and the organic phase was separated, washed with brine, dried, filtered, and concentrated to give a yellow oil. This oil was purified by column chromatography (silica gel, 10% ethyl acetate/hexane) to give the desired triflate as an oil (Walker, *Tetrahedron*, (1997) 37:2461–2476).

The triflate prepared above was dissolved in dichloromethane, and the solution was cooled to −78° C. 2,6-Lutidine (1.1 equiv) was added and then a solution of the methyl ester of propargyl glycine (prepared above) in dichloromethane was added dropwise. The reaction mixture was stirred at −78° C. for 1 hour and then allowed to warm to room temperature and stirred overnight. Water was added to the reaction mixture, and the organic phase was separated, washed with water and brine, dried, filtered, and concentrated to give a yellow oil. This oil was purified by column chromatography (Biotage Quad 3, silica gel, 15% ethyl acetate/hexane) to give the desired secondary amine as an oil.

The secondary amine prepared above was dissolved in degassed DMF, and 2-bromopyridine (1.1 equiv) was added to this solution. Palladium tetrakistriphenylphosphine (0.05 equiv), triethyl amine (2.0 equiv), and copper iodide (0.2 equiv) were added sequentially. The reaction mixture was protected from the light and stirred for 3 hours. Water was added, and this mixture was extracted three times with ethyl acetate. Combined organic phases were washed with water and brine, dried, filtered, and concentrated to give a brown oil. This oil was purified by column chromatography (silica gel, 30% ethyl acetate/hexane) to give a yellow semi-solid. Further purification by column chromatography (silica gel, 50% ethyl acetate/hexane) gave the desired alkynylpyridine diester as a colorless oil (Wallace et al. *J. Med. Chem.* (1998) 41:1513–1523).

The diester prepared above was dissolved in ethanol, and a 1 N solution of NaOH (8.0 equiv) was added dropwise. The solution was stirred at room temperature for 1 hour. The reaction mixture was concentrated, and the residue was taken up in water. The solution was acidified to pH 1 with 2 N HCl solution and then concentrated to give a white solid. This solid was dissolved in water and purified by absorbing on to DOWEX resin (cationic, prewashed) and eluting first with water and then 2% pyridine/water to give a yellow solid upon concentration of the basic fractions. Further purification of this material by HPLC provided two diacids (EA and EB).

EXAMPLE 6

Synthesis of Compounds EZ and FA

A suspension of Boc-His-OMe (0.92 mol, 25 g) in toluene (300 mL 0.3 M) and triethylamine (1.1 mol, 15.5 mL) was treated with trityl chloride (28.5 g, 1.02 mol). The reaction was heated at 60° C. for 24 hours (Anthony, N.J., et al. *J. Med. Chem.*, (1999) 42:3356–x68; Kitajima, Y., et al. *Bull. Chem. Soc. Japan*, (982) 55:3870–3872). The reaction mixture was diluted with ethyl acetate and washed with saturated $NaHCO_3$ (2×) and brine (1×). A brown oil was obtained after drying ($MgSO_4$) and concentration in vacuo. Trituration from ether, hexane and methanol resulted in 7.6 (80%) of the trityl protected histidine derivative as a white solid.

The trityl protected histidine derivative (5.0 g, 9.77 mmol) was suspended in anhydrous MeCN (10 mL, 1M) under a $N_2$ atmosphere and gently heated to 35° C. at which temperature the mixture became homogeneous. Benzyl bromide (9.77 mmol, 1.16 mL) was then added and the reaction temperature was increased to 55° C. After 15 hours, the reaction mixture was concentrated completely and redissolved in MeOH (60 mL, 0.16 M). This solution was refluxed for 1 hour then concentrated completely. The solid residue was dissolved in $CH_2Cl_2$ and washed with saturated $NaCO_3$ (2×) and brine (1×) and dried over $MgSO_4$. The crude brown oil was purified by column chromatography (0–2% MeOH in $CH_2Cl_2$) to yield 2.1 g (58%) of the N-3 benzyl histidine derivative (N-3 alkylation was confirmed by ROESY NMR).

The N-3 benzyl histidine derivative (7.8 g, 22 mmol) was dissolved in 4N HCl in dioxane (85 mL) and reacted for 1 hour then concentrated completely. The resulting white solid was dissolved in 1 N NaOH (130 mL) and the pH was adjusted to 9–10 using 6 N HCl. α-Ketoisocaproic acid sodium salt (16.6 g, 109 mmol) was then added. After 15–30 minutes, $NaBH_3CN$ (4.1 g, 66 mmol) was added. After 48 hours, the pH was adjusted to 3 using 6 N HCl and the reaction mixture was filtered through a pad of Dowex (50WX2-200) eluting with water then $NH_4OH$. The product fractions were combined and purified to give EZ and FA.

EXAMPLE 7

Purification of EZ and FA

The reaction mixture (21.4 g) containing salts, unreacted starting materials and diastereomers (EZ and FA) was dissolved in water (50 mL) and passed through a HP-20 column to remove the salts. The column was eluted with distilled water (500 mL) and finally washed with methanol (500 mL). Removal of the solvent yielded a residue (8.5 g) that was chromatographed over a column of RP-18 silica gel (MeOH:$H_2O$; 60:40). Several fractions were collected and monitored by TLC. Fractions containing diastereomers were pooled (3.2 g) and further purified by preparative HPLC (Varian, C-18 column, $H_2O$:ACN:0.1 HCOOH) to afford pure diastereomers EZ (1.02 g) and FA (1.78 g) as white colorless solids. The more active diastereomer (EZ) was passed through a column of Sephadex LH-20 to remove formate impurities. The product fractions were pooled to yield EZ as a colorless powder (0.93 g) that crystallized from a mixture of ethanol and methanol as colorless needles.

EXAMPLE 8

Spectroscopy Data for Selected Compounds

Compound EN $^1$H-NMR ($D_2O$): δ 8.33 (s, 1H); 7.41–7.48 (m, 5H); 7.26 (s, 1 H); 5.68 (ABq, 2H, J=11.5 Hz, $δ_A$=5.69, $δ_B$=5.67); 4.71 (s, 2H); 3.84 (dd, 1H, J=7.3, 6.4 Hz); 3.57 (t, 1H, J=7.6, 6.3 Hz); 3.37–3.45 (m, 2H); 1.76–1.80 (m, 1H); 1.54–1.63 (m, 2H); 0.93 (d, 6H, J=6.6 Hz).

Compound EZ $^1$H NMR ($CD_3OD$) δ 8.58 (s, 1H), 7.48 (s, 1H), 7.32–7.45 (m, 3H), 7.24–7.31 (m, 2H), 3.72 (t, 1H, J=6.8 Hz), 3.60 (dd, 1H, J=7.6, 6.1 Hz), 3.13–3.21 (m, 2H), 1.88–1.97 (m, 1H), 1.64–1.78 (m, 2H), 0.98 (d, 6H, J=6.5 Hz), (8.12, s formic acid, 0.1 eq); N-3 alkylation confirmed by ROESY NMR.

Compound GA $^1$H NMR ($CD_3OD$) δ 8.19 (bd, 1H, J=7.9 Hz), 8.06 (bs, 1H), 7.91 (bs, 1H), 7.63 (t, 1H, J=7.8 Hz), 7.57 (bd, 1H; J=7.8 Hz), 7.17 (bs, 1H), 5.46 (s, 2H), 3.63 (t, 1H, J=6.5 Hz), 3.55 (t, 1H, J=6.9 Hz), 3.10–3.16 (m, 2H), 1.89–1.94 (m, 1H), 1.70 (t, 2H, J=6.8 Hz), 0.97 (d, 6H, J=6.5 Hz), (1.97, s, acetic acid, 0.6 eq).

Compound GM $^1$H NMR ($CD_3OD$) δ 8.28 (s, 1H); 7.39–7.32 (m, 3H); 7.27 (s, 1H); 7.16–7.14 (m, 1H); 5.36 (s, 2H); 3.69 (t, 1H, J=6 Hz); 3.57 (t, 1H, J=6 Hz); 3.16–3.13 (m, 2H); 1.99–1.86 (m, 1H); 1.71–1.65 (m, 2H); and 0.96 (d, 6H, J=6 Hz).

Compound HE $^1$H NMR ($CD_3OD$) δ 8.37 (s, 1H); 7.42 (t, 1H, J=1.8 Hz); 7.36 (s, 1H); 7.21 (d, 2H, J=1.8 Hz); 5.37 (s, 2H); 3.70 (t, 1H, J=6 Hz); 3.59 (dd, 1H); 3.15–3.12 (m, 2H); 1.98–1.85 (m, 1H); 1.70–1.64 (m, 2H); and 0.96 (d, 6H, J=6 Hz).

Compound HO $^1$H NMR ($CD_3OD$) δ 8.48 (s, 1H) 7.42–7.39 (m, 3H); 7.34 (s, 1H); 7.19–7.14 (m, 1H); 5.40 (s, 2H); 3.61–3.51 (m, 2H); 3.27 (d, 2H, J=6 Hz); 2.38 (s, 3H); 1.97–1.77 (m, 1H); 1.74–1.69 (m, 2H); and 0.99–0.96 (m, 6H).

Compound HQ $^1$H NMR ($CD_3OD$) δ 8.47 (s, 1H); 7.41 (s, 1H); 7.19 (s, 1H); 6.99 (s, 2H); 5.36 (s, 2H); 3.63 (t, 1H, J=9 Hz); 3.53 (t, 1H, J=6 Hz); 3.27 (d, 2H, J=9 Hz); 2.35 (s, 6H); 1.83–1.77 (m, 1H); 1.71–1.68 (m, 2H); and 0.98 (d, 6H).

EXAMPLE 9

ACE-2 Competitive Substrate Assay (ACS Assay)

A stock solution of ACE-2 in 10 mM HEPES (Sigma), 15 nM NaCl (Sigma) was stored as aliquots at −70° C.

Mass spectroscopy determined ACE-2 to be a carboxypeptidase that accepts a variety of P1' amino acids with a free carboxylic acid group (FIGS. 1, 2, and 3). Mass spectroscopy data for the ACE-2 hydrolysis of Angiotensin I (1–10) to Angiotensin I (1–9) are shown respectively in FIGS. 1A and 1B. FIG. 1A shows that in a sample with out ACE-2, Angiotensin I is not hydrolyzed. FIG. 1B shows that when treated with ACE-2, Angiotensin I (1–10) is converted to Angiotensin I (1–9). Similarly. FIG. 2 shows that ACE-2 hydrolyzes Neurotensin (1–13) (top) to Neurotensin (1–12) (bottom). The mass spectroscopy data for des-Arg bradykinin (1–8) to des-Arg bradykinin (1–7) is shown in FIGS. 3A (no ACE-2) and FIG. 3B (ACE-2), respectively.

ACE-2 enzymatic activity was assayed in microtitre plates by the following procedure. The ACE-2 assay buffer used contained 50 mM MES (Boehringer-Mannheim), 300 mM NaCl (Sigma) and 0.01% Brij-35 (Pierce Chemical Co.) at pH 6.5.

A 50 µL reaction mixture was prepared containing 25 µL of 1 nM ACE-2 in assay buffer, 20 µL of 125 µM substrate (see below) in assay buffer and 5 µl control solvent or test compound. Reactions were mixed and incubated at 25° C. Enzymatic cleavage of the substrate is marked by a fluorescence change (excitation at 328 nm, emission at 393 nm). Determination of ACE-2 enzymatic activity was found to be possible when fluorescent readings of the reactions were measured at excitation 320 nm and emission 405 nm using a BMG LabTechnologies PolarStar Plate Reader.

Caspase 1 substrate (Bachem M-2195, Mca-Tyr-Val-Ala-Asp-Ala-Pro-(Dnp)Lys-OH) (SEQ ID NO. 1) was tested as a synthetic substrate for ACE-2. Mass spectroscopy data analysis also showed that ACE-2 hydrolysed this substance between the P1 proline and P1' (DNP)Lys. Substrate optimization was achieved by the custom synthesis of Mca-Ala-Pro-(Dnp)Lys-OH (AnaSpec MIPH1). The results from the substrate optimization are shown in Table 1.

TABLE 1

| Substrate | $K_m$ (µM) | $k_{cat}/K_m$ ($M^{-1}s^{-1}$) | Fluorescence Units/mol |
|---|---|---|---|
| Bachem, M-2195 | 130 | 42,000 | 600 |
| AnaSpec MIPH-1 | 340 | 230,000 | 2880 |

ACE (Sigma, A2580) enzymatic activity was assayed in microtiter plates using the following protocol. ACE assay buffer was made from 50 mM HEPES (Sigma), 300 mM sodium chloride (Sigma), and 0.01% Brij-35 (Pierce Chemical Co) at pH 7.5.

A 50 µl reaction mixture was prepared containing 25 µl of 2 nM ACE in ACE assay buffer, 20 µl of 125 µM substrate, Abz-Gly-paranitroPhe-Pro-OH (Bachem M1100) in ACE assay buffer, and 5 µl control solvent or the test compound. Reactions were mixed and incubated at 25° C. Enzymatic cleavage of the substrate is marked by a fluorescence change (excitation 330 nm, emission 415 nm). Determination of ACE enzymatic activity was found to be possible when fluorescent readings of the reactions were measured at excitation 320 nm and emission at 405 nm using a BMG LabTechnologies PolarStar Plate Reader (Germany).

Carboxypeptidase A activity was measured using a literature assay (Holmquist and Riordan, "Carboxypeptidase A," *Methods of Enzymatic Analysis* (1984) p. 44–60). The assay was adapted to a 96 well format by adjusting to a 300 µL assay volume and using ultra-thin bottom plates (Costar/Corning) read at 328 nm. The assay was stopped using EDTA.

The activity of the test compounds was investigated using the procedure outlined above. The compounds were tested in 5% DMSO. Enzyme activity was measured at 12 compound concentrations. The $K_i$ was calculated by using $K_i=K_{iapp}/(1+[S]/K_m)$. The results are tabulated in Table 2.

In Table 2, the following key is used for the $K_i$'s:

| | ACE-2 Activity (Rat and Human) | | ACE Activity | | Carboxypeptidase A Activity |
|---|---|---|---|---|---|
| Some Inhibition | * | >10 µM | *** | >50 µM | *** | >50 µM |
| Good Inhibition | ** | 1–10 µM | ** | 10–50 µM | ** | 10–50 µM |
| Very Good Inhibition | *** | <1 µM | * | <10 µM | * | <10 µM |

Binding curves for Compound G is depicted in FIG. 4. The binding curve shows that Compound G selectively inhibits the activity of ACE-2 as compared with ACE.

Figure 5:
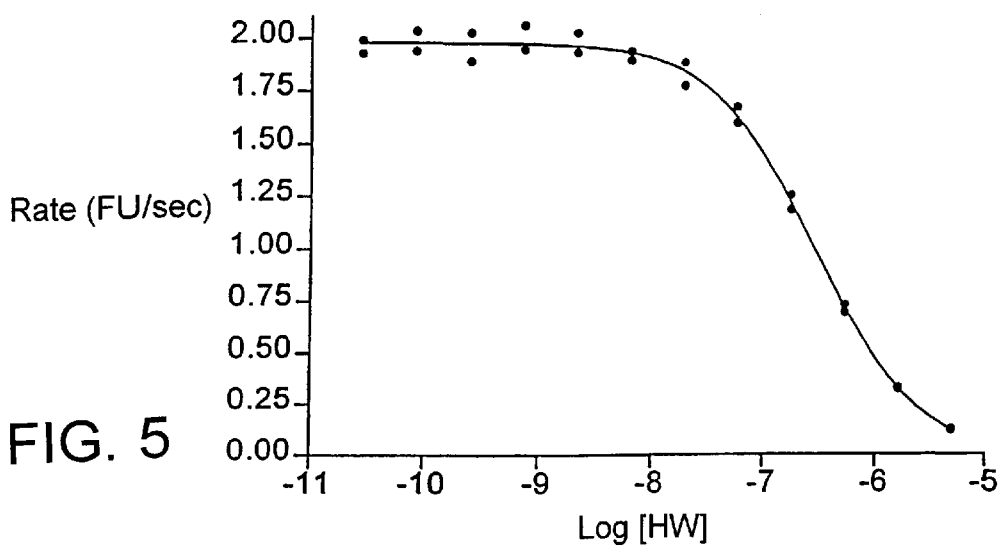
FIG. 5 is a graph depicting the inhibition of human ACE-2 when treated with Compound HW.
Figure 6:
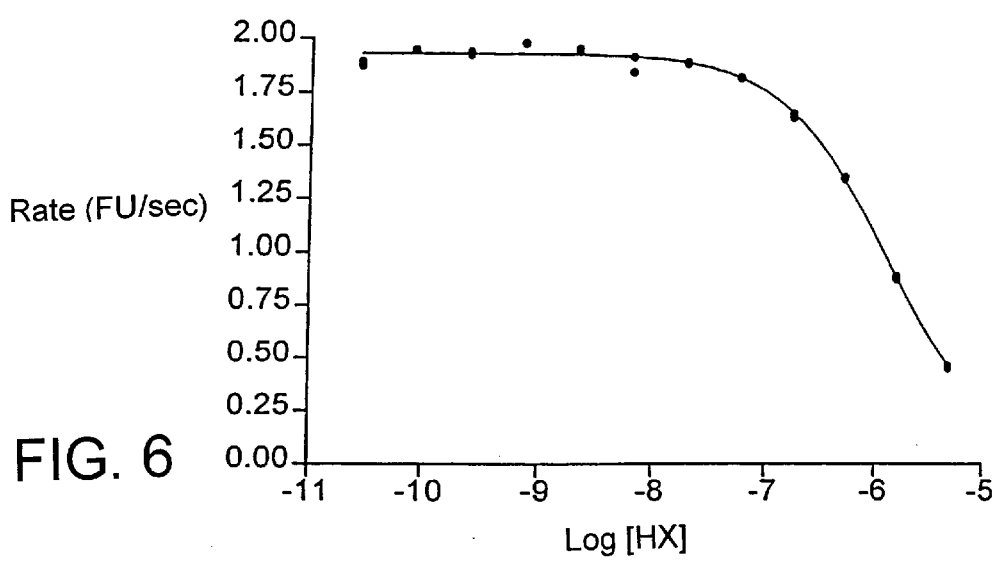
FIG. 6 is a graph depicting the inhibition of human ACE-2 when treated with Compound HX.
Figure 7:
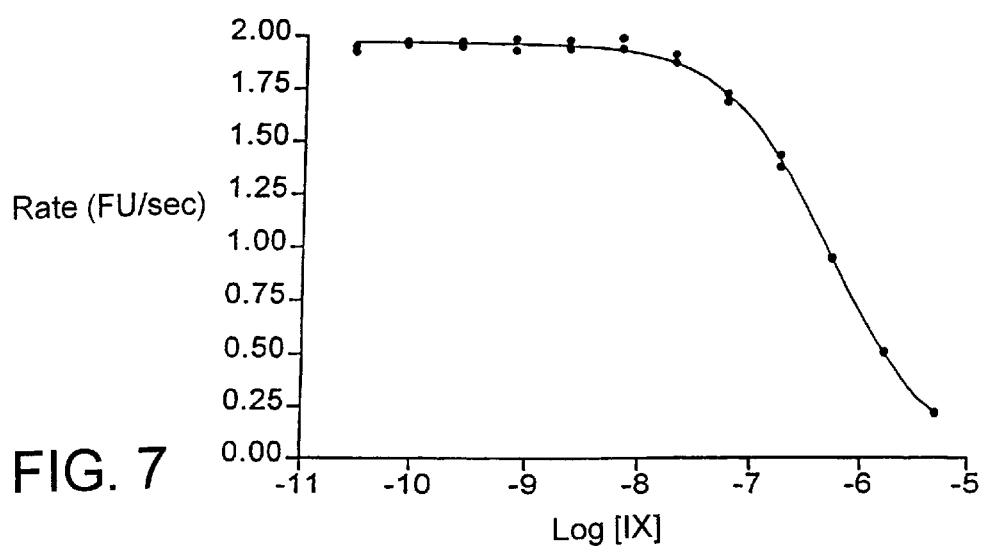
FIG. 7 is a graph depicting the inhibition of human ACE-2 when treated with Compound IX.

FIGS. 5, 6, and 7 are graphs of the inhibition of human ACE-2 with Compounds HW, HX, and IX, respectively. The graphs show that these compounds inhibit the activity of human ACE-2.

TABLE 2

| Ref. No. | Structure | Chemical Name | M. W. |
|---|---|---|---|
| A | 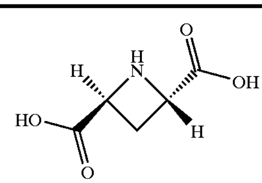 | Azetidine-2,4-dicarboxylic acid | 145.11 |

TABLE 2-continued

| | Structure | Name | MW |
|---|---|---|---|
| B | (structure) | 2-(1-Ethoxycarbonyl-3-phenyl-propylamino)-4-methyl-pentanoic acid | 321.42 |
| C | (structure) | 2-(1-Carboxy-3-phenyl-propylamino)-4-methyl-pentanoic acid | 293.36 |
| D | (structure) | 2-(1-Carboxy-3-phenyl-propylamino)-4-methyl-pentanoic acid | 293.36 |
| E | (structure) | 2-(1-Carboxy-3-phenyl-propylamino)-4-methyl-pentanoic acid | 293.36 |
| G | (structure) | 3-Mercapto-2-methyl-propionic acid | 120.17 |
| H | (structure) | Piperidine-2,6-dicarboxylic acid | 173.17 |
| I | (structure) | 2-(1-Carboxy-ethylamino)-5-guanidino-pentanoic acid | 246.27 |

TABLE 2-continued

| | | | |
|---|---|---|---|
| J | | 2-{[Carboxy-(2-nitro-phenyl)-methyl]-amino}-pentanedioic acid | 326.26 |
| K | | 6-Amino-2-(bis-carboxymethyl-amino)-hexanoic acid | 262.26 |
| L | | 5,5-Dimethyl-thiazolidine-2,4-dicarboxylic acid | 205.23 |
| M | | 5-Amino-2-(1-carboxy-ethylamino)-pentanoic acid | 204.23 |
| N | | 2-(1-Carboxy-ethylamino)-3-(1H-imidazol-4-yl)-propionic acid | 227.22 |
| O | | 2-(1-Carboxy-ethylamino)-3-phenyl-propionic acid | 237.26 |
| P | | 2-(1-Carboxy-ethylamino)-4-phenyl-butyric acid | 251.28 |

TABLE 2-continued

| | Structure | Name | MW |
|---|---|---|---|
| Q | 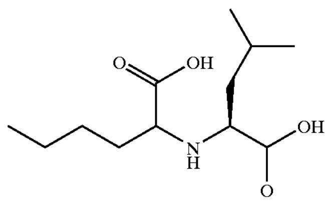 | 2-(1-Carboxy-3-methyl-butylamino)-hexanoic acid | 245.32 |
| R | 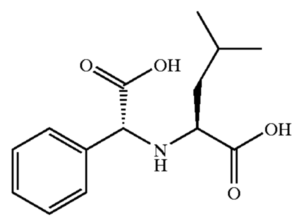 | 2-[(Carboxy-phenyl-methyl)-amino]-4-methyl-pentanoic acid | 265.31 |
| T | 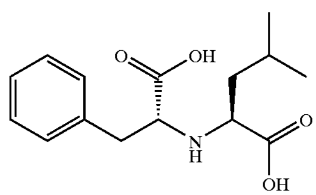 | 2-(1-Carboxy-2-phenyl-ethylamino)-4-methyl-pentanoic acid | 279.34 |
| U | 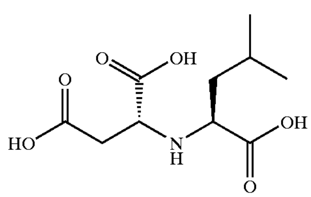 | 2-(1-Carboxy-3-methyl-butylamino)-succinic acid | 247.25 |
| V | 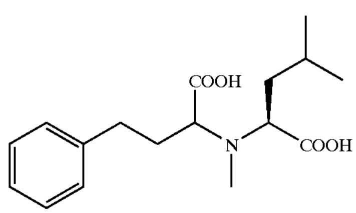 | 2-[(1-Carboxy-3-phenyl-propyl)-methyl-amino]-4-methyl-pentanoic acid | 307.39 |
| W | 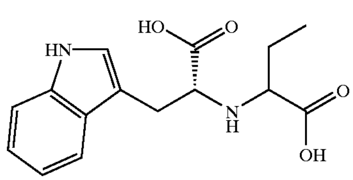 | 2-[1-Carboxy-2-(1H-indol-3-yl)-ethylamino]-butyric acid | 290.32 |
| X | 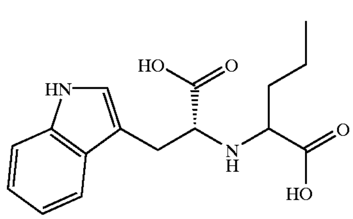 | 2-[1-Carboxy-2-(1H-indol-3-yl)-ethylamino]-pentanoic acid | 340.81 |

TABLE 2-continued

| | | | |
|---|---|---|---|
| Y | 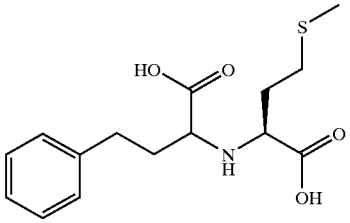 | 2-(1-Carboxy-3-methylsulfanyl-propylamino)-4-phenyl-butyric acid | 311.40 |
| Z | 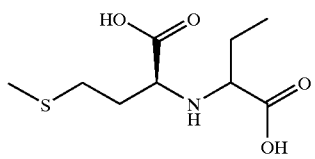 | 2-(1-Carboxy-propylamino)-4-methylsulfanyl-butyric acid | 235.30 |
| AA | 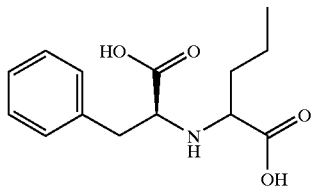 | 2-(1-Carboxy-2-phenyl-ethylamino)-pentanoic acid | 265.31 |
| AB | 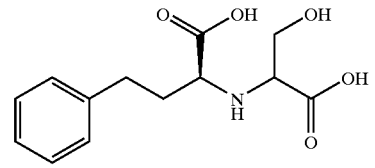 | 2-(1-Carboxy-2-hydroxy-ethylamino)-4-phenyl-butyric acid | 267.28 |
| AC | 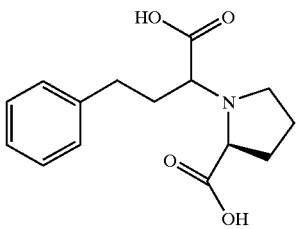 | 1-(1-Carboxy-3-phenyl-propyl)-pyrrolidine-2-carboxylic acid | 277.32 |
| AD | 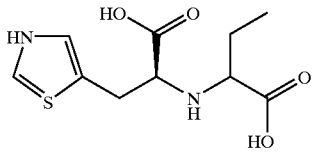 | 2-(1-Carboxy-ethylamino)-3-(1H-imidazol-4-yl)-propionic acid | 241.25 |
| AE | 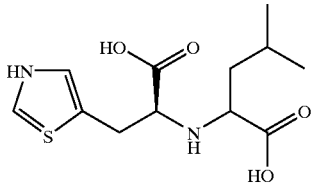 | 2-[1-Carboxy-2-(1H-imidazol-4-yl)-ethylamino]-4-methyl-pentanoic acid | 269.30 |
| AF | 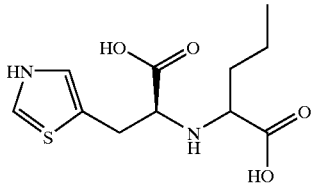 | 2-[1-Carboxy-2-(1H-imidazol-4-yl)-ethylamino]-pentanoic acid | 291.73 |

TABLE 2-continued

| | Structure | Name | MW |
|---|---|---|---|
| AG | 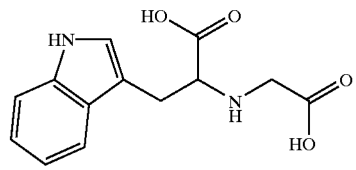 | 2-(1-Carboxy-ethylamino)-3-(1H-indol-3-yl)-propionic acid | 276.29 |
| AH | 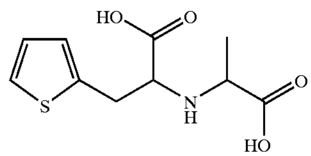 | 2-(1-Carboxy-ethylamino)-3-thiophen-2-yl-propionic acid | 243.28 |
| AI | 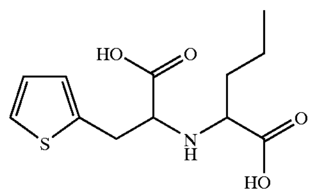 | 2-(1-Carboxy-2-thiophen-2-yl-ethylamino)-pentanoic acid | 271.34 |
| AJ | 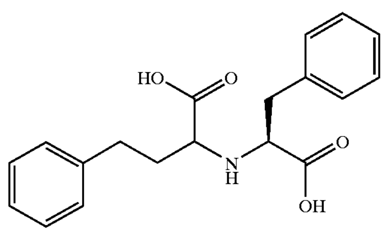 | 2-(1-Carboxy-2-phenyl-ethylamino)-4-phenyl-butyric acid | 327.38 |
| AK | 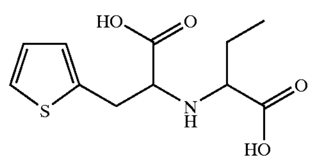 | 2-(1-Carboxy-2-thiophen-2-yl-ethylamino)-butyric acid | 257.31 |
| AL | 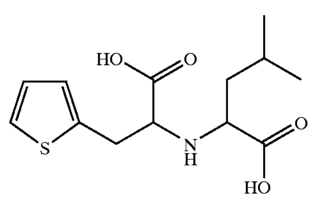 | 2-(1-Carboxy-2-thiophen-2-yl-ethylamino)-4-methyl-pentanoic acid | 321.82 |
| AM | 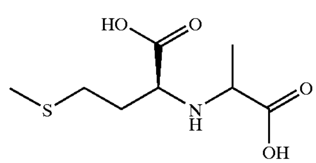 | 2-(1-Carboxy-ethylamino)-4-methylsulfanyl-butyric acid | 221.28 |
| AN | 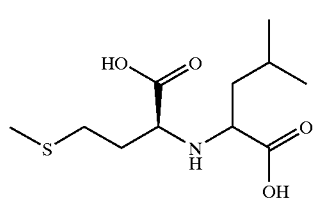 | 2-(1-Carboxy-3-methylsulfanyl-propylamino)-4-methyl-pentanoic acid | 280.39 |

| | | | |
|---|---|---|---|
| AO | | 2-(1-Carboxy-3-methylsulfanyl-propylamino)-pentanoic acid | 285.79 |
| AP | | 2-[1-Carboxy-2-(methyl-phenyl-amino)-ethylamino]-4-methyl-pentanoic acid | 308.38 |
| AQ | | 2-(1-Carboxy-butylamino)-4-methyl-pentanoic acid | 231.29 |
| AR | | 2-{[Carboxy-(4-trifluoromethyl-phenyl)-methyl]-amino}-4-methyl-pentanoic acid | 333.31 |
| AS | | 2-(1-Carboxy-3-phenyl-propylamino)-3-methyl-butyric acid | 279.34 |
| AT | | 2-[Acetyl-(1-carboxy-3-phenyl-propyl)-amino]-4-methyl-pentanoic acid; Isomer A | 335.40 |
| AU | | 2-[Acetyl-(1-carboxy-3-phenyl-propyl)-amino]-4-methyl-pentanoic acid; Isomer B | 335.40 |

TABLE 2-continued

| | | | |
|---|---|---|---|
| AV | | 2-[Benzoyl-(1-carboxy-3-phenyl-propyl)-amino]-4-methyl-pentanoic acid | 397.47 |
| AW | | 2-(1-Carboxy-ethylamino)-4-phenyl-butyric acid | 268.31 |
| AX | | 2-(1-Carboxy-3-phenyl-propylamino)-3-methyl-pentanoic acid | 293.36 |
| AZ | | 2-(1-Carboxy-3-phenyl-propylamino)-succinic acid | 295.29 |
| BA | | 2-(1-Carboxy-3-phenyl-propylamino)-pentanoic acid | 279.34 |
| BB | | 2-[1-Carboxy-2-(1H-imidazol-4-yl)-ethylamino]-4-methyl-pentanoic acid | 269.30 |
| BC | | 2-[1-Carboxy-2-(1H-imidazol-4-yl)-ethylamino]-pentanoic acid | 255.27 |

TABLE 2-continued

| | | | |
|---|---|---|---|
| BD | | 2-(1-Carboxy-ethylamino)-3-(1H-imidazol-4-yl)-propionic acid | 227.22 |
| BE | | 2-[1-Carboxy-2-(1H-imidazol-4-yl)-ethylamino]-3-methyl-pentanoic acid | 269.30 |
| BF | | 2-(1-Carboxy-2-pyridin-2-yl-ethylamino)-4-methyl-pentanoic acid | 280.32 |
| BG | | 2-(1-Carboxy-2-cyclohexyl-ethylamino)-4-phenyl-butyric acid | 369.89 |
| BH | | 2-(1-Carboxy-3-phenyl-propylamino)-4-methyl-pentanoic acid | 293.36 |
| BI | | 2-[1-Carboxy-2-(1H-imidazol-4-yl)-ethylamino]-4-methyl-pentanoic acid; Isomer A | 269.30 |
| BJ | | 2-[1-Carboxy-2-(1H-imidazol-4-yl)-ethylamino]-4-methyl-pentanoic acid; Isomer B | 269.30 |
| BK | | 2-[1-Carboxy-2-(1H-imidazol-4-yl)-ethylamino]-4-methyl-pentanoic acid; Isomer A | 269.30 |

TABLE 2-continued

| | | | |
|---|---|---|---|
| BL | | 2-[1-Carboxy-2-(1H-imidazol-4-yl)-ethylamino]-4-methyl-pentanoic acid; Isomer B | 269.30 |
| BN | | 2-[(Carboxy-phenyl-methyl)-amino]-pent-4-ynoic acid | 291.23 |
| BO | | 2-[(Carboxy-phenyl-methyl)-amino]-3-phenyl-propionic acid | 343.31 |
| BP | | 2-[(Carboxy-phenyl-methyl)-amino]-3-cyclohexyl-propionic acid | 305.37 |
| BQ | | 2-{[Carboxy-(4-methoxy-phenyl)-methyl]-amino}-4-methyl-pentanoic acid | 295.34 |
| BR | | 2-[(Carboxy-naphthalen-2-yl-methyl)-amino]-4-methyl-pentanoic acid | 315.37 |
| BS | | 2-[(Carboxy-phenyl-methyl)-amino]-4-methyl-pentanoic acid | 265.31 |

TABLE 2-continued

| | Structure | Name | MW |
|---|---|---|---|
| BT | 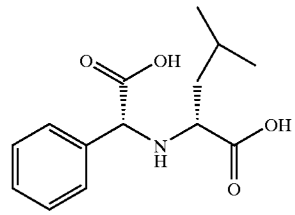 | 2-[(Carboxy-phenyl-methyl)-amino]-4-methyl-pentanoic acid | 265.31 |
| BU | 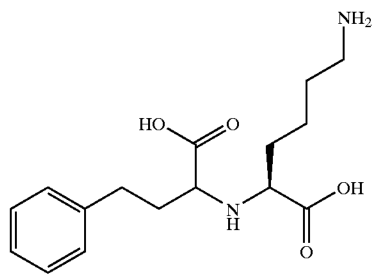 | 6-Amino-2-(1-carboxy-3-phenyl-propylamino)-hexanoic acid | 308.38 |
| BV | 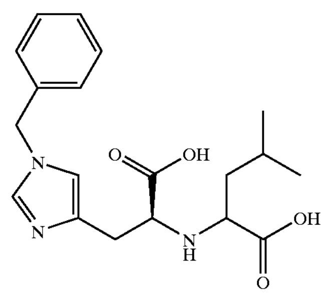 | 2-[2-(1-Benzyl-1H-imidazol-4-yl)-1-carboxy-ethylamino]-4-methyl-pentanoic acid | 359.43 |
| BW | 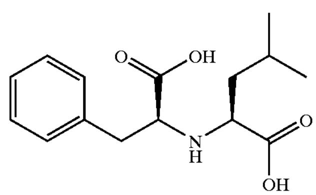 | 2-(1-Carboxy-2-phenyl-ethylamino)-4-methyl-pentanoic acid | 279.34 |
| BX | 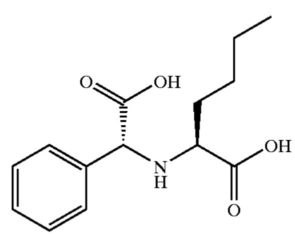 | 2-[(Carboxy-phenyl-methyl)-amino]-hexanoic acid | 265.31 |
| BY | 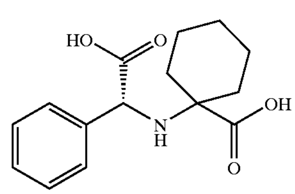 | 1-[(Carboxy-phenyl-methyl)-amino]-cyclohexanecarboxylic acid | 277.32 |
| BZ | 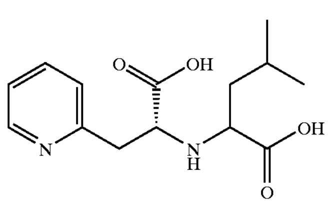 | 2-(1-Carboxy-2-pyridin-2-yl-ethylamino)-4-methyl-pentanoic acid | 280.32 |

TABLE 2-continued

| | | | |
|---|---|---|---|
| CA | | 2-[1-Carboxy-2-(1-methyl-1H-imidazol-4-yl)-ethylamino]-4-methyl-pentanoic acid | 283.33 |
| CB | | 2-[1-Carboxy-2-(3-methyl-3H-imidazol-4-yl)-ethylamino]-4-methyl-pentanoic acid | 283.33 |
| CC | | 2-(1-Carboxy-2-pyridin-3-yl-ethylamino)-4-methyl-pentanoic acid | 280.32 |
| CD | | 2-[1-Carboxy-2-(1H-[1.2.4]triazol-3-yl)-ethylamino]-4-methyl-pentanoic acid | 270.29 |
| CE | | 2-[1-Carboxy-2-(1H-[1.2.4]triazol-3-yl)-ethylamino]-4-methyl-pentanoic acid | 270.29 |
| CF | | 2-(1-Carboxy-2-thiazol-2-yl-ethylamino)-4-methyl-pentanoic acid | 286.35 |
| CG | | 2-(2-Carboxy-propylamino)-4-methyl-pentanoic acid | 217.27 |

TABLE 2-continued

| | | | |
|---|---|---|---|
| CH | | 2-(1-Carboxy-3-phenyl-propylamino)-octanoic acid | 321.42 |
| CI | | 2-(1-Carboxymethyl-3-phenyl-propylamino)-4-methyl-pentanoic acid | 307.39 |
| CJ | | 2-[(Carboxy-phenyl-methyl)-amino]-4,4-dimethyl-pentanoic acid | 315.80 |
| CK | | 2-(1-Carboxy-3-phenyl-propylamino)-4,4-dimethyl-pentanoic acid | 307.39 |
| CL | | 2-(1-Carboxy-2-cyclopropyl-ethylamino)-4-phenyl-butyric acid | 291.35 |
| CM | | 2-(1-Carboxy-3-phenyl-propylamino)-4-methyl-pentanoic acid | |

TABLE 2-continued

| | | | |
|---|---|---|---|
| CN | | 4-[(1-Carboxy-3-methyl-butylamino)-methyl]-benzoic acid | 265.31 |
| CO | | 2-(1-Carboxy-2-thiazol-4-yl-ethylamino)-4-methyl-pentanoic acid | 303.38 |
| CP | | 2-(1-Carboxy-2-thiophen-2-yl-ethylamino)-4-methyl-pentanoic acid | 285.36 |
| CQ | | 2-(2-Carboxy-1-phenyl-ethylamino)-4-methyl-pentanoic acid | 279.34 |
| CR | | 2-[1-Carboxy-2-(1H-imidazol-4-yl)-ethylamino]-octanoic acid | 297.35 |
| CS | | 2-[2-Carboxy-1-(4-methyl-benzyl)-ethylamino]-4-methyl-pentanoic acid | 343.85 |
| CT | | 2-[2-(1H-Imidazol-4-yl)-1-methoxycarbonyl-ethylamino]-4-methyl-pentanoic acid; Isomer A | 283.33 |

TABLE 2-continued

| | | | |
|---|---|---|---|
| CU | | 2-[2-(1H-Imidazol-4-yl)-1-methoxycarbonyl-ethylamino]-4-methyl-pentanoic acid; Isomer B | 283.33 |
| CV | | 2-(1-Carboxy-2-thiazol-4-yl-ethylamino)-4-methyl-pentanoic acid | 303.38 |
| CW | | 2-[2-(1-Benzyl-1H-imidazol-4-yl)-1-carboxy-ethylamino]-4-methyl-pentanoic acid | 359.43 |
| CX | | 2-[2-(1-Benzyl-1H-imidazol-4-yl)-1-carboxy-ethylamino]-4-methyl-pentanoic acid | 395.89 |
| CY | | 4-Methyl-2-(3-phenyl-propylamino)-pentanoic acid | 249.35 |
| CZ | | 2-(1-Carboxy-3-phenyl-propylamino)-4-methyl-pentanoic acid tert-butyl ester | 349.47 |
| DA | | 2-(1-Carboxy-3-phenyl-propylamino)-4-methyl-pentanoic acid tert-butyl ester | 349.47 |

TABLE 2-continued

| | | Name | MW |
|---|---|---|---|
| DB | | 2-(1-Carbamoyl-3-methyl-butylamino)-4-phenyl-butyric acid | 292.38 |
| DC | | 2-(1-Carbamoyl-3-methyl-butylamino)-4-phenyl-butyric acid | 322.45 |
| DD | | 2-(1-Carboxy-3-phenyl-propylamino)-4,4-dimethyl-pentanoic acid | 307.39 |
| DE | | 2-(1-Carboxy-2-cyclopropyl-ethylamino)-4-phenyl-butyric acid | 291.35 |
| DF | | 2-(3-Benzyl-ureido)-4-methyl-pentanoic acid methyl ester | 278.35 |
| DG | | 4-Methyl-2-(3-phenethyl-ureido)-pentanoic acid methyl ester | 292.38 |
| DH | | 2-(2-Biphenyl-4-yl-2-oxo-ethylamino)-4-methyl-pentanoic acid methyl ester | 339.43 |

TABLE 2-continued

| | | | |
|---|---|---|---|
| DI | | 2-(3-Benzyloxycarbonylamino-2-oxo-4-phenyl-butylamino)-4-methyl-pentanoic acid methyl ester | 440.54 |
| DJ | | 2-[1-Carboxy-2-(1H-imidazol-4-yl)-ethylamino]-pentanoic acid; Isomer A | 315.32 |
| DK | | 2-[1-Carboxy-2-(1H-imidazol-4-yl)-ethylamino]-pentanoic acid; Isomer B | 255.27 |
| DL | | 2-[2-(1-Benzyl-1H-imidazol-4-yl)-1-carboxy-ethylamino]-4-methyl-pentanoic acid; Isomer A | 359.43 |
| DM | | 2-[2-(1-Benzyl-1H-imidazol-4-yl)-1-carboxy-ethylamino]-4-methyl-pentanoic acid; Isomer B | 359.43 |
| DN | | 2-[1-Carboxy-2-(4-hydroxy-phenyl)-ethylamino]-3-(1H-imidazol-4-yl)-propionic acid; Isomer A | 319.32 |
| DO | | 2-[1-Carboxy-2-(4-hydroxy-phenyl)-ethylamino]-3-(1H-imidazol-4-yl)-propionic acid; Isomer B | 319.32 |

TABLE 2-continued

| | Structure | Name | MW |
|---|---|---|---|
| DP | 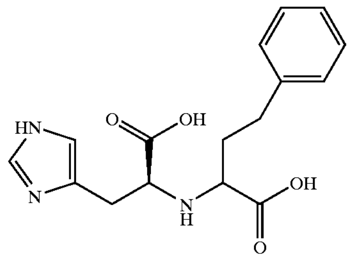 | 2-[1-Carboxy-2-(1H-imidazol-4-yl)-ethylamino]-4-phenyl-butyric acid | 317.34 |
| DQ | 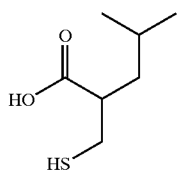 | 2-Mercaptomethyl-4-methyl-pentanoic acid | 162.25 |
| DR | 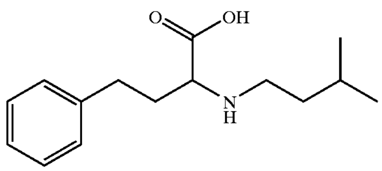 | 2-(3-Methyl-butylamino)-4-phenyl-butyric acid | 249.35 |
| DS | 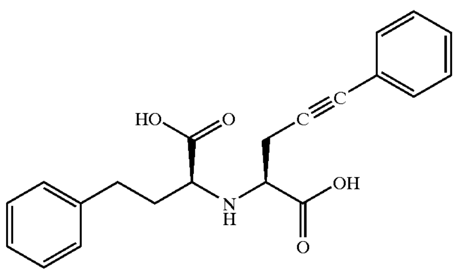 | 2-(1-Carboxy-3-phenyl-propylamino)-5-phenyl-pent-4-ynoic acid | 351.40 |
| DT | 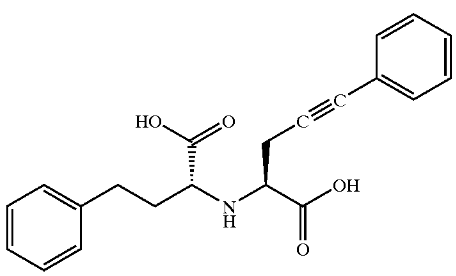 | 2-(1-Carboxy-3-phenyl-propylamino)-5-phenyl-pent-4-ynoic acid | 351.40 |
| DU | 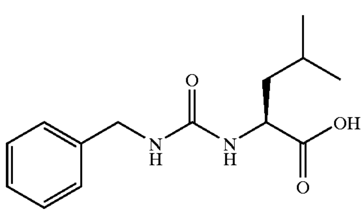 | 2-(3-Benzyl-ureido)-4-methyl-pentanoic acid | 264.32 |
| DV | 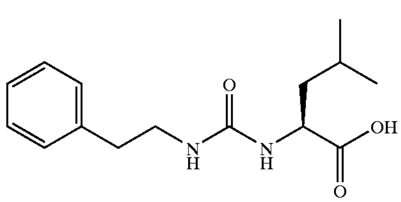 | 4-Methyl-2-(3-phenethyl-ureido)-pentanoic acid | 278.35 |

TABLE 2-continued

| | | | |
|---|---|---|---|
| DW | | 4-Methyl-2-(2-oxo-2-phenyl-ethylamino)-pentanoic acid | 285.77 |
| DX | | 2-[2-(3-Benzyloxymethyl-3H-imidazol-4-yl)-1-carboxy-ethylamino]-4-methyl-pentanoic acid | 433.43 |
| DY | | 3-(1H-Imidazol-4-yl)-2-(3-methyl-butylamino)-propionic acid | 285.34 |
| DZ | | 2-[2-(1H-Imidazol-4-yl)-ethylamino]-4-methyl-pentanoic acid | 225.29 |
| EA | | 2-(1-Carboxy-3-phenyl-propylamino)-5-pyridin-2-yl-pent-4-ynoic acid | 352.39 |
| EB | | 2-(1-Carboxy-3-phenyl-propylamino)-5-pyridin-2-yl-pent-4-ynoic acid | 352.39 |

TABLE 2-continued

| | | | |
|---|---|---|---|
| EC | | 2-{1-Carboxy-2-[1-(4-chloro-benzyl)-1H-imidazol-4-yl]-ethylamino}-4-methyl-pentanoic acid | 410.90 |
| ED | | 2-[1-Carboxy-2-(1H-imidazol-4-yl)-ethylamino]-hexanoic acid; Isomer A | 269.30 |
| EF | | 2-[1-Carboxy-2-(1H-imidazol-4-yl)-ethylamino]-hexanoic acid; Isomer B | 299.39 |
| EG | | 2-{1-Carboxy-2-[1-(2,4-dinitro-phenyl)-1H-imidazol-4-yl]-ethylamino}-4-methyl-pentanoic acid | 452.42 |
| EH | | 2-(1-Carboxymethyl-2-furan-2-yl-ethylamino)-4-methyl-pentanoic acid | 327.30 |
| EI | | 2-(1-Carboxymethyl-2-thiophen-2-yl-ethylamino)-4-methyl-pentanoic acid | 343.37 |

TABLE 2-continued

| | | | |
|---|---|---|---|
| EJ | 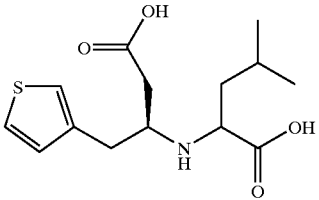 | 2-(1-Carboxymethyl-2-thiophen-3-yl-ethylamino)-4-methyl-pentanoic acid | 343.37 |
| EK | 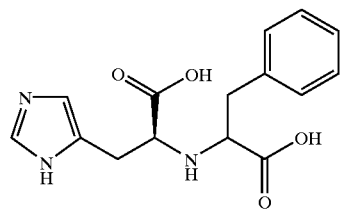 | 2-(1-Carboxy-2-phenyl-ethylamino)-3-(3H-imidazol-4-yl)-propionic acid | 303.32 |
| EL | 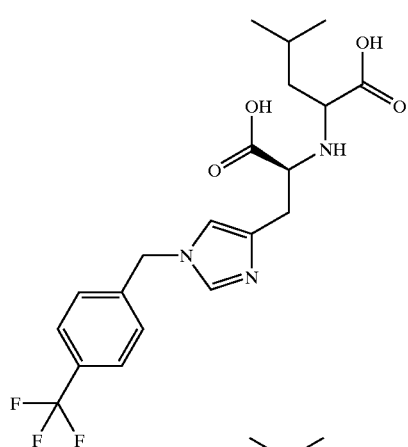 | 2-{1-Carboxy-2-[1-(4-trifluoromethyl-benzyl)-1H-imidazol-4-yl]-ethylamino}-4-methyl-pentanoic acid | 427.42 |
| EM | 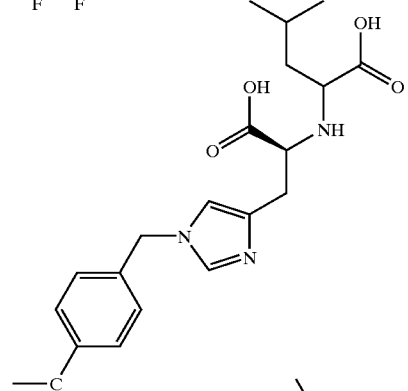 | 2-{1-Carboxy-2-[1-(4-methoxy-benzyl)-1H-imidazol-4-yl]-ethylamino}-4-methyl-pentanoic acid | 389.45 |
| EN | 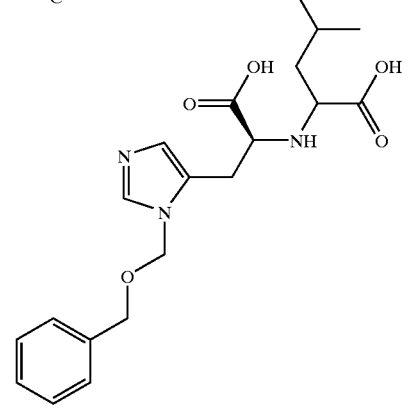 | 2-[2-(3-Benzyloxymethyl-3H-imidazol-4-yl)-1-carboxy-ethylamino]-4-methyl-pentanoic acid; Isomer A | 389.45 |

TABLE 2-continued

| | | | |
|---|---|---|---|
| EO | | 2-[2-(3-Benzyloxymethyl-3H-imidazol-4-yl)-1-carboxy-ethylamino]-4-methyl-pentanoic acid; Isomer B | 389.45 |
| EQ | | 2-(1-Carboxy-2-phenyl-ethylamino)-3-(1H-imidazol-4-yl)-propionic acid | 303.32 |
| ER | | 2-[1-Carboxy-2-(1H-imidazol-4-yl)-ethylamino]-4-phenyl-butyric acid | 317.34 |
| ES | | 3-[1-Carboxy-2-(1H-imidazol-4-yl)-ethylamino]-heptanoic acid; Isomer A | 283.33 |
| ET | | 3-[1-Carboxy-2-(1H-imidazol-4-yl)-ethylamino]-heptanoic acid; Isomer B | 283.33 |
| EU | | 2-{1-Carboxy-2-[1-(4-chloro-benzyl)-1H-imidazol-4-yl]-ethylamino}-4-methyl-pentanoic acid | 393.87 |
| EV | | 2-[1-Carbamoyl-2-(1H-imidazol-4-yl)-ethylamino]-4-methyl-pentanoic acid; Isomer A | 268.316 |

TABLE 2-continued

| | | | |
|---|---|---|---|
| EW | | 2-[1-Carbamoyl-2-(1H-imidazol-4-yl)-ethylamino]-4-methyl-pentanoic acid; Isomer B | 268.316 |
| EX | | 2-[2-(1H-Imidazol-4-yl)-1-(4-nitro-phenylcarbamoyl)-ethylamino]-4-methyl-pentanoic acid; Isomer A | 389.411 |
| EY | | 2-[2-(1H-Imidazol-4-yl)-1-(4-nitro-phenylcarbamoyl)-ethylamino]-4-methyl-pentanoic acid; Isomer B | 389.411 |
| EZ | | 2-[2-(3-Benzyl-3H-imidazol-4-yl)-1-carboxy-ethylamino]-4-methyl-pentanoic acid; Isomer A | 359.425 |
| FA | | 2-[2-(3-Benzyl-3H-imidazol-4-yl)-1-carboxy-ethylamino]-4-methyl-pentanoic acid; Isomer B | 359.425 |

TABLE 2-continued
| | | | |
|---|---|---|---|
| FB | 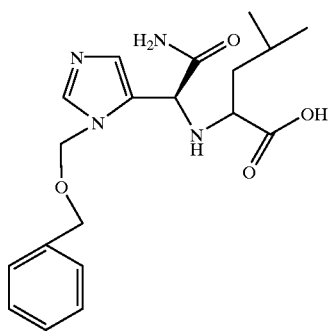 | 2-[2-(3-Benzyloxymethyl-3H-imidazol-4-yl)-1-carbamoyl-ethylamino]-4-methyl-pentanoic acid; Isomer A | 388.47 |
| FC | 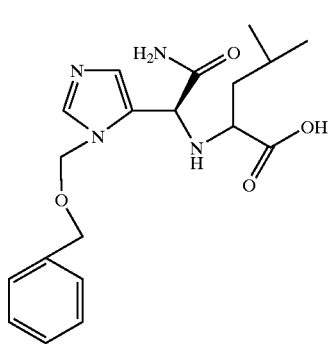 | 2-[2-(3-Benzyloxymethyl-3H-imidazol-4-yl)-1-carbamoyl-ethylamino]-4-methyl-pentanoic acid; Isomer B | 388.47 |
| FD | 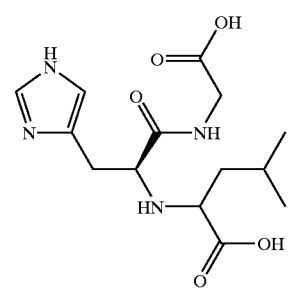 | 2-[1-(Carboxymethyl-carbamoyl)-2-(1H-imidazol-4-yl)-ethylamino]-4-methyl-pentanoic acid | 326.35 |
| FE | 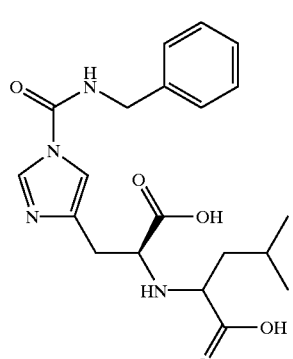 | 2-[1-(Carboxymethyl-carbamoyl)-2-(1H-imidazol-4-yl)-ethylamino]-4-methyl-pentanoic acid | 402.45 |

TABLE 2-continued

| | | | |
|---|---|---|---|
| FG | | 2-[2-(3-Benzyloxymethyl-3H-imidazol-4-yl)-1-carboxy-ethylamino]-4-methyl-pentanoic acid; Isomer A | 389.45 |
| FH | | 2-[2-(3-Benzyloxymethyl-3H-imidazol-4-yl)-1-carboxy-ethylamino]-4-methyl-pentanoic acid; Isomer B | 389.45 |
| FI | | 2-(1-Carboxy-2-phenylamino-ethylamino)-4-methyl-pentanoic acid; Isomer A | 294.35 |
| FJ | | 2-(1-Carboxy-2-phenylamino-ethylamino)-4-methyl-pentanoic acid; Isomer B | 294.35 |
| FK | | 2-{2-(3H-Imidazol-4-yl)-1-[2-(4-methoxy-phenyl)-ethylcarbamoyl]-ethylamino}-4-methyl-pentanoic acid; Isomer A | 402.49 |

TABLE 2-continued

| | | | |
|---|---|---|---|
| FL | 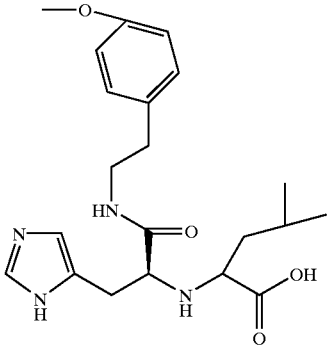 | 2-{2-(3H-Imidazol-4-yl)-1-[2-(4-methoxy-phenyl)-ethylcarbamoyl]-ethylamino}-4-methyl-pentanoic acid; Isomer B | 402.49 |
| FM | 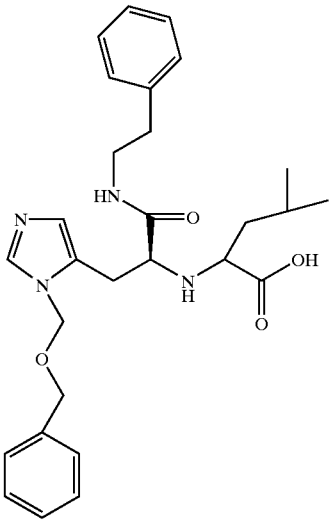 | 2-[2-(3-Benzyloxymethyl-3H-imidazol-4-yl)-1-phenethylcarbamoyl-ethylamino]-4-methyl-pentanoic acid; Isomer A | 492.62 |
| FN | 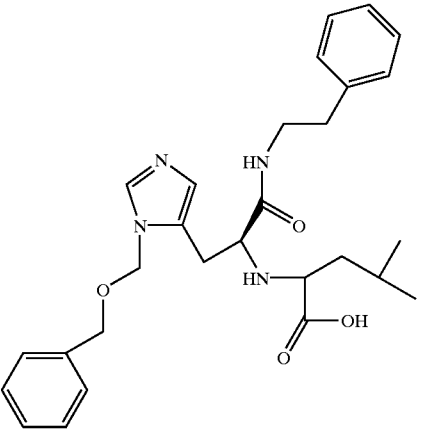 | 2-[2-(3-Benzyloxymethyl-3H-imidazol-4-yl)-1-phenethylcarbamoyl-ethylamino]-4-methyl-pentanoic acid; Isomer B | 492.62 |
| FO | 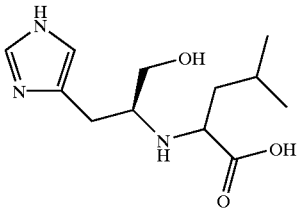 | 2-[1-Hydroxymethyl-2-(1H-imidazol-4-yl)-ethylamino]-4-methyl-pentanoic acid; Isomer A | 255.32 |

TABLE 2-continued

| | | | |
|---|---|---|---|
| FP | | 2-[1-Hydroxymethyl-2-(1H-imidazol-4-yl)-ethylamino]-4-methyl-pentanoic acid; Isomer B | 255.32 |
| FQ | | 2-(1-Carboxy-3-phenyl-propylamino)-5-(4-methoxy-phenyl)-pent-4-ynoic acid | 417.89 |
| FR | | 2-(1-Carboxy-3-phenyl-propylamino)-5-(4-methoxy-phenyl)-pent-4-ynoic acid | 417.89 |
| FS | | 2-[1-Carboxy-2-(methyl-phenyl-amino)-ethylamino]-4-methyl-pentanoic acid | 308.38 |
| FT | | 2-[1-Carboxy-2-(methyl-phenyl-amino)-ethylamino]-4-methyl-pentanoic acid | 308.38 |

TABLE 2-continued

| | | | |
|---|---|---|---|
| FU | | 2-[2-(Benzyl-methyl-amino)-1-carboxy-ethylamino]-4-methyl-pentanoic acid | 322.40 |
| FV | | 2-[2-(Benzyl-methyl-amino)-1-carboxy-ethylamino]-4-methyl-pentanoic acid | 322.40 |
| FW | | 2-[2-(3H-Imidazol-4-yl)-1-phenethylcarbamoyl-ethylamino]-4-methyl-pentanoic acid; Isomer A | 372.47 |
| FX | | 2-[2-(3H-Imidazol-4-yl)-1-phenethylcarbamoyl-ethylamino]-4-methyl-pentanoic acid; Isomer B | 372.47 |
| FY | | 2-[2-(3-Benzyl-3H-imidazol-4-yl)-1-carboxy-ethylamino]-hexanoic acid; Isomer A | 359.43 |

TABLE 2-continued

| | | | |
|---|---|---|---|
| FZ | 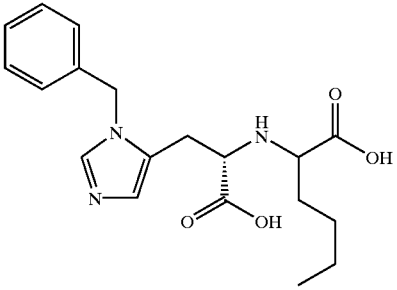 | 2-[2-(3-Benzyl-3H-imidazol-4-yl)-1-carboxy-ethylamino]-hexanoic acid; Isomer B | 359.43 |
| GA | 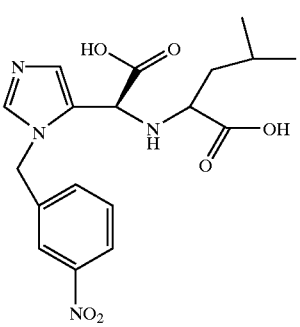 | 2-(1-Carboxy-2-[3-(3-nitro-benzyl)-3H-imidazol-4-yl]-ethylamino)-4-methyl-pentanoic acid; Isomer A | 404.42 |
| GB | 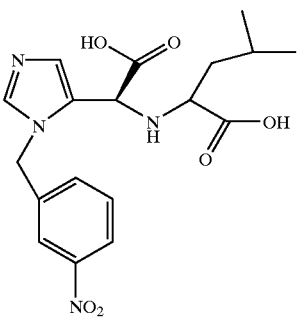 | 2-{1-Carboxy-2-[3-(3-nitro-benzyl)-3H-imidazol-4-yl]-ethylamino}-4-methyl-pentanoic acid; Isomer B | 404.42 |
| GC | 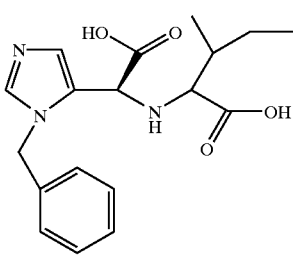 | 2-[2-(3-Benzyl-3H-imidazol-4-yl)-1-carboxy-ethylamino]-3-methyl-pentanoic acid; Isomer A | 359.42 |
| GD | 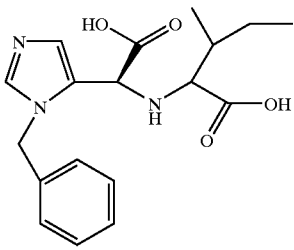 | 2-[2-(3-Benzyl-3H-imidazol-4-yl)-1-carboxy-ethylamino]-3-methyl-pentanoic acid; Isomer B | 359.42 |

TABLE 2-continued

| | | | |
|---|---|---|---|
| GE | | 3-(3-Benzyl-3H-imidazol-4-yl)-2-(1-carboxy-2-phenyl-ethylamino)-propionic acid; Isomer A | 393.44 |
| GF | | 3-(3-Benzyl-3H-imidazol-4-yl)-2-(1-carboxy-2-phenyl-ethylamino)-propionic acid; Isomer B | 393.44 |
| GG | | 2-[2-(3-Benzyl-3H-imidazol-4-yl)-1-carboxy-ethylamino]-butyric acid; Isomer A | 331.37 |
| GH | | 2-[2-(3-Benzyl-3H-imidazol-4-yl)-1-carboxy-ethylamino]-butyric acid; Isomer B | 331.37 |
| GI | | 2-{1-Carboxy-2-[3-(4-trifluoromethyl-benzyl)-3H-imidazol-4-yl]-ethylamino}-4-methyl-pentanoic acid | 427.17 |
| GJ | | 2-{1-Carboxy-2-[3-(4-trifluoromethyl-benzyl)-3H-imidazol-4-yl]-ethylamino}-4-methyl-pentanoic acid | 427.424 |

TABLE 2-continued

| | | | |
|---|---|---|---|
| GK | 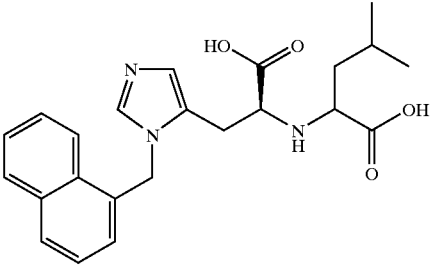 | 2-[1-Carboxy-2-(3-naphthalen-1-ylmethyl-3H-imidazol-4-yl)-ethylamino]-4-methyl-pentanoic acid; Isomer A | 409.48 |
| GL | 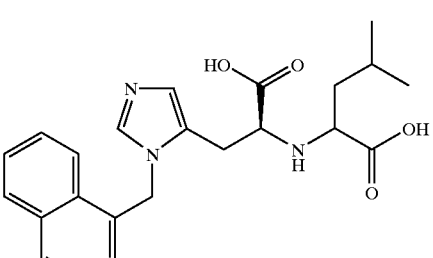 | 2-[1-Carboxy-2-(3-naphthalen-1-ylmethyl-3H-imidazol-4-yl)-ethylamino]-4-methyl-pentanoic acid; Isomer B | 409.48 |
| GM | 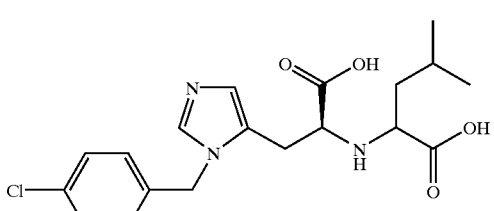 | 2-{1-Carboxy-2-[3-(4-chloro-benzyl)-3H-imidazol-4-yl]-ethylamino}-4-methyl-pentanoic acid; Isomer A | 393.87 |
| GN | 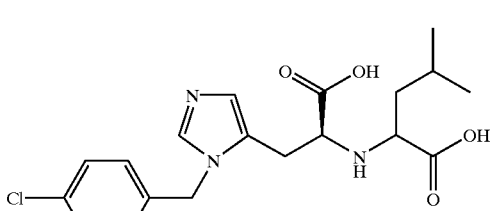 | 2-{1-Carboxy-2-[3-(4-chloro-benzyl)-3H-imidazol-4-yl]-ethylamino}-4-methyl-pentanoic acid; Isomer B | 393.87 |
| GO | 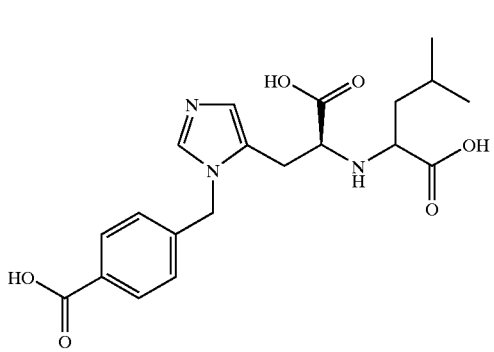 | 4-{5-[2-Carboxy-2-(1-carboxy-3-methyl-butylamino)-ethyl]-imidazol-1-ylmethyl}-benzoic acid; Isomer A | 403.435 |

TABLE 2-continued
| | | | |
|---|---|---|---|
| GP | 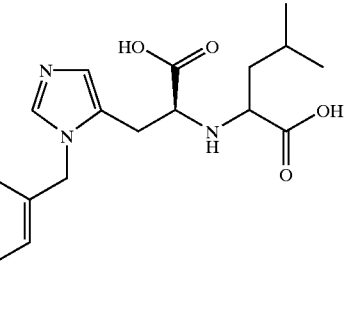 | 4-{5-[2-Carboxy-2-(1-carboxy-3-methyl-butylamino)-ethyl]-imidazol-1-ylmethyl}-benzoic acid; Isomer A | 403.435 |
| GQ | 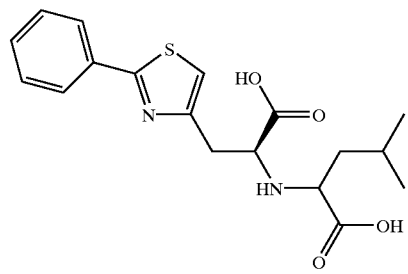 | 2-[1-Carboxy-2-(2-phenyl-thiazol-4-yl)-ethylamino]-4-methyl-pentanoic acid | 362.45 |
| GR | 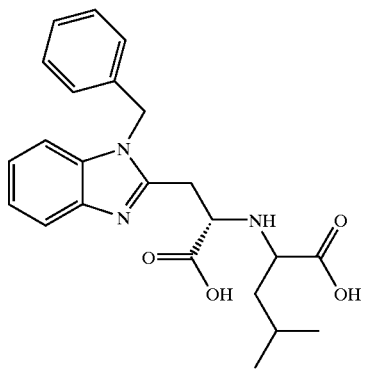 | 2-[2-(1-Benzyl-1H-benzoimidazol-2-yl)-1-carboxy-ethylamino]-4-methyl-pentanoic acid; Isomer A | 409.48 |
| GS | 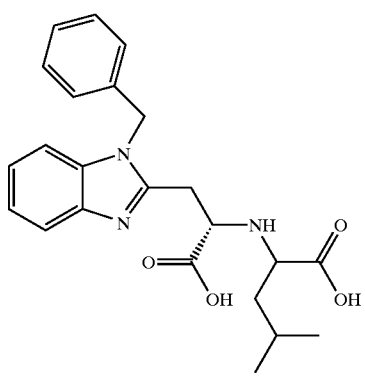 | 2-[2-(1-Benzyl-1H-benzoimidazol-2-yl)-1-carboxy-ethylamino]-4-methyl-pentanoic acid; Isomer B | 409.48 |

TABLE 2-continued

| | | | |
|---|---|---|---|
| GT | 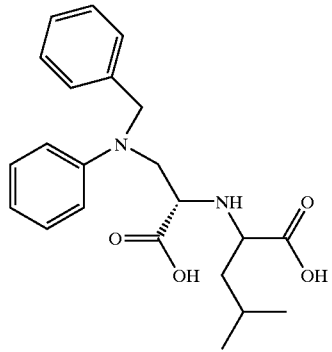 | 2-[2-(Benzyl-phenyl-amino)-1-carboxy-ethylamino]-4-methyl-pentanoic acid | 384.475 |
| GU | 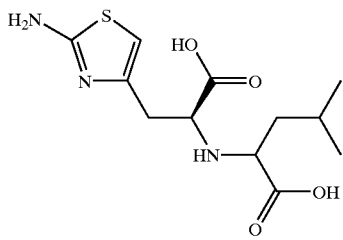 | 2-[2-(2-Amino-thiazol-4-yl)-1-carboxy-ethylamino]-4-methyl-pentanoic acid; Isomer A | 337.82 |
| GV | 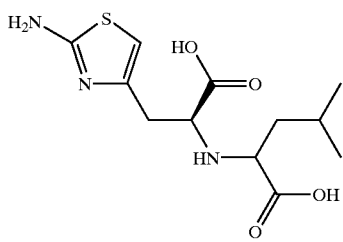 | 2-[2-(2-Amino-thiazol-4-yl)-1-carboxy-ethylamino]-4-methyl-pentanoic acid; Isomer B | 301.37 |
| GW | 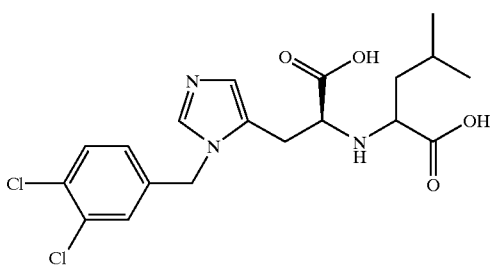 | 2-{1-Carboxy-2-[3-(3,4-dichloro-benzyl)-3H-imidazol-4-yl]-ethylamino}-4-methyl-pentanoic acid; Isomer A | 428.31 |
| GX | 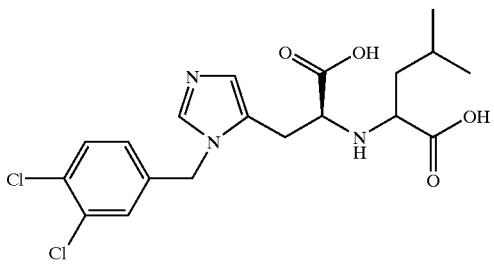 | 2-{1-Carboxy-2-[3-(3,4-dichloro-benzyl)-3H-imidazol-4-yl]-ethylamino}-4-methyl-pentanoic acid; Isomer B | 428.31 |

TABLE 2-continued

| | | | |
|---|---|---|---|
| GY | | 2-[1-Carboxy-2-(2-methyl-thiazol-4-yl)-ethylamino]-4-methyl-pentanoic acid; Isomer A | 300.38 |
| GZ | | 2-[1-Carboxy-2-(2-methyl-thiazol-4-yl)-ethylamino]-4-methyl-pentanoic acid; Isomer B | 300.38 |
| HA | | 2-{1-Carboxy-2-[3-(4-cyano-benzyl)-3H-imidazol-4-yl]-ethylamino}-4-methyl-pentanoic acid; Isomer A | 384.435 |
| HB | | 2-{1-Carboxy-2-[3-(4-cyano-benzyl)-3H-imidazol-4-yl]-ethylamino}-4-methyl-pentanoic acid; Isomer B | 384.43 |
| HC | | 2-{1-Carboxy-2-[3-(3-chloro-benzyl)-3H-imidazol-4-yl]-ethylamino}-4-methyl-pentanoic acid; Isomer A | 393.87 |
| HD | | 2-{1-Carboxy-2-[3-(3-chloro-benzyl)-3H-imidazol-4-yl]-ethylamino}-4-methyl-pentanoic acid; Isomer B | 393.87 |

TABLE 2-continued

| | | | |
|---|---|---|---|
| HE | | 2-{1-Carboxy-2-[3-(3,5-dichloro-benzyl)-3H-imidazol-4-yl]-ethylamino}-4-methyl-pentanoic acid; Isomer A | 428.31 |
| HF | | 2-{1-Carboxy-2-[3-(3,5-dichloro-benzyl)-3H-imidazol-4-yl]-ethylamino}-4-methyl-pentanoic acid; Isomer B | 428.31 |
| HG | | 2-{1-Carboxy-2-[3-(4-methyl-benzyl)-3H-imidazol-4-yl]-ethylamino}-4-methyl-pentanoic acid; Isomer A | 373.45 |
| HH | | 2-{1-Carboxy-2-[3-(4-methyl-benzyl)-3H-imidazol-4-yl]-ethylamino}-4-methyl-pentanoic acid; Isomer B | 373.45 |
| HI | | 2-{2-[3-(4-Butyl-benzyl)-3H-imidazol-4-yl]-1-carboxy-ethylamino}-4-methyl-pentanoic acid; Isomer A | 415.53 |

TABLE 2-continued
| | | | |
|---|---|---|---|
| HJ | 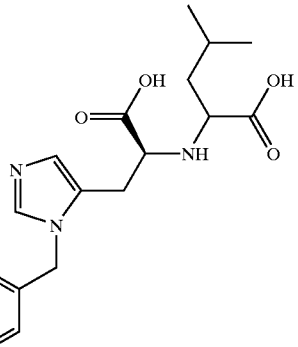 | 2-{2-[3-(4-Butyl-benzyl)-3H-imidazol-4-yl]-1-carboxy-ethylamino}-4-methyl-pentanoic acid; Isomer B | 415.53 |
| HK | 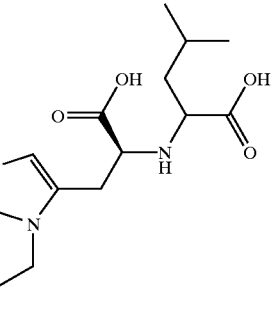 | 2-{1-Carboxy-2-[3-(3,4-dimethyl-benzyl)-3H-imidazol-4-yl]-ethylamino}-4-methyl-pentanoic acid; Isomer A | 387.48 |
| HL | 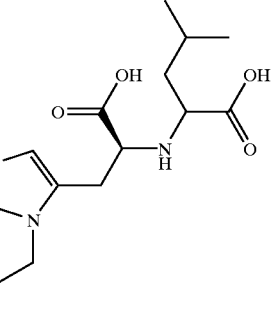 | 2-{1-Carboxy-2-[3-(3,4-dimethyl-benzyl)-3H-imidazol-4-yl]-ethylamino}-4-methyl-pentanoic acid; Isomer B | 387.48 |
| HM | 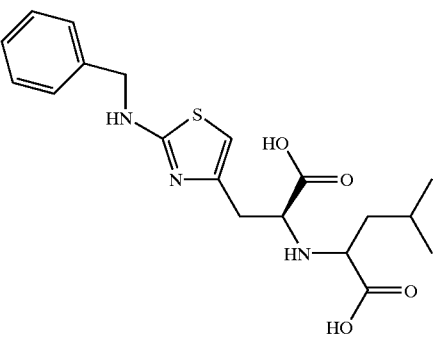 | 2-[2-(2-Benzylamino-thiazol-4-yl)-1-carboxy-ethylamino]-4-methyl-pentanoic acid; Isomer A | 391.49 |

TABLE 2-continued

| | | | |
|---|---|---|---|
| HN | | 2-[2-(2-Benzylamino-thiazol-4-yl)-1-carboxy-ethylamino]-4-methyl-pentanoic acid; Isomer B | 391.49 |
| HO | | 2-{1-Carboxy-2-[3-(3-methyl-benzyl)-3H-imidazol-4-yl]-ethylamino}-4-methyl-pentanoic acid; Isomer A | 373.45 |
| HP | | 2-{1-Carboxy-2-[3-(3-methyl-benzyl)-3H-imidazol-4-yl]-ethylamino}-4-methyl-pentanoic acid; Isomer B | 373.45 |
| HQ | | 2-{1-Carboxy-2-[3-(3,5-dimethyl-benzyl)-3H-imidazol-4-yl]-ethylamino}-4-methyl-pentanoic acid; Isomer A | 387.48 |
| HR | | 2-{1-Carboxy-2-[3-(3,5-dimethyl-benzyl)-3H-imidazol-4-yl]-ethylamino}-4-methyl-pentanoic acid; Isomer B | 387.48 |

| | | | |
|---|---|---|---|
| HS | | 2-{1-Carboxy-2-[3-(4-trifluoromethoxy-benzyl)-3H-imidazol-4-yl]-ethylamino}-4-methyl-pentanoic acid; Isomer A | 443.42 |
| HT | | 2-{1-Carboxy-2-[3-(4-trifluoromethoxy-benzyl)-3H-imidazol-4-yl]-ethylamino}-4-methyl-pentanoic acid; Isomer B | 443.42 |
| HU | | 2-{1-Carboxy-2-[3-(4-isopropyl-benzyl)-3H-imidazol-4-yl]-ethylamino}-4-methyl-pentanoic acid; Isomer A | 401.51 |
| HV | | 2-{1-Carboxy-2-[3-(4-isopropyl-benzyl)-3H-imidazol-4-yl]-ethylamino}-4-methyl-pentanoic acid; Isomer B | 401.51 |

TABLE 2-continued
| | | | |
|---|---|---|---|
| HW | 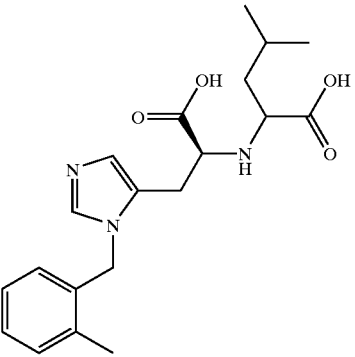 | 2-{1-Carboxy-2-[3-(2-methyl-benzyl)-3H-imidazol-4-yl]-ethylamino}-4-methyl-pentanoic acid; Isomer A | 373.45 |
| HX | 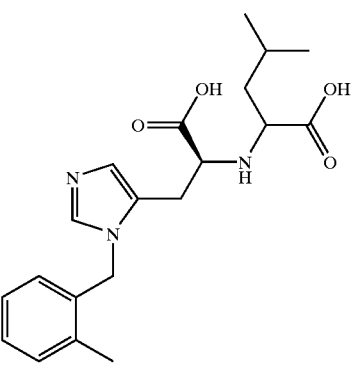 | 2-{1-Carboxy-2-[3-(2-methyl-benzyl)-3H-imidazol-4-yl]-ethylamino}-4-methyl-pentanoic acid; Isomer B | 373.45 |
| HY | 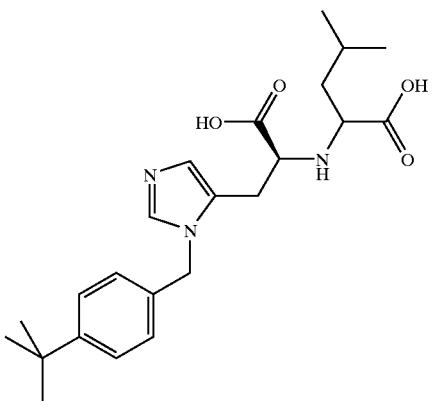 | 2-{2-[3-(4-tert-Butyl-benzyl)-3H-imidazol-4-yl]-1-carboxy-ethylamino}-4-methyl-pentanoic acid; Isomer A | 415.53 |
| HZ | 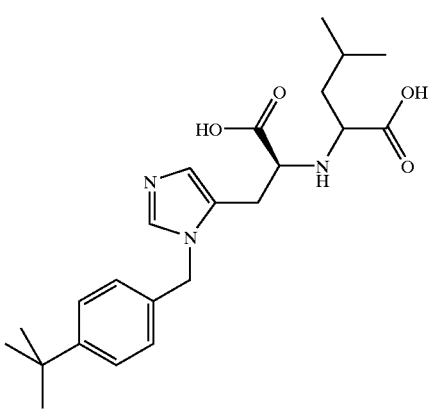 | 2-{2-[3-(4-tert-Butyl-benzyl)-3H-imidazol-4-yl]-1-carboxy-ethylamino}-4-methyl-pentanoic acid; Isomer B | 415.53 |

TABLE 2-continued

| | | | |
|---|---|---|---|
| IA | 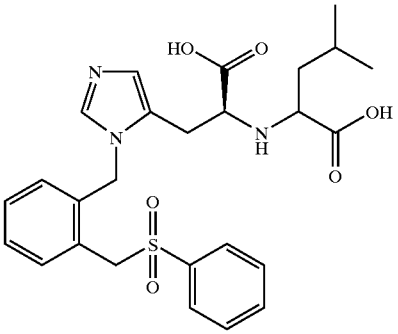 | 2-{2-[3-(2-Benzenesulfonylmethyl-benzyl)-3H-imidazol-4-yl]-1-carboxy-ethylamino}-4-methyl-pentanoic acid; Isomer A | 513.61 |
| IB | 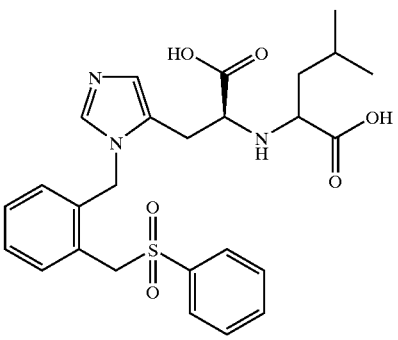 | 2-{2-[3-(2-Benzenesulfonylmethyl-benzyl)-3H-imidazol-4-yl]-1-carboxy-ethylamino}-4-methyl-pentanoic acid; Isomer B | 513.61 |
| IC | 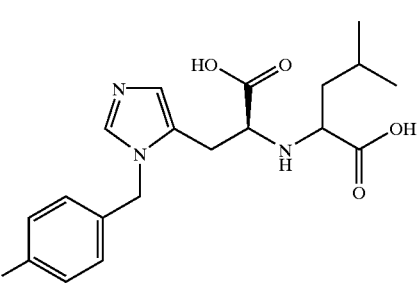 | 2-{1-Carboxy-2-[3-(4-nitro-benzyl)-3H-imidazol-4-yl]-ethylamino}-4-methyl-pentanoic acid; Isomer A | 404.42 |
| ID | 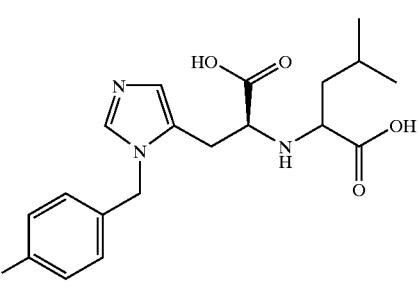 | 2-{1-Carboxy-2-[3-(4-nitro-benzyl)-3H-imidazol-4-yl]-ethylamino}-4-methyl-pentanoic acid; Isomer B | 404.42 |
| IE | 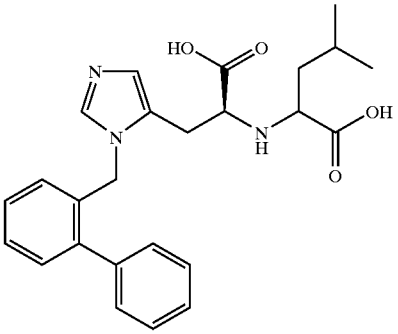 | 2-[2-(3-Biphenyl-2-ylmethyl-3H-imidazol-4-yl)-1-carboxy-ethylamino]-4-methyl-pentanoic acid; Isomer A | 435.52 |

TABLE 2-continued

| | | | |
|---|---|---|---|
| IF | 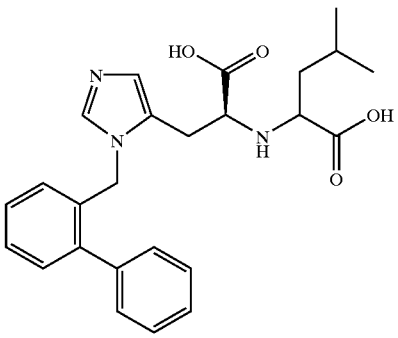 | 2-[2-(3-Biphenyl-2-ylmethyl-3H-imidazol-4-yl)-1-carboxy-ethylamino]-4-methyl-pentanoic acid; Isomer B | 435.52 |
| IG | 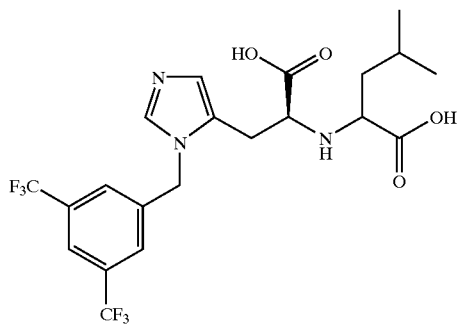 | 2-{2-[3-(3,5-Bis-trifluoromethyl-benzyl)-3H-imidazol-4-yl]-1-carboxy-ethylamino}-4-methyl-pentanoic acid; Isomer A | 495.42 |
| IH | 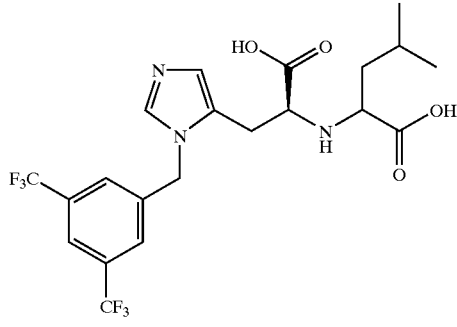 | 2-{2-[3-(3,5-Bis-trifluoromethyl-benzyl)-3H-imidazol-4-yl]-1-carboxy-ethylamino}-4-methyl-pentanoic acid; Isomer B | 495.42 |
| II | 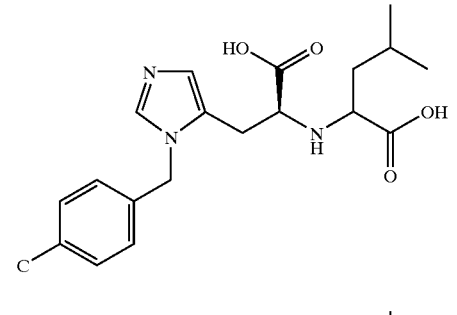 | 2-{1-Carboxy-2-[3-(4-fluoro-benzyl)-3H-imidazol-4-yl]-ethylamino}-4-methyl-pentanoic acid; Isomer A | 377.42 |
| IJ | 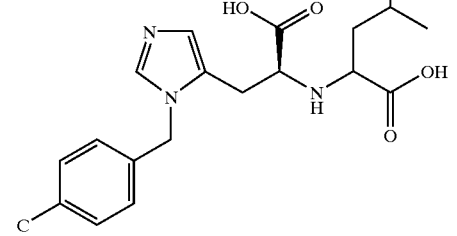 | 2-{1-Carboxy-2-[3-(4-fluoro-benzyl)-3H-imidazol-4-yl]-ethylamino}-4-methyl-pentanoic acid; Isomer B | 377.42 |

TABLE 2-continued

| | | | |
|---|---|---|---|
| IK | | 2-{1-Carboxy-2-[3-(4-fluoro-benzyl)-3H-imidazol-4-yl]-ethylamino}-4-methyl-pentanoic acid; | 284.31 |
| IL | | 2-[1-Carboxy-2-(2-phenyl-thiazol-4-yl)-ethylamino]-4-methyl-pentanoic acid | 362.45 |
| IM | | 2-[1-Carboxy-2-(5-methyl-isoxazol-3-yl)-ethylamino]-4-methyl-pentanoic acid | 284.31 |
| IN | | 2-[2-(1-Benzyl-1H-pyrazol-3-yl)-1-carboxy-ethylamino]-4-methyl-pentanoic acid | 377.42 |
| IO | | 2-{1-Carboxy-2-[3-(2,3-dimethoxy-benzyl)-3H-imidazol-4-yl]-ethylamino}-4-methyl-pentanoic acid; Isomer A | 419.48 |

TABLE 2-continued

| ID | Structure | Name | MW |
|---|---|---|---|
| IP | 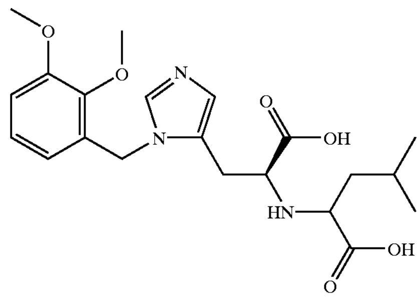 | 2-{1-Carboxy-2-[3-(2,3-dimethoxy-benzyl)-3H-imidazol-4-yl]-ethylamino}-4-methyl-pentanoic acid; Isomer B | 419.48 |
| IQ | 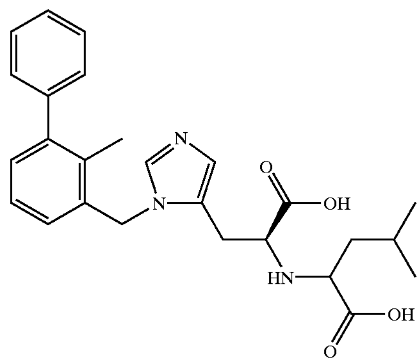 | 2-{1-Carboxy-2-[3-(2-methyl-biphenyl-3-ylmethyl)-3H-imidazol-4-yl]-ethylamino}-4-methyl-pentanoic acid; Isomer A | 449.55 |
| IR | 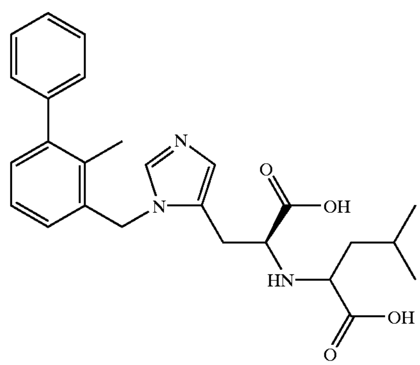 | 2-{1-Carboxy-2-[3-(2-methyl-biphenyl-3-ylmethyl)-3H-imidazol-4-yl]-ethylamino}-4-methyl-pentanoic acid; Isomer B | 449.55 |
| IS | 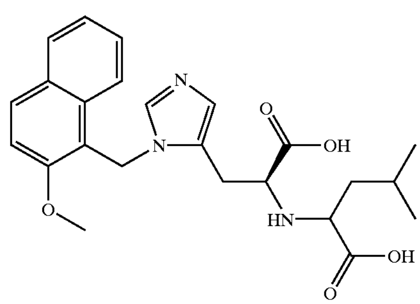 | 2-{1-Carboxy-2-[3-(2-methoxy-naphthalen-1-ylmethyl)-3H-imidazol-4-yl]-ethylamino}-4-methyl-pentanoic acid; Isomer A | 439.51 |
| IT | 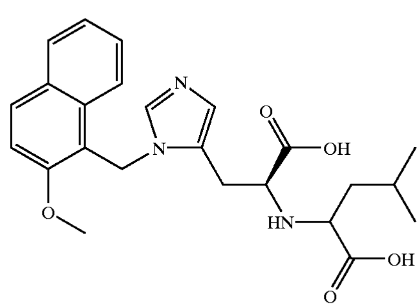 | 2-{1-Carboxy-2-[3-(2-methoxy-naphthalen-1-ylmethyl)-3H-imidazol-4-yl]-ethylamino}-4-methyl-pentanoic acid; Isomer B | 439.51 |

TABLE 2-continued

| | | | |
|---|---|---|---|
| IU | | 2-{1-Carboxy-2-[3-(2,3-difluoro-benzyl)-3H-imidazol-4-yl]-ethylamino}-4-methyl-pentanoic acid; Isomer A | 395.41 |
| IV | | 2-{1-Carboxy-2-[3-(2,3-difluoro-benzyl)-3H-imidazol-4-yl]-ethylamino}-4-methyl-pentanoic acid; Isomer A | 395.41 |
| IW | | 2-{1-Carboxy-2-[1-(2,3-difluoro-benzyl)-1H-imidazol-4-yl]-ethylamino}-4-methyl-pentanoic acid | 395.41 |
| IX | | 2-{1-Carboxy-2-[3-(2,3-dichloro-benzyl)-3H-imidazol-4-yl]-ethylamino}-4-methyl-pentanoic acid; Isomer A | 428.31 |
| IY | | 2-{1-Carboxy-2-[3-(2,3-dichloro-benzyl)-3H-imidazol-4-yl]-ethylamino}-4-methyl-pentanoic acid; Isomer B | 428.31 |
| IZ | | 2-{1-Carboxy-2-[3-(3-trifluoromethyl-benzyl)-3H-imidazol-4-yl]-ethylamino}-4-methyl-pentanoic acid; Isomer A | 427.42 |

TABLE 2-continued

| | | | |
|---|---|---|---|
| JA | 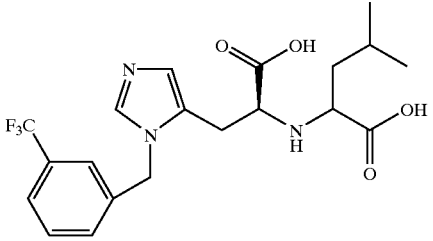 | 2-{1-Carboxy-2-[3-(3-trifluoromethyl-benzyl)-3H-imidazol-4-yl]-ethylamino}-4-methyl-pentanoic acid; Isomer B | 427.42 |
| JB | 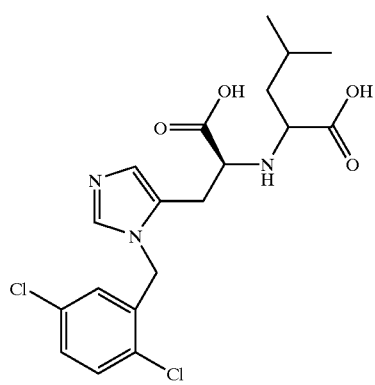 | 2-{1-Carboxy-2-[3-(2,5-dichloro-benzyl)-3H-imidazol-4-yl]-ethylamino}-4-methyl-pentanoic acid; Isomer A | 428.31 |
| JD | 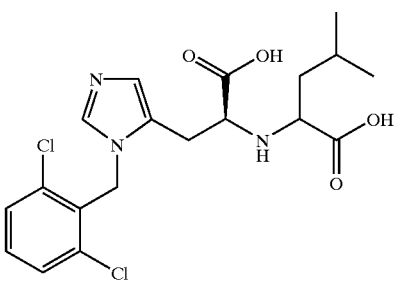 | 2-{1-Carboxy-2-[3-(2,6-dichloro-benzyl)-3H-imidazol-4-yl]-ethylamino}-4-methyl-pentanoic acid; Isomer A | 428.31 |
| JE | 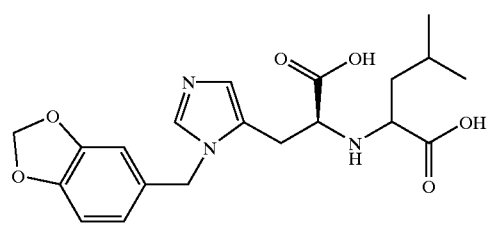 | 2-[2-(3-Benzo[1.3]dioxol-5-ylmethyl-3H-imidazol-4-yl)-1-carboxy-ethyl amino]-4-methyl-pentanoic acid; Isomer A | 403.44 |
| JF | 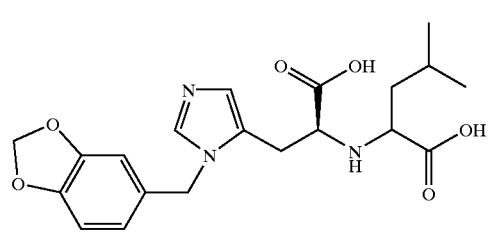 | 2-[2-(3-Benzo[1.3]dioxol-5-ylmethyl-3H-imidazol-4-yl)-1-carboxy-ethyl amino]-4-methyl-pentanoic acid; Isomer B | 403.44 |
| JG | 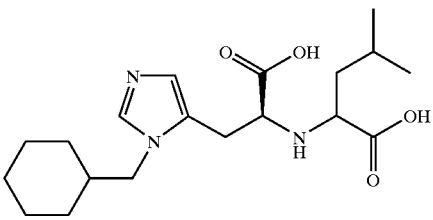 | 2-[1-Carboxy-2-(3-cyclohexylmethyl-3H-imidazol-4-yl)-ethylamino]-4-methyl-pentanoic acid; Isomer A | 365.47 |

TABLE 2-continued

| | | | |
|---|---|---|---|
| JH | | 2-[1-Carboxy-2-(3-cyclohexylmethyl-3H-imidazol-4-yl)-ethylamino]-4-methyl-pentanoic acid; Isomer B | 365.47 |
| JI | | 2-{1-Carboxy-2-[3-(2-cyclohexyl-ethyl)-3H-imidazol-4-yl]-ethylamino}-4-methyl-pentanoic acid; Isomer A | 379.50 |
| JJ | | 2-{1-Carboxy-2-[3-(2-cyclohexyl-ethyl)-3H-imidazol-4-yl]-ethylamino}-4-methyl-pentanoic acid; Isomer B | 379.50 |
| JK | | 2-[1-Carboxy-2-(3-phenethyl-3H-imidazol-4-yl)-ethylamino]-4-methyl-pentanoic acid; Isomer[001b] A | 373.45 |
| JL | | 2-[1-Carboxy-2-(3-phenethyl-3H-imidazol-4-yl)-ethylamino]-4-methyl-pentanoic acid; Isomer B | 373.45 |
| JM | | 2-{1-Carboxy-2-[3-(2-ethyl-butyl)-3H-imidazol-4-yl]-ethylamino}-4-methyl-pentanoic acid; Isomer A | 353.46 |
| JN | | 2-{1-Carboxy-2-[3-(2-ethyl-butyl)-3H-imidazol-4-yl]-ethylamino}-4-methyl-pentanoic acid; Isomer B | 353.46 |

TABLE 2-continued

| | | | |
|---|---|---|---|
| JO | | 2-{1-Carboxy-2-[3-(3-iodo-benzyl)-3H-imidazol-4-yl]-ethylamino}-4-methyl-pentanoic acid; Isomer A | 531.35 |
| JP | | 2-{1-Carboxy-2-[3-(3-iodo-benzyl)-3H-imidazol-4-yl]-ethylamino}-4-methyl-pentanoic acid; Isomer B | 531.35 |
| JQ | | 2-{1-Carboxy-2-[3-(3-fluoro-benzyl)-3H-imidazol-4-yl]-ethylamino}-4-methyl-pentanoic acid; Isomer A | 423.45 |
| JR | | 2-{1-Carboxy-2-[3-(3-fluoro-benzyl)-3H-imidazol-4-yl]-ethylamino}-4-methyl-pentanoic acid; Isomer B | 423.45 |
| JZ | | 2-[2-(2-Benzyl-thiazol-4-yl)-1-carboxy-ethylamino]-4-methyl-pentanoic acid; Isomer A | |

TABLE 2-continued

| Ref. | | | |
|---|---|---|---|
| KA | [structure] | | 2-[2-(2-Benzyl-thiazol-4-yl)-1-carboxy-ethylamino]-4-methyl-pentanoic acid; Isomer B |
| KB | [structure] | | 2-[2-(5-Benzyl-2-methyl-thiazol-4-yl)-1-carboxy-ethylamino]-4-methyl-pentanoic acid; Isomer A |
| KC | [structure] | | 2-[2-(5-Benzyl-2-methyl-thiazol-4-yl)-1-carboxy-ethylamino]-4-methyl-pentanoic acid; Isomer B |

| Ref. No. | Human ACE-2 Activity | RAT ACE-2 Activity | ACE Activity | Carboxypeptidase A Activity | CHN Expected | CHN Actual |
|---|---|---|---|---|---|---|
| A | * | | | | | |
| B | * | | | | | |
| C | * | | *** | | | |
| D | * | | *** | | % C 65.51, % H 7.90, % N 4.77 | % C 65.56, % H 7.82, % N 4.68 |
| E | * | * | *** | *** | % C 46.44, % H 5.60, % N 3.39 (NaCl) | % C 4.64, % H 5.65, % N 2.94 (NaCl) |
| G | * | | *** | | | |
| H | * | | | | | |
| I | * | | | | | |
| J | * | | | | | |
| K | * | | | | | |
| L | * | | | | | |
| M | * | | | | | |
| N | ** | | *** | *** | % C 44.74, % H 6.09, % N 17.39 (0.8 H2O) | % C 44.96, % H 5.71, % N 17.69 (0.8 H2O) |
| O | * | | | | % C 58.96, % H 6.51, % N 5.73 (0.4 H2O) | % C 59.16, % H 6.37, % N 5.28 (0.4 H2O) |
| P | * | | *** | *** | | |
| Q | ** | | *** | *** | | |
| R | * | * | *** | *** | | |
| T | * | | *** | ** | | |
| U | ** | * | *** | *** | | |
| V | * | | *** | *** | % C 66.43, % H 8.20, % N 4.56 | % C 66.36, % H 8.17, % N 4.37 |
| W | * | | *** | *** | % C 59.80, % H 6.12, % N 9.30 (0.3 H2O) | % C 59.68, % H 5.98, % N 9.26 (0.3 H2O) |
| X | * | | *** | *** | % C 56.09, % H 6.24, % N 8.18 (1 HCl, 0.1 H2O) | % C 55.99, % H 5.89, % N 7.79 (1 HCl, 0.1 H2O) |

TABLE 2-continued

| | | | | | |
|---|---|---|---|---|---|
| Y | ** | *** | *** | % C 54.66, % H 6.57, % N 4.25 (0.5 HCl) | % C 54.95, % H 6.54, % N 4.12 (0.5 HCl) |
| Z | * | *** | *** | % C 45.59, % H 7.31, % N 5.91 (0.1 H2O) | % C 45.37, % H 7.09, % N 5.83 (0.1 H2O) |
| AA | ** | *** | *** | % C 62.53, % H 7.27, % N 5.21 (0.2 H2O) | % C 62.91, % H 6.99, % N 5.24 (0.2 H2O) |
| AB | * | *** | *** | | |
| AC | * | *** | *** | % C 60.96, % H 6.65, % N 4.74 (0.5 HCl) | % C 60.80, % H 6.77, % N 4.30 (0.5 HCl) |
| AD | ** | *** | *** | % C 43.33, % H 6.18, % N 17.18 (0.8 HCl, 0.4 NH3) | % C 43.54, % H 5.55, % N 16.78 (0.8 HCl, 0.4 NH3) |
| AE | ** | *** | *** | | |
| AF | ** | *** | *** | % C 45.29, % H 6.22, % N 14.40 (1 HCl) | % C 45.12, % H 6.01, % N 14.04 (1 HCl) |
| AG | * | *** | *** | % C 59.31, % H 5.97, % N 9.88 (0.4 H2O) | % C 58.97, % H 5.59, % N 9.66 (0.4 H2O) |
| AH | * | *** | *** | % C 48.65, % H 5.47, % N 5.67 (0.2 H2O) | % C 48.27, % H 5.22, % N 5.32 (0.2 H2O) |
| AI | ** | *** | *** | % C 53.12, % H 6.32, % N 5.16 | % C 53.23, % H 6.15, % N 5.10 |
| AJ | ** | *** | ** | % C 68.94, % H 6.42, % N 4.23 (0.1 HCl) | % C 68.88, % H 6.46, % N 3.95 (0.1 HCl) |
| AK | * | *** | *** | | |
| AL | ** | *** | *** | % C 50.23, % H 6.39, % N 4.51 (0.7 HCl) | % C 50.56, % H 6.26, % N 4.55 (0.7 HCl) |
| AM | * | *** | *** | % C 39.24, % H 6.55, % N 6.29 (0.6 HCl, 0.1 NH3) | % C 39.41, % H 6.35, % N 6.22 (0.6 HCl, 0.1 NH3) |
| AN | ** | *** | ** | % C 47.41, % H 8.57, % N 9.55 (0.9 NH3) | % C 47.57, % H 8.66, % N 9.37 (0.9 NH3) |
| AO | * | *** | *** | % C 43.70, % H 7.22, % N 5.10 (0.7 HCl) | % C 43.78, % H 6.81, % N 5.30 (0.7 HCl) |
| AP | *** | ** | *** | ** | % C 59.0, % N 12.4, % H 8.3 (as NH4 salt) M+1 309, M−1 307 | % C 58.7, % N 11.9, % H 8.3 M+1 309, M−1 307 |
| AQ | * | *** | *** | | |
| AR | * | *** | *** | | |
| AS | * | * | *** | *** | % C 64.50, % H 7.58, % N 5.01 | % C 64.02, % H 7.23, % N 4.60 |
| AT | * | *** | *** | | ND |
| AU | * | *** | *** | | ND |
| AV | * | * | *** | ** | | |
| AW | * | *** | *** | % C 58.52, % H 7.37, % N 8.92 (0.2 H2O, 0.7 NH3) | % C 58.71, % H 7.56, % N 8.86 (0.2 H2O, 0.7 NH3) |

TABLE 2-continued

| | | | | | | |
|---|---|---|---|---|---|---|
| AX | * | | *** | *** | % C 63.92,<br>% H 7.78,<br>% N 4.66<br>(0.2 HCl) | % C 63.85,<br>% H 7.56,<br>% N 5.01<br>(0.2 HCl) |
| AZ | * | * | *** | *** | % C 54.26,<br>% H 5.66,<br>% N 4.52<br>(0.4 HCl) | % C 54.24,<br>% H 5.74,<br>% N 4.45<br>(0.4 HCl) |
| BA | * | * | *** | *** | | |
| BB | ** | * | * | *** | | |
| BC | ** | * | ** | *** | % C 50.05,<br>% H 6.99,<br>% N 17.51<br>(0.2 H2O,<br>0.3 NH3) | % C 49.97,<br>% H 7.18,<br>% N 17.70<br>(0.2 H2O,<br>0.3 NH3) |
| BD | ** | * | *** | *** | % C 45.76,<br>% H 5.97,<br>% N 17.79<br>(0.5 H2O) | % C 46.10,<br>% H 5.71,<br>% N 17.38<br>(0.5 H2O) |
| BE | ** | * | ** | *** | % C 52.04,<br>% H 7.41,<br>% N 17.45<br>(0.5 NH3) | % C 51.71,<br>% H 7.33,<br>% N 17.22<br>(0.5 NH3) |
| BF | ** | ** | *** | *** | | |
| BG | * | | *** | *** | | |
| BH | * | | *** | *** | % C 64.70,<br>% H 7.84,<br>% N 4.72<br>(0.1 HCl) | % C 64.56,<br>% H 7.28,<br>% N 4.45<br>(0.1 HCl) |
| BI | * | * | *** | *** | % C 50.96,<br>% H 6.93,<br>% N 14.38<br>(0.3 HCl,<br>0.2 MeCOOH) | % C 51.39,<br>% H 6.40,<br>% N 13.98<br>(0.3 HCl,<br>0.2 MeCOOH) |
| BJ | ** | * | ** | *** | % C 50.90,<br>% H 6.90,<br>% N 14.84<br>(0.4 HCl) | % C 51.39,<br>% H 6.40,<br>% N 14.96<br>(0.4 HCl) |
| BK | ** | ** | *** | *** | % C 52.94,<br>% H 7.09,<br>% N 14.94<br>(0.2 MeCOOH) | % C 52.63,<br>% H 6.76,<br>% N 14.56<br>(0.2 MeCOOH) |
| BL | ** | * | ** | *** | % C 52.27,<br>% H 7.04,<br>% N 14.75<br>(0.2 MeCOOH,<br>0.1 HCl) | % C 53.39,<br>% H 6.63,<br>% N 14.39<br>(0.2 MeCOOH,<br>0.1 HCl) |
| BN | * | | *** | *** | % C 48.79,<br>% H 4.47,<br>% N 4.38<br>(DISODIUM<br>SALT,<br>1.6 H2O) | % C 48.47,<br>% H 4.03,<br>% N 4.08<br>(DISODIUM<br>SALT,<br>1.6 H2O) |
| BO | * | | *** | ** | % C 53.32,<br>% H 5.11,<br>% N 3.66<br>(DISODIUM<br>SALT,<br>2.2 H2O) | % C 53.10,<br>% H 4.83,<br>% N 3.38<br>(DISODIUM<br>SALT,<br>2.2 H2O) |
| BP | * | | *** | *** | % C 59.73,<br>% H 7.08,<br>% N 4.10<br>(HCl salt) | % C 59.70,<br>% H 7.58,<br>% N 4.0 |
| BQ | * | * | *** | *** | | |
| BR | * | * | *** | *** | | |
| BS | ** | * | *** | *** | % C 59.3,<br>% N 4.9,<br>% H 6.9<br>(as 0.5 HCl salt)<br>M+1 266,<br>M−1 264 | % C 58.7,<br>% N 4.2,<br>% H 6.8<br>(as 0.5 HCl salt)<br>M+1 266,<br>M−1 264 |
| BT | * | * | *** | *** | % C 59.3,<br>% N 4.9,<br>% H 6.9<br>(as 0.5 HCl salt)<br>M+1 266,<br>M−1 264 | % C 58.5,<br>% N 4.2,<br>% H 6.8<br>(as 0.5 HCl salt)<br>M+1 266,<br>M−1 264 |

TABLE 2-continued

| | | | | | | |
|---|---|---|---|---|---|---|
| BU | ** | * | *** | *** | % C 58.88, % H 8.03, % N 8.58 | % C 58.76, % H 7.94, % N 8.40 |
| BV | ** | * | ** | * | | |
| BW | * | ** | *** | ** | | |
| BX | * | | *** | *** | | |
| BY | * | | *** | *** | | |
| BZ | * | * | *** | *** | % C 58.18, % H 7.43, % N 11.15 (0.2 H2O, 0.3 NH3) | % C 58.01, % H 7.03, % N 10.95 (0.2 H2O, 0.3 NH3) |
| CA | * | * | *** | *** | % C 52.41, % H 7.24, % N 14.10 (0.4 HCl) | % C 52.57, % H 6.87, % N 13.93 (0.4 HCl) |
| CB | ** | * | *** | *** | % C 52.80, % H 7.53, % N 15.63 (0.2 HCl, 0.3 NH3) | % C 52.49, % H 7.50, % N 15.58 (0.2 HCl, 0.3 NH3) |
| CC | * | * | *** | *** | % C 57.44, % H 7.27, % N 11.01 (0.2 HCl, 0.3 NH3) | % C 57.20, % H 7.02, % N 10.83 (0.2 HCl, 0.3 NH3) |
| CD | ** | ** | *** | *** | % C 46.98, % H 6.56, % N 19.92 (0.3 HCl) | % C 47.22, % H 6.43, % N 19.87 (0.3 HCl) |
| CE | ** | * | *** | *** | % C 45.91, % H 7.00, % N 22.39 (0.2 HCl, 0.6 NH3) | % C 45.85, % H 6.62, % N 22.65 (0.2 HCl, 0.6 NH3) |
| CF | ** | ** | *** | *** | % C 47.74, % H 6.74, % N 12.53 (0.1 HCl, 0.7 NH3) | % C 47.57, % H 6.49, % N 12.41 (0.1 HCl, 0.7 NH3) |
| CG | * | | *** | *** | % C 53.14, % H 8.92, % N 8.06 (0.1 HCl, 0.3 NH3) | % C 53.03, % H 8.75, % N 7.77 (0.1 HCl, 0.3 NH3) |
| CH | * | | *** | *** | % C 60.53, % H 7.90, % N 3.92 (1 HCl) | % C 60.88, % H 7.66, % N 3.76 (1 HCl) |
| CI | * | | *** | *** | % C 65.28, % H 8.25, % N 4.48 (0.3 H2O) | % C 65.17, % H 8.16, % N 4.70 (0.3 H2O) |
| CJ | * | * | *** | *** | % C 60.55, % H 7.28, % N 4.71 (0.5 HCl) | % C 60.25, % H 7.68, % N 4.49 (0.5 HCl) |
| CK | ** | ** | *** | *** | % C 66.04, % H 8.22, % N 4.53 (0.1 H2O) (LOT 1) % C 66.43, % H 8.20, % N 4.56 | % C 65.63, % H 8.28, % N 4.36 (0.1 H2O) (LOT 1) % C 66.40, % H 8.32, % N 4.57 |
| CL | ** | ** | *** | *** | % C 62.82, % H 7.05, % N 4.58 (0.4 HCl) | % C 63.07, % H 6.88, % N 4.51 (0.4 HCl) |
| CM | *** | | *** | *** | | |
| CN | * | | *** | *** | % C 61.3, % N 5.1, % H 7.4 (as monohydrate) | % C 61.9, % N 5.0, % H 7.4 (as monohydrate) |
| CO | * | | *** | *** | % C 43.96, % H 7.24, % N 12.18 (2 MeCOOH, 1.8 NH3) | % C 44.02, % H 6.99, % N 12.11 (2 MeCOOH, 1.8 NH3) |

TABLE 2-continued

| | | | | | | |
|---|---|---|---|---|---|---|
| CP | * | * | *** | ** | % C 52.70, % H 6.79, % N 5.39, % Cl 1.56, % S 10.82 (0.21 H2O, 0.13 HCl, 0.14 NH3) | % C 52.31, % H 6.63, % N 5.23, % Cl 1.76, % S 11.27 (0.21 H2O, 0.13 HCl, 0.14 NH3) |
| CQ | * | | *** | *** | % C 59.91, % H 7.57, % N 6.52 (0.4 HCl, 0.4 NH3) | % C 59.75, % H 7.25, % N 6.77 (0.4 HCl, 0.4 NH3) |
| CR | * | * | *** | *** | % C 54.95, % H 7.81, % N 13.35 (0.3 H2O, 0.2 MeCOOH) | % C 55.08, % H 7.70, % N 12.97 (0.3 H2O, 0.2 MeCOOH) |
| CS | * | | *** | *** | % C 55.87, % H 7.83, % N 3.83 (1.2 H2O, 1 HCl) | % C 55.66, % H 7.64, % N 3.76 (1.2 H2O, 1 HCl) |
| CT | * | * | *** | *** | % C 48.87, % H 7.64, % N 12.21 (1 H2O, 1.2 MeCOOH, 0.3 NH3) | % C 48.71, % H 7.78, % N 12.12 (1 H2O, 1.2 MeCOOH, 0.3 NH3) |
| CU | ** | ** | *** | *** | % C 52.41, % H 7.46, % N 11.18 (1.1 MeCOOH, 0.3 EtOAc) | % C 52.26, % H 7.69, % N 11.52 (1.1 MeCOOH, 0.3 EtOAc) |
| CV | * | * | *** | *** | % C 47.98, % H 7.22, % N 12.34, % S 9.42 (0.1 H2O, 1 NH3, 0.4 EtOAc) | % C 47.69, % H 6.92, % N 11.70, % S 9.66 (0.1 H2O, 1 NH3, 0.4 EtOAc) |
| CW | * | * | *** | *** | | |
| CX | ** | * | ** | *** | % C 56.18, % H 6.76, % N 11.03 (1 HCl, 0.3 NH3, 0.3 MeCOOH) | % C 56.25, % H 6.97, % N 11.19 (1 HCl, 0.3 NH3, 0.3 MeCOOH) |
| CY | * | | *** | *** | % C 72.2, % N 5.6, % H 9.2 | % C 72.2, % N 5.6, % H 9.2 |
| CZ | * | | *** | *** | C, 68.74; H, 8.94; N, 4.01 | C, 68.20; H, 8.90; N, 3.93 |
| DA | * | | *** | *** | C, 68.74; H, 8.94; N, 4.01 | C, 68.23; H, 8.85; N, 3.99 |
| DB | * | | *** | *** | | |
| DC | * | | *** | *** | | |
| DD | * | * | *** | *** | % C 56.70, % H 8.51, % N 6.96 (3 H2O, MeCN) | % C 56.92, % H 8.13, % N 7.23, % Cl 0.0 (3 H2O, MeCN) |
| DE | * | * | *** | *** | % C 62.82, % H 7.05, % N 4.58 (0.4 HCl) | % C 63.09, % H 7.09, % N 4.49 (0.4 HCl) |
| DF | * | | *** | *** | % C 64.73, % H, 7.97, % N 10.06 | % C 64.75, % H, 7.867, % N 9.95 |
| DG | * | | *** | *** | | |
| DH | * | * | *** | *** | | |
| DI | * | * | *** | ** | % C 68.16, % H, 7.32, % N 6.36 | % C 68.19, % H, 7.16, % N 6.31 |

TABLE 2-continued

| | | | | | | |
|---|---|---|---|---|---|---|
| DJ | * | ** | *** | *** | % C 46.97, % H 6.96, % N 12.84 (1 H2O, 0.9 MeCOOH) | % C 46.60, % H 7.29, % N 13.06 (1 H2O, 0.9 MeCOOH) |
| DK | ** | * | ** | *** | % C 49.35, % H 6.86, % N 14.89 (0.5 H2O, 0.3 MeCOOH) | % C 49.23, % H 6.72, % N 14.63 (0.5 H2O, 0.3 MeCOOH) |
| DL | ** | * | *** | *** | % C 59.05, % H 7.30, % N 10.87 (1.5 H2O) | % C 59.02, % H 7.03, % N 11.08 (1.5 H2O) |
| DM | ** | * | *** | ** | % C 58.77, % H 7.32, % N 11.54 (1 H2O, 0.3 MeCOOH, 0.3 NH3) | % C 58.60, % H 6.96, % N 11.28 (1 H2O, 0.3 MeCOOH, 0.3 NH3) |
| DN | ** | * | *** | *** | | |
| DO | ** | ** | ** | *** | % C 49.39, % H 5.25, % N 11.25 (0.5 H2O, 1 HCl) | % C 49.21, % H 5.55, % N 11.55 (0.5 H2O, 1 HCl) |
| DP | ** | ** | ** | *** | % C 59.88, % H 6.09, % N 13.09 (0.2 H2O) | % C 59.97, % H 6.04, % N 13.07 (0.2 H2O) |
| DQ | ** | ** | *** | *** | | |
| DR | * | | *** | ** | | |
| DS | * | ** | *** | ** | | |
| DT | * | ** | *** | ** | | |
| DU | * | | *** | ** | | |
| DV | * | | *** | * | | |
| DW | * | | *** | * | | |
| DX | *** | ** | *** | *** | % C 53.21, % H 6.47, % N 9.31 (1 H2O, 2 Na) | % C 53.60, % H 6.47, % N 9.20 (1 H2O, 2 Na) |
| DY | * | | *** | *** | % C 47.01, % H 8.65, % N 15.27 (1.5 H2O, 1.5 MeCOOH, 0.9 NH3) | % C 47.26, % H 8.24, % N 15.30 (1.5 H2O, 1.5 MeCOOH, 0.9 NH3) |
| DZ | * | | *** | *** | % C 52.31, % H 8.56, % N 15.51 (1.2 H2O, 0.4 MeCOOH) | % C 52.02, % H 8.25, % N 15.92 (1.2 H2O, 0.4 MeCOOH) |
| EA | ** | ** | *** | * | | |
| EB | * | * | *** | ** | | |
| EC | ** | * | ** | * | % C 51.48, % H 6.96, % N 12.64 (1.8 H2O, 1 NH3) | % C 51.56, % H 6.94, % N 12.29 (1.8 H2O, 1 NH3) |
| ED | ** | ** | *** | *** | % C 47.21, % H 7.59, % N 13.76 (2 H2O) | % C 47.06, % H 7.66, % N 13.94 (2 H2O) |
| EF | ** | * | ** | *** | % C 47.92, % H 7.58, % N 15.04 (1 H2O, 0.5 MeCOOH, 0.5 NH3) | % C 47.76, % H 7.43, % N 14.72 (1 H2O, 0.5 MeCOOH, 0.5 NH3) |
| EG | ** | * | ** | *** | % C 43.30, % H 6.02, % N 17.28 (2 H2O, 0.5 MeCOOH, 1.5 NH3) | % C 43.06, % H 6.34, % N 17.07 (2 H2O, 0.5 MeCOOH, 1.5 NH3) |

TABLE 2-continued

| | | | | | | |
|---|---|---|---|---|---|---|
| EH | * | * | *** | *** | % C 48.84, % H 6.29, % N 4.48 (0.1 H2O, 0.1 NH3, 1 NaCl) | % C 48.69, % H 6.26, % N 4.85 (0.1 H2O, 0.1 NH3, 1 NaCl) |
| EI | * | | *** | *** | % C 47.62, % H 5.79, % N 3.97 (0.7 H2O, 2 Na) | % C 47.23, % H 6.10, % N 4.37 (0.7 H2O, 2 Na) |
| EJ | * | | *** | *** | % C 50.59, % H 6.37, % N 4.21 (2 Na) | % C 50.53, % H 6.22, % N 4.57 (2 Na) |
| EK | ** | | ** | ** | | |
| EL | * | ** | *** | ** | | |
| EM | * | * | *** | *** | | |
| EN | *** | ** | *** | *** | % C 54.83, % H 7.45, % N 9.59 (2.7 H2O) | % C 54.87, % H 7.65, % N 9.57 (2.7 H2O) |
| EO | ** | * | *** | *** | % C 56.94, % H 7.31, % N 9.96 (1.8 H2O) | % C 57.09, % H 7.61, % N 10.33 (1.8 H2O) |
| EQ | ** | ** | *** | ** | % C 53.75, % H 6.07, % N 11.19 (1 H2O, 0.9 MeCOOH) | % C 53.25, % H 5.69, % N 11.59 (1 H2O, 0.9 MeCOOH) |
| ER | ** | ** | *** | *** | % C 58.56, % H 6.20, % N 12.81 (0.6 H2O) | % C 58.44, % H 5.96, % N 12.68 (0.6 H2O) |
| ES | * | | *** | *** | % C 53.47, % H 7.55, % N 14.17 (0.4 H2O, 0.1 MeCOOH) | % C 53.80, % H 7.34, % N 13.82 (0.4 H2O, 0.1 MeCOOH) |
| ET | * | | *** | *** | | |
| EU | * | * | *** | ** | | |
| EV | ** | * | *** | *** | % C 52.29, % H 7.51, % N 19.53 (0.4 MeCOOH, 0.1 NH3) | % C 52.36, % H 7.32, % N 19.42 (0.4 MeCOOH, 0.1 NH3) |
| EW | * | * | *** | *** | % C 43.24, % H 7.83, % N 14.90 (5 MeCOOH, 2.5 NH3) | % C 43.01, % H 7.71, % N 14.68 (5 MeCOOH, 2.5 NH3) |
| EX | * | * | *** | *** | % C 50.18, % H 6.51, % N 15.96 (2 MeCOOH, 1 NH3) | % C 50.01, % H 6.39, % N 15.74 (2 MeCOOH, 1 NH3) |
| EY | * | * | *** | *** | % C 52.20, % H 6.21, % N 15.51 (1.4 MeCOOH, 0.3 NH3) | % C 52.08, % H 6.33, % N 15.61 (1.4 MeCOOH, 0.3 NH3) |
| EZ | *** | *** | *** | *** | % C 58.66, % H 7.14, % N 10.06 (0.9 H2O, 0.7 MeCOOH) | % C 58.86, % H 7.54, % N 9.71 (0.9 H2O, 0.7 MeCOOH) |
| FA | * | | *** | *** | % C 56.43, % H 7.34, % N 11.86 (1.6 MeCOOH, 1 NH3) | % C 56.42, % H 7.41, % N 11.99 (1.6 MeCOOH, 1 NH3) |
| FB | * | | *** | *** | % C 58.06, % H 6.94, % N 8.99 (1.3 MeCOOH) | % C 58.46, % H 7.06, % N 8.70 (1.3 MeCOOH) |

TABLE 2-continued

| | | | | | | |
|---|---|---|---|---|---|---|
| FC | * | * | *** | *** | | |
| FD | * | * | * | *** | | |
| FE | ** | * | ** | *** | | |
| FG | * | * | *** | *** | | |
| FH | * | * | *** | *** | | |
| FI | * | | *** | *** | | |
| FJ | * | | *** | *** | | |
| FK | * | * | *** | *** | % C 61.54, % H 7.56, % N 12.94 (0.2 H2O, 0.2 HCO2H) | % C 61.31, % H 7.48, % N 13.49 |
| FL | * | * | *** | *** | % C 61.43, % H 7.61, % N 12.93 (0.3 H2O, 0.2 HCO2H) | % C 61.05, % H 7.49, % N 13.43 |
| FM | * | | *** | *** | % C 61.54, % H 7.25, % N 10.79 (0.2 H2O, 0.3 HCO2H) | % C 66.65, % H 7.31, % N 10.99 |
| FN | * | | *** | *** | | |
| FO | * | * | *** | *** | | |
| FP | * | | *** | *** | | |
| FQ | ** | | *** | ** | % C 63.19, % H 5.80, % N 3.65 (0.1 MeCN) | % C 62.88, % H 5.90, % N 3.85 |
| FR | * | | *** | *** | % C 63.14, % H 5.82, % N 3.94 (0.2 MeCN) | % C 63.53, % H 5.95, % N 4.20 |
| FS | ** | *** | *** | ** | | |
| FT | * | * | *** | *** | | |
| FU | * | * | *** | *** | | |
| FV | * | * | *** | *** | | |
| FW | ** | * | *** | *** | | |
| FX | * | * | *** | *** | | |
| FY | *** | *** | *** | *** | | |
| FZ | ** | * | *** | *** | | |
| GA | *** | *** | *** | ** | | |
| GB | ** | ** | *** | *** | | |
| GC | ** | ** | *** | ** | | |
| GD | * | * | *** | *** | | |
| GE | * | * | *** | *** | | |
| GF | *** | ** | *** | * | | |
| GG | *** | *** | *** | *** | | |
| GH | ** | ** | *** | *** | | |
| GI | *** | *** | *** | ** | % C 51.21, % H 6.16, % N 8.60 (2.0 H2O, 0.2 MeCOOH) | % C 51.53, % H 6.11, % N 8.84 (2.0 H2O, 0.2 MeCOOH) |
| GJ | ** | * | ** | ** | % C 51.71, % H 5.55, % N 9.32 (1.0 HCl) | % C 51.78, % H 5.43, % N 9.06 (1.0 HCl) |
| GK | *** | *** | *** | ** | | |
| GL | *** | *** | ** | ** | | |
| GM | *** | *** | *** | ** | % C 54.03, % H 6.35, % N 9.01 (1.3 H2O) | % C 54.12, % H 6.47, % N 9.37 (1.3 H2O) |
| GN | *** | | *** | *** | % C 54.91, % H 6.13, % N 9.66 (0.5 H2O, 0.5 HCOOH, 0.7 MeOH) | % C 54.69, % H 6.43, % N 10.07 (0.5 H2O, 0.5 HCOOH, 0.7 MeOH) |
| GO | * | | *** | *** | | |
| GP | *** | | *** | *** | | |
| GQ | ** | | | | % C 57.47, % H 5.78, % N 7.57 (0.4 HCl) | % C 57.34, % H 5.99, % N 7.43 (0.4 HCl) |
| GR | * | | | | | |
| GS | ** | | | | | |
| GT | * | | | | | |

TABLE 2-continued

| | | | | | | |
|---|---|---|---|---|---|---|
| GU | ** | | | | C, 43.7%, H, 6.15%, N, 12.34% (0.8 HCl) | C12H19N 3O4S 0.8 HCl requires: C, 43.61%, H, 6.04%, N, 12.71% |
| GV | * | | | | C, 44.45%; H, 6.34%; N, 12.87% | C12H19N 3O4S.0.6 HCl requires: C, 44.59%; H, 6.11%; N, 13.00% |
| GW | *** | *** | ** | ** | % C 52.32, % H 6.34, % N 10.72 (0.6 NH3, 0.5 EtOAc) | % C 52.27, % H 6.02, % N 10.45 (0.6 NH3, 0.5 EtOAc) |
| GX | ** | | | | % C 51.74, % H 5.55, % N 8.96, % Cl 14.01 (0.9 H2O, 0.1 EtOAc) does not match | % C 51.40, % H 5.69, % N 9.27, % Cl 15.04 (0.9 H2O, 0.1 EtOAc) |
| GY | ** | | | | C, 51.98%; H, 6.74%; N, 9.23% | % C, 51.98; % H 6.71; % N 9.33% |
| GZ | * | | | | C, 52.02%; H, 6.70%; N, 9.24% | C, 51.98%; H, 6.71%; N, 9.33% |
| HA | *** | | ** | ** | | |
| HB | ** | | | | | |
| HC | *** | *** | ** | ** | % C 54.67, % H 5.91, % N 10.22 (0.7 H2O, 0.3 HCOOH) | % C 54.92, % H 6.26, % N 9.96 (0.7 H2O, 0.3 HCOOH) |
| HD | *** | | | | % C 56.25, % H 6.00, % N 10.08 (0.5 H2O) | % C 56.64, % H 6.25, % N 10.43 (0.5 H2O) |
| HE | *** | *** | ** | ** | % C 51.30, % H 5.44, % N 9.24 (1.0 H2O) | % C 51.13, % H 5.65, % N 9.41 (1.0 H2O) |
| HF | *** | | | | % C 51.29, % H 5.43, % N 9.37 (1.0 H2O) | % C 51.13, % H 5.65, % N 9.41 (1.0 H2O) |
| HG | *** | *** | ** | ** | % C 60.03, % H 7.08, % N 10.44 (1.0 H2O, 0.3 HCOOH) | % C 61.16, % H 7.36, % N 10.37 (1.0 H2O, 0.3 HCOOH) |
| HH | ** | | | | % C 60.93, % H 7.15, % N 10.52 (0.8 H2O, 0.2 HCOOH) | % C 61.10, % H 7.36, % N 10.58 (0.8 H2O, 0.2 HCOOH) |
| HI | *** | | | | | |
| HJ | ** | | | | | |
| HK | *** | *** | ** | ** | % C 60.31, % H 7.24, % N 9.43 (1.0 H2O, 0.5 HCOOH) | % C 60.26, % H 7.53, % N 9.81 (1.0 H2O, 0.5 HCOOH) |
| HL | ** | | | | % C 62.06, % H 7.42, % N 10.16 (1.0 H2O) | % C 62.20, % H 7.71, % N 10.36 (1.0 H2O) |
| HM | ** | | | | | |
| HN | * | | | | | |
| HO | *** | *** | ** | ** | % C 60.87, % H 7.11, % N 10.54 (1.1 H2O) | % C 61.08, % H 7.48, % N 10.68 (1.1 H2O) |

TABLE 2-continued

| | | | | | | |
|---|---|---|---|---|---|---|
| HP | *** | | | | % C 61.03, % H 7.24, % N 10.71 (1.0 H2O) | % C 61.36, % H 7.47, % N 10.73 (1.0 H2O) |
| HQ | *** | *** | ** | ** | % C 61.71, % H 7.41, % N 10.24 (1.0 H2O, 0.3 HCOOH) | % C 61.01, % H 7.60, % N 10.02 (1.0 H2O, 0.3 HCOOH) |
| HR | *** | | | | % C 62.50, % H 7.40, % N 10.35 (1.0 H2O) | % C 62.20, % H 7.71, % N 10.36 (1.0 H2O) |
| HS | *** | ** | ** | ** | | |
| HT | * | | | | % C 53.20, % H 5.46, % N 9.04 (0.5 H2O) | % C 53.10, % H 5.57, % N 9.26 (0.5 H2O) |
| HU | *** | ** | * | * | % C 61.12, % H 7.55, % N 9.72 (1.0 H2O, 0.4 HCOOH) | % C 61.44, % H 7.78, % N 9.60 (1.0 H2O, 0.4 HCOOH) |
| HV | ** | | | | % C 62.87, % H 7.57, % N 9.84 (1.0 H2O) | % C 62.99, % H 7.93, % N 10.02 (1.0 H2O) |
| HW | *** | | | | | |
| HX | ** | | | | % C 60.53, % H 7.08, % N 10.73 (1.0 H2O, 0.2 HCOOH) | % C 60.55, % H 7.40, % N 10.49 (1.0 H2O, 0.2 HCOOH) |
| HY | *** | | * | * | % C 60.86, % H 8.00, % N 9.06 (1.4 H2O, 0.5 HCOOH) | % C 60.72, % H 7.96, % N 9.3 (1.4 H2O, 0.5 HCOOH) |
| HZ | ** | | | | % C 63.71, % H 8.02, % N 9.61 (0.7 H2O, 0.2 HCOOH) | % C 63.62, % H 7.86, % N 9.64 (0.7 H2O, 0.2 HCOOH) |
| IA | *** | | | | | |
| IB | ** | | | | % C 57.24, % H 6.12, % N 7.50 (0.8 H2O, 0.7 HCOOH) | % C 57.1, % H 6.13, % N 7.49 (0.8 H2O, 0.7 HCOOH) |
| IC | *** | | | | % C 48.61, % H 6.03, % N 10.95 (1.6 H2O, 1.7 HCOOH) | % C 48.5, % H 5.79, % N 10.94 (1.6 H2O, 1.7 HCOOH) |
| ID | * | | | | % C 53.58, % H 6.10, % N 12.95 does not match | % C 53.80, % H 7.28, % N 7.00 |
| IE | *** | | | | % C 60.89, % H 6.64, % N 8.10 (1.3 H2O, 1.3 HCOOH) | % C 60.80, % H 6.13, % N 8.11 (1.3 H2O, 1.3 HCOOH) |
| IF | * | | | | | |
| IG | ** | | | | % C 47.69, % H 4.80, % N 7.58 (0.7 H2O, 1.0 HCOOH) | % C 47.42, % H 4.40, % N 7.75 (0.7 H2O, 1.0 HCOOH) |
| IH | ** | | | | % C 48.76, % H 4.77, % N 7.90 (0.5 H2O, 0.6 HCOOH) | % C 48.73, % H 4.58, % N 8.06 (0.5 H2O, 0.6 HCOOH) |
| II | *** | *** | | | % C 52.81, % H 6.31, % N 9.01 (1.1 H2O, 1.5 HCOOH) | % C 52.40, % H 5.95, % N 9.61 (1.1 H2O, 1.5 HCOOH) |

TABLE 2-continued

| | | | | |
|---|---|---|---|---|
| IJ | ** | | % C 56.43, % H 6.73, % N 10.39 (does not match) | % C 56.45, % H 7.32, % N 6.20 |
| IK | * | | insufficient sample available | |
| IL | *** | *** | % C 58.59, % H 6.02, % N 7.52 (0.2 HCl) | % C 58.47, % H 6.05, % N 7.58 (0.2 HCl) |
| IM | ** | | insufficient material available | |
| IN | *** | *** | % C 60.11, % H 7.02, % N 10.73 (1.0 H2O) | % C 60.46, % H 7.21, % N 11.13 (1.0 H2O) |
| IO | *** | | | |
| IP | ** | | | |
| IQ | *** | | | |
| IR | ** | | % C 66.35, % H 6.77, % N 8.63 (1.1 H2O) | % C 66.53, % H 7.13, % N 8.95 (1.1 H2O) |
| IS | *** | | % C 53.82, % H 5.96, % N 7.23 (0.7 H2O, 1.5 NaCl) does not match | % C 53.55, % H 5.69, % N 7.81 (0.7 H2O, 1.5 NaCl) |
| IT | ** | | % C 59.53, % H 6.14, % N 8.33 (1.3 H2O, 1.0 NaCl) | % C 59.57, % H 6.37, % N 8.68 (1.3 H2O, 1.0 NaCl) |
| IU | *** | | % C 54.07, % H 5.87, % N 9.79 (1.4 H2O) | % C 54.25, % H 6.18, % N 9.99 (1.4 H2O) |
| IV | ** | | % C 55.77, % H 5.67, % N 10.16 (0.7 H2O) | % C 55.93, % H 6.03, % N 10.30 (0.7 H2O) |
| IW | ** | | % C 54.96, % H 5.74, % N 9.92 (1.0 H2O) | % C 55.20, % H 6.10, % N 10.16 (1.0 H2O) |
| IX | *** | *** | % C 50.02, % H 5.24, % N 9.00 (1.0 H2O, 0.3 HCOOH) | % C 50.38, % H 5.61, % N 9.13 (1.0 H2O, 0.3 HCOOH) |
| IY | *** | | % C 50.74, % H 5.37, % N 9.06 | % C 51.13, % H 5.65, % N 9.41 |
| IZ | *** | *** | % C 52.25, % H 5.76, % N 8.83 (0.9 H2O, 0.7 HCOOH) | % C 52.37, % H 5.56, % N 8.78 (0.9 H2O, 0.7 HCOOH) |
| JA | ** | | % C 54.44, % H 5.74, % N 9.43 (0.5 H2O, 0.2 HCOOH) | % C 54.09, % H 5.63, % N 9.42 (0.5 H2O, 0.2 HCOOH) |
| JB | *** | *** | % C 45.33, % H 5.62, % N 7.55 (2.0 H2O, 2.0 HCOOH) | % C 45.15, % H 5.14, % N 7.68 (2.0 H2O, 2.0 HCOOH) |
| JD | ** | | % C 48.44, % H 5.57, % N 8.47 (close match) | % C 48.91, % H 6.07, % N 7.15 (close match) |

TABLE 2-continued

| | | | | |
|---|---|---|---|---|
| JE | *** | *** | % C 53.58, % H 6.15, % N 9.39 (1.0 H2O, 1.0 HCOOH) | % C 53.96, % H 6.25, % N 8.99 (1.0 H2O, 1.0 HCOOH) |
| JF | ** | | % C 54.31, % H 6.11, % N 9.59 (1.0 H2O, 0.8 HCOOH) | % C 54.52, % H 6.29, % N 9.17 (1.0 H2O, 0.8 HCOOH) |
| JG | *** | | % C 56.34, % H 8.11, % N 10.79 (1.5 H2O, 0.4 HCOOH) | % C 56.71, % H 8.54, % N 10.23 (1.5 H2O, 0.4 HCOOH) |
| JH | * | | % C 58.64, % H 8.45, % N 11.25 (1.2 H2O) | % C 58.95, % H 8.70, % N 10.86 (1.2 H2O) |
| JI | *** | *** | % C 55.53, % H 8.05, % N 9.83 (1.7 H2O, 0.8 HCOOH) | % C 55.90, % H 8.57, % N 9.40 (1.7 H2O, 0.8 HCOOH) |
| JJ | ** | | % C 62.56, % H 8.83, % N 11.00 (0.2 H2O) | % C 62.70, % H 8.79, % N 10.97 (0.2 H2O) |
| JK | *** | *** | % C 60.39, % H 7.25, % N 11.20 (0.5 H2O, 0.5 HCOOH, 0.2 NH3) | % C 60.22, % H 7.30, % N 10.96 (0.5 H2O, 0.5 HCOOH, 0.2 NH3) |
| JL | * | | % C 61.61, % H 7.33, % N 10.98 (0.8 H2O) | % C 61.93, % H 7.43, % N 10.83 (0.8 H2O) |
| JM | *** | | % C 56.66, % H 8.59, % N 11.45 (0.6 H2O, 0.5 HCOOH, 0.2 NH3) | % C 56.87, % H 8.72, % N 11.47 (0.6 H2O, 0.5 HCOOH, 0.2 NH3) |
| JN | * | | | |
| JO | *** | *** | | |
| JP | *** | *** | | |
| JQ | *** | *** | | |
| JR | ** | | | |
| JZ | *** | | | |
| KA | * | | | |
| KB | ** | | | |
| KC | * | | | |

The $K_i$'s for the very good ACE-2 inhibiting compounds are given in Table 3.

TABLE 3

| ACE-2 Activity | Compound ID |
|---|---|
| $K_i$ of less than 0.1 μM | GI, GK, GL, GM, GN, GW, HA, HC, HE, HG, HK, HO, HQ, HS, HU, HY, IC, II, IO, IU, IY, IZ, JB, JE, JI, JK, JO, JP, JQ, |
| $K_i$ of between 0.5 μm and 0.1 μM | DX, EN, HF, HI, HW, IL, IQ, IN |

EXAMPLE 10

Transgenic ACE-2 Mice

Transgenic mice overexpressing human ACE-2 in the heart were produced using a 5.5 kB alpha-myosin heavy chain promoter driving the full length human ACE-2 cDNA. Two transgenic lines expressing protein (as determined by western blot analysis) were chosen for further evaluation. For line a3312: 69% (11/16) of the females and 38% of males (3/8) died at 4–6 weeks of age. For line a3320:8% (1/13) of the females and 17% (4/23) of the males have died at 13–22 weeks of age. Pathological analysis of the hearts of these mice indicates that the myofibrillar organization is disrupted. Vacuolization is frequently observed and hemorrhage is occasionally seen in these hearts.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

This application is related to U.S. patent application Ser. No. 09/163,648 entitled "Angiotensin Converting Enzyme Homolog and Therapeutic and Diagnostic Uses Therefor," filed on Sep. 30, 1998; and to U.S. Pat. No. 6,194,556, entitled "Angiotensin Converting Enzyme Homolog and Therapeutic and Diagnostic Uses Therefor" filed on Dec. 11, 1997, and issued on Feb. 27, 2001; the entire contents of each of which are hereby expressly incorporated herein by reference.

All patents, patent applications, and literature references cited herein are hereby expressly incorporated by reference.

6. The ACE-2 inhibiting compound of claim 1, wherein G is $C_1$–$C_3$ alkyl.

7. The ACE-2 inhibiting compound of claim 1, wherein G is an amine.

8. The ACE-2 inhibiting compound of claim 1, wherein M is imidazolyl, thienyl, triazolyl, pyrazolyl or thiazolyl.

What is claimed is:

1. An ACE-2 inhibiting compound, wherein said compound is of the formula:

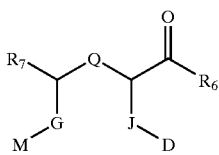

wherein

Q is $CH_2$, O, NH, or $NR^3$, wherein $R^3$ is substituted or unsubstituted $C_1$–$C_5$ branched or straight chain alkyl, $C_2$–$C_5$ branched or straight chain alkenyl, substituted or unsubstituted acyl, aryl, or a $C_3$–$C_8$ ring;

$R_6$ is hydroxyl or a protecting prodrug moiety;

$R_7$ is a hydrogen atom, carboxylic acid, ether, alkoxy, an amide, a protecting prodrug moiety, hydroxyl, thiol, heterocyclic, alkyl, or an amine;

G is a covalent bond, $C_1$–$C_5$ alkyl, alkenyl, alkynyl, ether, thioether, amine, or carbonyl;

M is heteroaryl, wherein M is substituted with at least one subanchor moiety, linked to M through a sublinking moiety, wherein said subanchor moiety is substituted or unsubstituted phenyl;

J is selected from the group consisting of a bond, a substituted or unsubstituted alkyl, alkenyl, or alkynyl moiety; and D is alkyl, alkenyl, alkynyl, aryl, or heteroaryl, optionally linked to G or M to form a ring, and pharmaceutically acceptable salts thereof.

2. The compound of claim 1, wherein Q is NH.

3. The ACE-2 inhibiting compound of claim 1, wherein $R_6$ is hydroxyl.

4. The ACE-2 inhibiting compound of claim 1, wherein $R_7$ is a carboxylic acid.

5. The ACE-2 inhibiting compound of claim 1, wherein G is a covalent bond.

9. The ACE-2 inhibiting compound of claim 1, wherein said sublinking moiety $(CH_2)_n$ or $(CH_2)_nO(CH_2)_n$, wherein n is 0, 1, 2 or 3.

10. The ACE-2 inhibiting compound of claim 1, wherein said subanchor moiety is substituted with at least one halogen, $CF_3$, cyano, alkoxy, nitro, ether, thiol, hydroxyl, alkyl, alkenyl, alkynyl, or aldehyde moiety.

11. An ACE-2 inhibiting compound, wherein said compound is of the formula:

wherein

Q is $CH_2$, O, NH, or $NR^3$, wherein $R^3$ is substituted or unsubstituted $C_1$–$C_5$ branched or straight chain alkyl, $C_2$–$C_5$ branched or straight chain alkenyl, substituted or unsubstituted acyl, aryl, or a $C_3$–$C_8$ ring;

$R_6$ is hydroxyl or a protecting prodrug moiety;

$R_7$ is a hydrogen atom, carboxylic acid, an amide, a protecting prodrug moiety, hydroxyl, thiol, heterocyclic, alkyl, or an amine;

G is a covalent bond, $C_1$–$C_5$ alkyl, alkenyl, alkynyl, ether, thioether, amine, or carbonyl;

M is heteroaryl, and is substituted with at least one subanchor moiety, linked to M through a sublinking moiety, wherein said sublinking moiety is $CH_2$ and said subanchor moiety is selected from the group consisting of 4-chlorophenyl, biphenyl, 3-chlorophenyl, 3,5-dichlorophenyl, 3-methylphenyl, 3,5-dimethylphenyl, 3-$CF_3$-phenyl, 2,5-dichlorophenyl, m-fluorophenyl, m-iodophenyl, methylenedioxyphenyl, m-trifluoromethylphenyl, 2,3-dichlorophenyl, 2,3-difluorophenyl, 2,3-dimethoxyphenyl, p-fluorophenyl, p-nitrophenyl, p-t-butylphenyl, p-isopropyl phenyl, p-trifluoromethoxyphenyl, 3,4-dimethylphenyl, 3,4-chlorophenyl, 4-methylphenyl, 4-cyanophenyl, cycloalkyl, or 4-trifluoromethylphenyl;

J is selected from the group consisting of a bond, a substituted or unsubstituted alkyl, alkenyl, or alkynyl moiety; and D is alkyl, alkenyl, alkynyl, aryl, or heteroaryl, optionally linked to G or M to form a ring, and pharmaceutically acceptable salts thereof.

12. The ACE-2 inhibiting compound of claim 1, wherein J is substituted or unsubstituted alkyl.

13. The ACE-2 inhibiting compound of claim 1, wherein J is alkynyl.

14. The ACE-2 inhibiting compound of claim 1, wherein J is a bond and D is alkyl, aryl or heteroaryl.

15. The ACE-2 inhibiting compound of claim 14, wherein D is methyl, ethyl, isopropyl, n-propyl, t-butyl, n-butyl, i-butyl, or pentyl.

16. The ACE-2 inhibiting compound of claim 1, wherein D is heteroaryl.

17. The ACE-2 inhibiting compound of claim 1, wherein D is pyridinyl or imidazolyl.

18. The ACE-2 inhibiting compound of claim 1, wherein D is substituted or unsubstituted phenyl.

19. The ACE-2 inhibiting compound of claim 1, wherein D is cycloalkyl.

20. A pharmaceutical composition comprising a pharmaceutically acceptable carrier and an effective amount of a compound of claim 1.

21. The pharmaceutical composition of claim 20, wherein said ACE-2 inhibiting compound is '2-{1-Carboxy-2-[3-(2,5-dichloro-benzyl)-3H-imidazol-4-yl]-ethylamino}-4-methyl-pentanoic acid, and pharmaceutically acceptable salts thereof.

22. A compound of the formula:

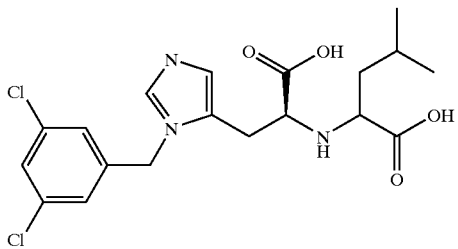

and pharmaceutically acceptable salts thereof.

23. The ACE-2 inhibiting compound of claim 11, wherein M is imidazolyl, thienyl, triazolyl, pyrazolyl or thiazolyl.

24. The ACE-2 inhibiting compound of claim 11, wherein J is substituted or unsubstituted alkyl.

25. The ACE-2 inhibiting compound of claim 11, wherein J is alkynyl.

26. The ACE-2 inhibiting compound of claim 11, wherein J is a bond and D is alkyl, aryl or heteroaryl.

27. The ACE-2 inhibiting compound of claim 26, wherein D is methyl, ethyl, isopropyl, n-propyl, t-butyl, n-butyl, i-butyl, or pentyl.

28. The ACE-2 inhibiting compound of claim 11, wherein D is heteroaryl.

29. The ACE-2 inhibiting compound of claim 11, wherein D is pyridinyl or imidazolyl.

30. The ACE-2 inhibiting compound of claim 11, wherein D is substituted or unsubstituted phenyl.

31. The ACE-2 inhibiting compound of claim 11, wherein D is cycloalkyl.

32. The ACE-2 inhibiting compound of claim 1, wherein said compound is:

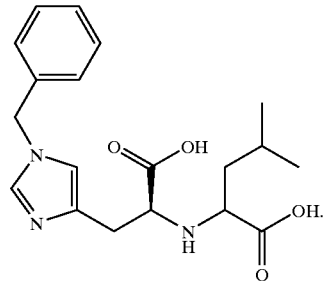

33. The ACE-2 inhibiting compound of claim 1, wherein said compound is:

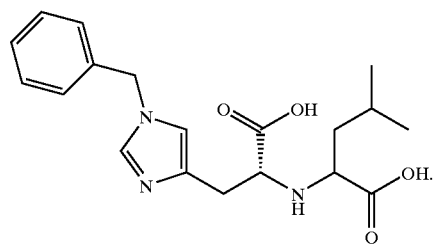

34. The ACE-2 inhibiting compound of claim 1, wherein said compound is:

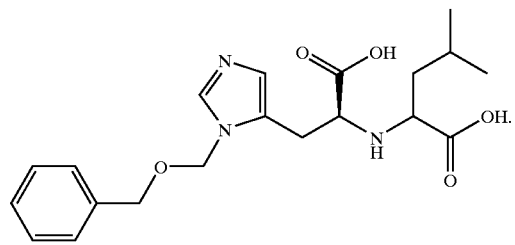

35. The ACE-2 inhibiting compound of claim 1, wherein said compound is:

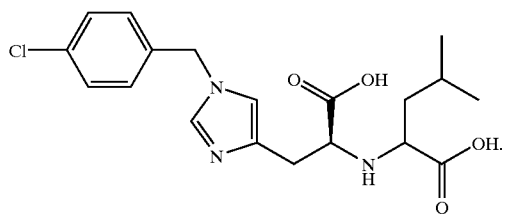

36. The ACE-2 inhibiting compound of claim 1, wherein said compound is:

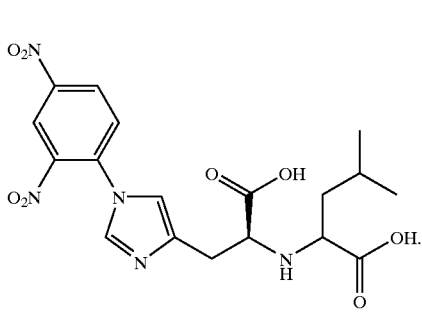

37. The ACE-2 inhibiting compound of claim 1, wherein said compound is:

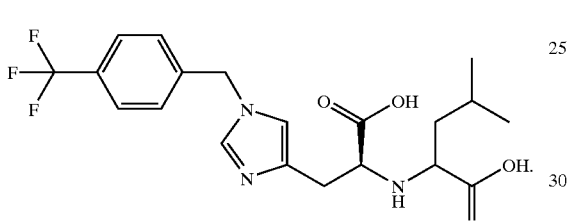

38. The ACE-2 inhibiting compound of claim 1, wherein said compound is:

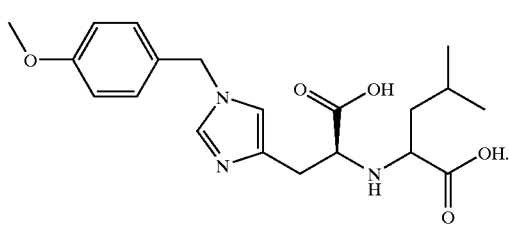

39. The ACE-2 inhibiting compound of claim 1, wherein said compound is:

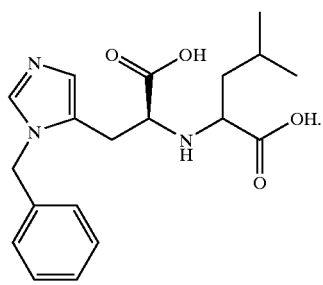

40. The ACE-2 inhibiting compound of claim 1, wherein said compound is:

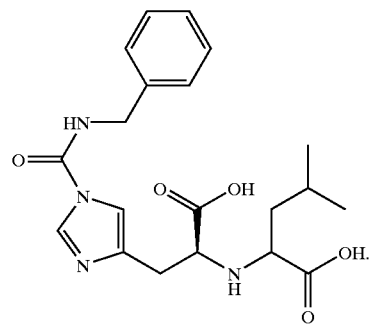

41. The ACE-2 inhibiting compound of claim 1, wherein said compound is:

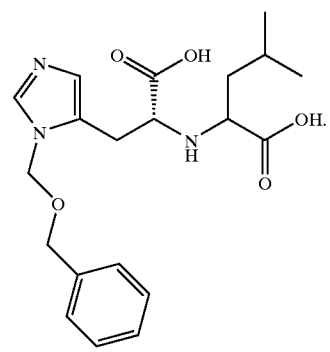

42. The ACE-2 inhibiting compound of claim 1, wherein said compound is:

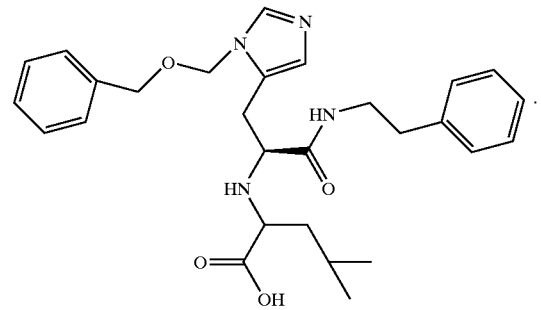

43. The ACE-2 inhibiting compound of claim 1, wherein said compound is:

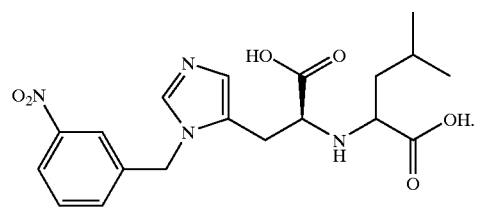

44. The ACE-2 inhibiting compound of claim 1, wherein said compound is:

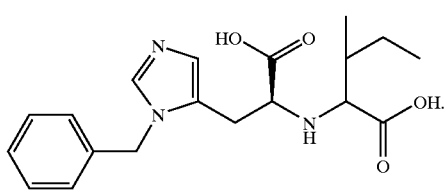

45. The ACE-2 inhibiting compound of claim 1, wherein said compound is:

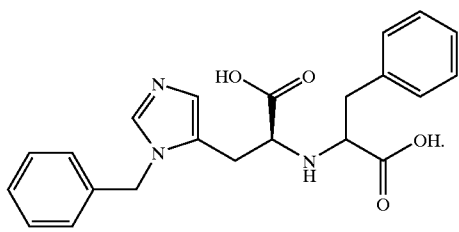

46. The ACE-2 inhibiting compound of claim 1, wherein said compound is:

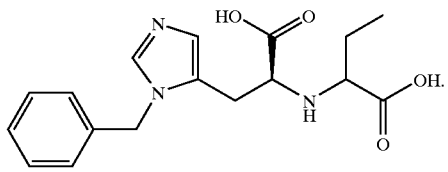

47. The ACE-2 inhibiting compound of claim 1, wherein said compound is:

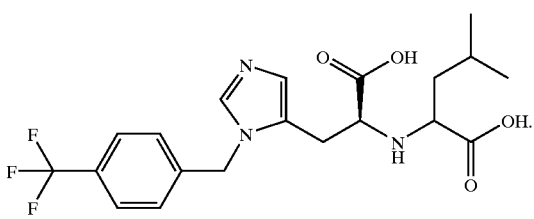

48. The ACE-2 inhibiting compound of claim 1, wherein said compound is:

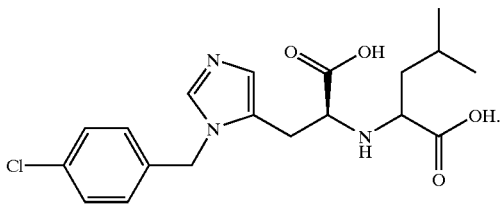

49. The ACE-2 inhibiting compound of claim 1, wherein said compound is:

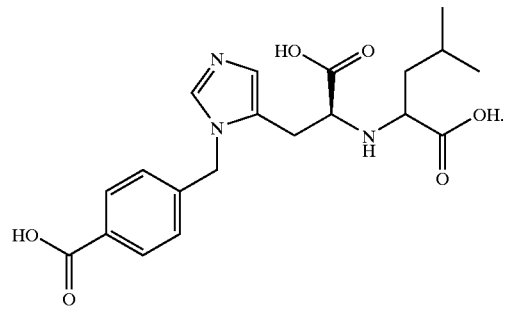

50. The ACE-2 inhibiting compound of claim 1, wherein said compound is:

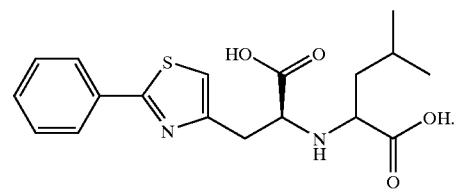

51. The ACE-2 inhibiting compound of claim 1, wherein said compound is:

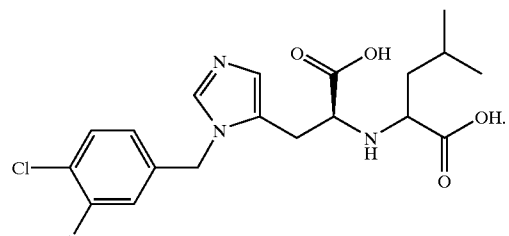

52. The ACE-2 inhibiting compound of claim 1, wherein said compound is:

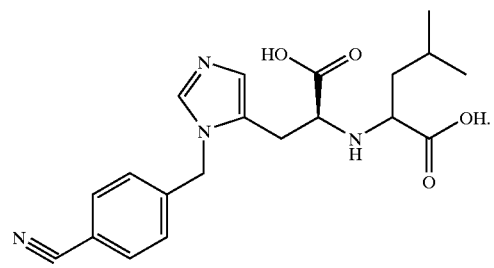

53. The ACE-2 inhibiting compound of claim 1, wherein said compound is:

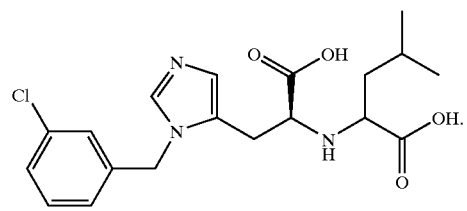

54. The ACE-2 inhibiting compound of claim 1, wherein said compound is:

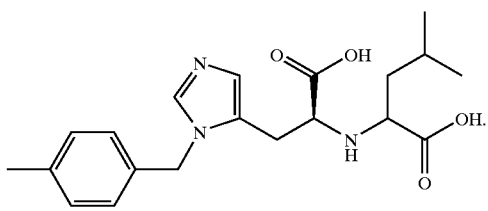

55. The ACE-2 inhibiting compound of claim 1, wherein said compound is:

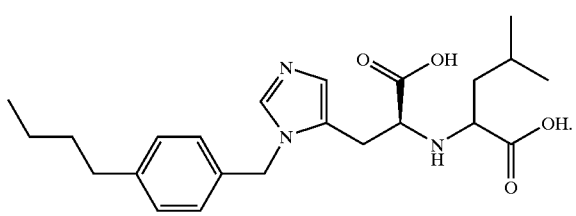

56. The ACE-2 inhibiting compound of claim 1, wherein said compound is:

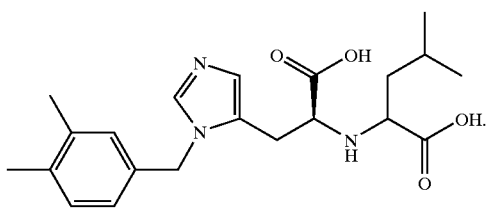

57. The ACE-2 inhibiting compound of claim 1, wherein said compound is:

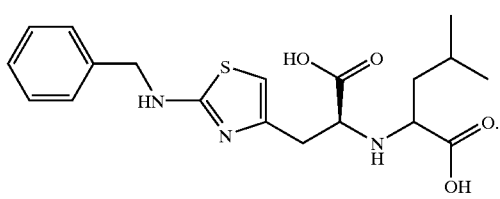

58. The ACE-2 inhibiting compound of claim 1, wherein said compound is:

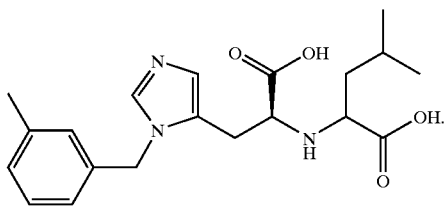

59. The ACE-2 inhibiting compound of claim 1, wherein said compound is:

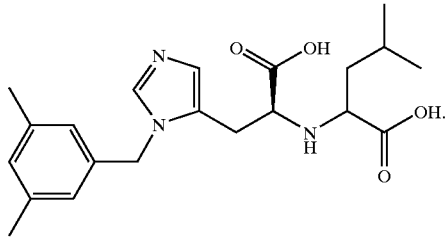

60. The ACE-2 inhibiting compound of claim 1, wherein said compound is:

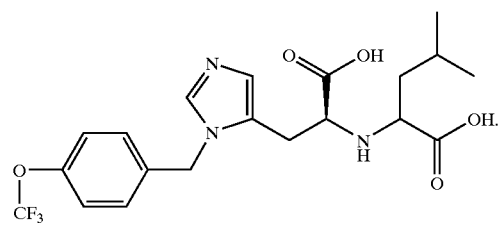

61. The ACE-2 inhibiting compound of claim 1, wherein said compound is:

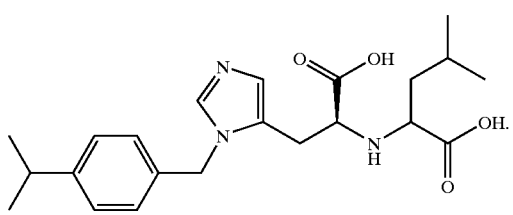

62. The ACE-2 inhibiting compound of claim 1, wherein said compound is:

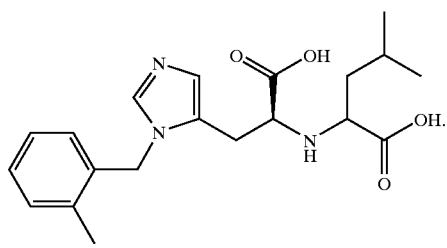

63. The ACE-2 inhibiting compound of claim 1, wherein said compound is:

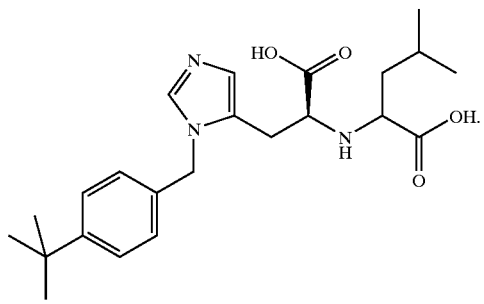

64. The ACE-2 inhibiting compound of claim 1, wherein said compound is:

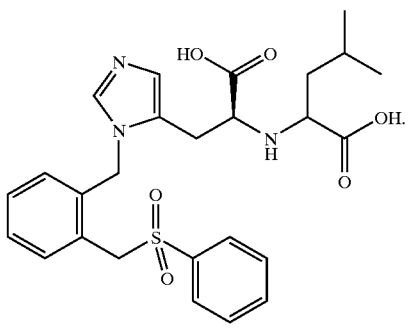

65. The ACE-2 inhibiting compound of claim 1, wherein said compound is:

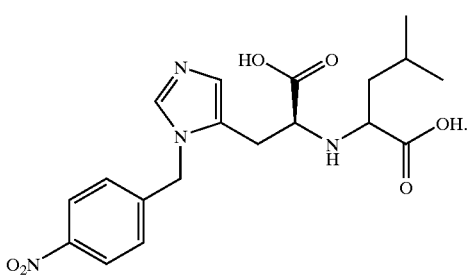

66. The ACE-2 inhibiting compound of claim 1, wherein said compound is:

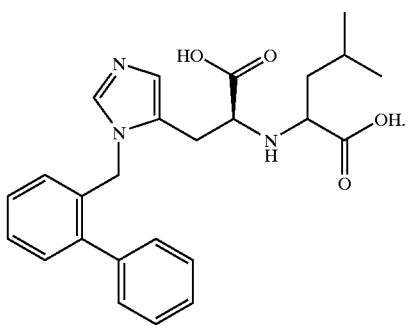

67. The ACE-2 inhibiting compound of claim 1, wherein said compound is:

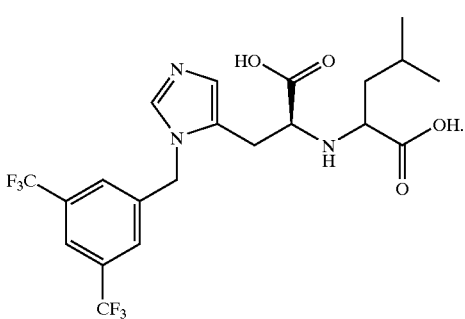

68. The ACE-2 inhibiting compound of claim 1, wherein said compound is:

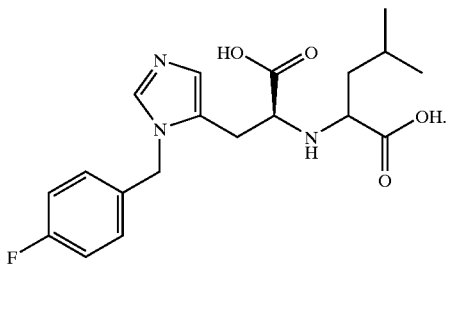

69. The ACE-2 inhibiting compound of claim 1, wherein said compound is:

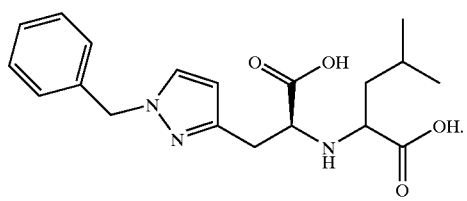

70. The ACE-2 inhibiting compound of claim 1, wherein said compound is:

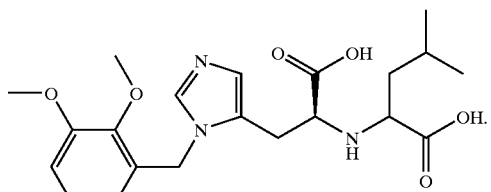

71. The ACE-2 inhibiting compound of claim 1, wherein said compound is:

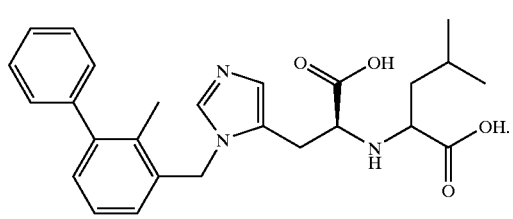

72. The ACE-2 inhibiting compound of claim 1, wherein said compound is:

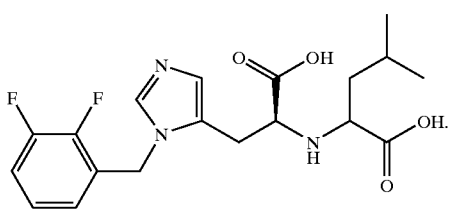

73. The ACE-2 inhibiting compound of claim 1, wherein said compound is:

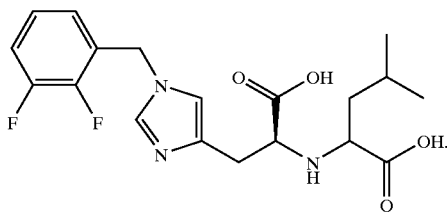

74. The ACE-2 inhibiting compound of claim 1, wherein said compound is:

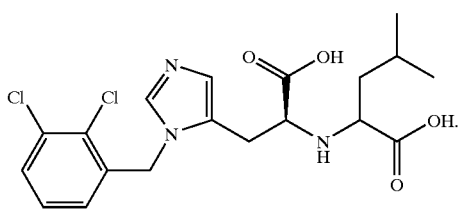

75. The ACE-2 inhibiting compound of claim 1, wherein said compound is:

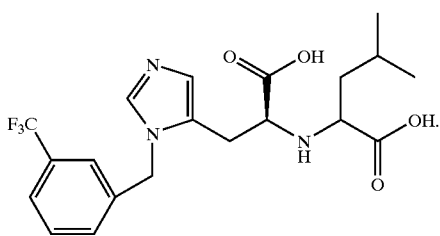

76. The ACE-2 inhibiting compound of claim 1, wherein said compound is:

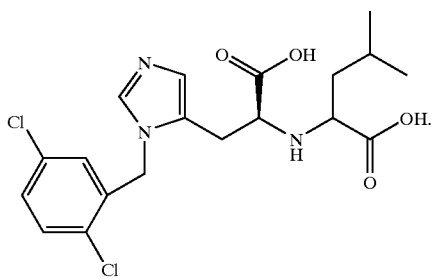

77. The ACE-2 inhibiting compound of claim 1, wherein said compound is:

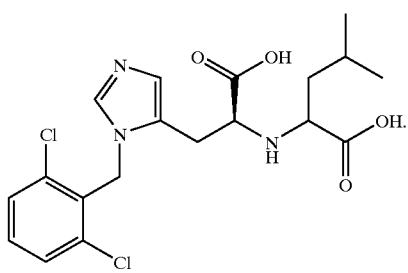

78. The ACE-2 inhibiting compound of claim 1, wherein said compound is:

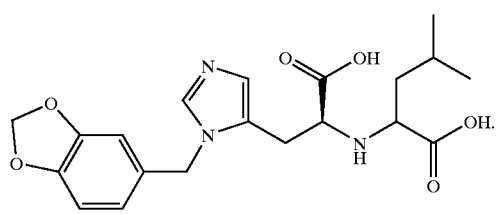

79. The ACE-2 inhibiting compound of claim 1, wherein said compound is:

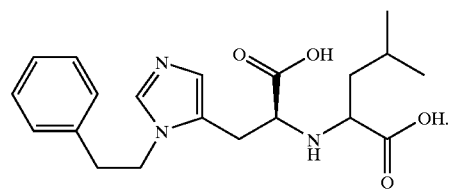

80. The ACE-2 inhibiting compound of claim 1, wherein said compound is:

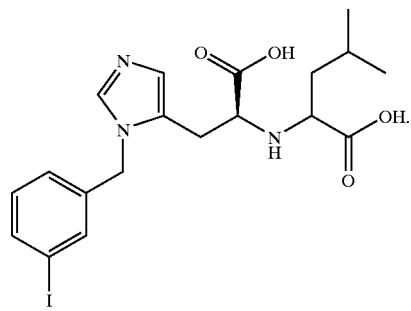

81. The ACE-2 inhibiting compound of claim 1, wherein said compound is:

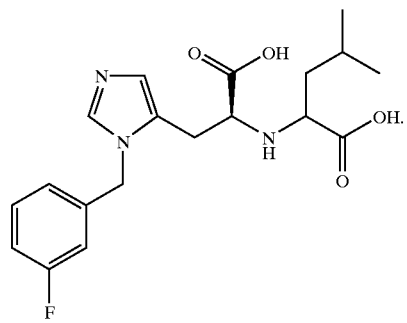

82. The ACE-2 inhibiting compound of claim 1, wherein said compound is:

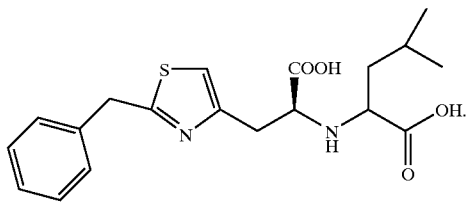

83. The ACE-2 inhibiting compound of claim 1, wherein said compound is:

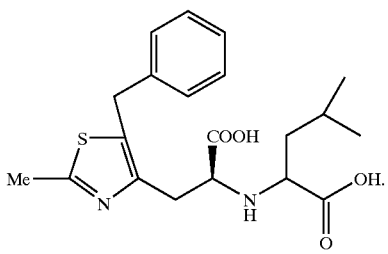

84. The ACE-2 inhibiting compound of claim 1, wherein said compound is:

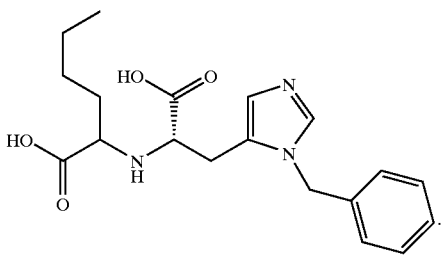

85. A pharmaceutical composition comprising a pharmaceutically acceptable carrier and an effective amount of a compound of claim 11.

86. The pharmaceutical composition of claim 20 or 85, wherein said effective amount of the ACE-2 inhibiting compound is an effective amount to treat a blood pressure related disease or disorder, cell proliferation disorder, kidney disorder, kinetensin associated disorder, inflammation associated disorder, or an allergic disorder.

87. The pharmaceutical composition of claim 20, wherein said ACE-2 inhibiting compound is '2-{1-Carboxy-2-[3-(2, 6-dichloro-benzyl)-3H-imidazol-4-yl]-ethylamino}-4-methyl-pentanoic acid, or pharmaceutically acceptable salts thereof.

88. The pharmaceutical composition of claim 20, wherein said ACE-2 inhibiting compound is 2-[2-(3-Benzo[1,3] dioxol-5-ylmethyl-3H-imidazol-4-yl)-1-carboxy-ethyl amino]-4-methyl-pentanoic acid, or pharmaceutically acceptable salts thereof.

89. The pharmaceutical composition of claim 20, wherein said ACE-2 inhibiting compound is 2-[1-Carboxy-2-(3-phenethyl-3H-imidazol-4-yl)-ethylamino]-4-methyl-pentanoic acid, or pharmaceutically acceptable salts thereof.

90. The pharmaceutical composition of claim 20, wherein said ACE-2 inhibiting compound is 2-{1-Carboxy-2-[3-(3-iodo-benzyl)-3H-imidazol-4-yl]-ethylamino}-4-methyl-pentanoic acid, or pharmaceutically acceptable salts thereof.

91. The pharmaceutical composition of claim 20, wherein said ACE-2 inhibiting compound is 2-{1-Carboxy-2-[3-(3-fluoro-benzyl)-3H-imidazol-4-yl]-ethylamino}-4-methyl-pentanoic acid, or pharmaceutically acceptable salts thereof.

92. The pharmaceutical composition of claim 20, wherein said ACE-2 inhibiting compound is 2-[2-(2-Benzyl-thiazol-4-yl)-1-carboxy-ethylamino]-4-methyl-pentanoic acid, or pharmaceutically acceptable salts thereof.

93. The pharmaceutical composition of claim 20, wherein said ACE-2 inhibiting compound is 2-[2-(5-Benzyl-2-methyl-thiazol-4-yl)-1-carboxy-ethylamino]-4-methyl-pentanoic acid, or pharmaceutically acceptable salts thereof.

94. The pharmaceutical composition of claim 20, wherein said ACE-2 inhibiting compound is 2-[2-(1-Benzyl-1H-imidazol-4-yl)-1-carboxy-ethylamino]-4-methyl-pentanoic acid, or pharmaceutically acceptable salts thereof.

95. The pharmaceutical composition of claim 20, wherein said ACE-2 inhibiting compound is 2-[2-(3-Benzyloxymethyl-3H-imidazol-4-yl)-1-carboxy-ethylamino]-4-methyl-pentanoic acid, or pharmaceutically acceptable salts thereof.

96. The pharmaceutical composition of claim 20, wherein said ACE-2 inhibiting compound is 2-{1-Carboxy-2-[1-(4-chloro-benzyl)-1H-imidazol-4-yl]-ethylamino]-4-methyl-pentanoic acid, or pharmaceutically acceptable salts thereof.

97. The pharmaceutical composition of claim 20, wherein said ACE-2 inhibiting compound is 2-(1-Carboxy-2-[1-(2, 4-dinitro-phenyl)-1H-imidazol-4-yl]-ethylamino}-4-methyl-pentanoic acid, or pharmaceutically acceptable salts thereof.

98. The pharmaceutical composition of claim 20, wherein said ACE-2 inhibiting compound is 2-{1-Carboxy-2-[1-(4-trifluoromethyl-benzyl)-1H-imidazol-4-yl]-ethylamino}-4-methyl-pentanoic acid, or pharmaceutically acceptable salts thereof.

99. The pharmaceutical composition of claim 20, wherein said ACE-2 inhibiting compound is 2-{1-Carboxy-2-[1-(4-methoxy-benzyl)-1H-imidazol-4-yl]-ethylamino}-4-methyl-pentanoic acid, or pharmaceutically acceptable salts thereof.

100. The pharmaceutical composition of claim 20, wherein said ACE-2 inhibiting compound is 2-[2-(3-Benzyloxymethyl-3H-imidazol-4-yl)-1-carboxy-ethylamino]-4-methyl-pentanoic acid, or pharmaceutically acceptable salts thereof.

101. The pharmaceutical composition of claim 20, wherein said ACE-2 inhibiting compound is 2-{1-Carboxy-2-[1-(4-chloro-benzyl)-1H-imidazol-4-yl]-ethylamino}-4-methyl-pentanoic acid, or pharmaceutically acceptable salts thereof.

102. The pharmaceutical composition of claim 20, wherein said ACE-2 inhibiting compound is 2-[2-(3-Benzyl-3H-imidazol-4-yl)-1-carboxy-ethylamino]-4-methyl-pentanoic acid, or pharmaceutically acceptable salts thereof.

103. The pharmaceutical composition of claim 20, wherein said ACE-2 inhibiting compound is 2-[2-(3-Benzyloxymethyl-3H-imidazol-4-yl)-1-carbamoyl-ethylamino]-4-methyl-pentanoic acid, or pharmaceutically acceptable salts thereof.

104. The pharmaceutical composition of claim 20, wherein said ACE-2 inhibiting compound is 2-[1-(Carboxymethyl-carbamoyl)-2-(1H-imidazol-4-yl)-ethylamino]-4-methyl-pentanoic acid, or pharmaceutically acceptable salts thereof.

105. The pharmaceutical composition of claim 20, wherein said ACE-2 inhibiting compound is 2-[2-(3-Benzyloxymethyl-3H-imidazol-4-yl)-1- phenethylcarbamoyl-ethylamino]-4-methyl-pentanoic acid, or pharmaceutically acceptable salts thereof.

106. The pharmaceutical composition of claim 20, wherein said ACE-2 inhibiting compound is 2-[2-(3-Benzyl-3H-imidazol-4-yl)-1-carboxy-ethylamino]-hexanoic acid, or pharmaceutically acceptable salts thereof.

107. The pharmaceutical composition of claim 20, wherein said ACE-2 inhibiting compound is 2-{1-Carboxy-2-[3-(3-nitro-benzyl)-3H-imidazol-4-yl]-ethylamino}-4-methyl-pentanoic acid, or pharmaceutically acceptable salts thereof.

108. The pharmaceutical composition of claim 20, wherein said ACE-2 inhibiting compound is 2-[2-(3-Benzyl-3H-imidazol-4-yl)-1-carboxy-ethylamino]-3-methyl-pentanoic acid, or pharmaceutically acceptable salts thereof.

109. The pharmaceutical composition of claim 20, wherein said ACE-2 inhibiting compound is 3-(3-Benzyl-3H-imidazol-4-yl)-2-(1-carboxy-2-phenyl-ethylamino)-propionic acid, or pharmaceutically acceptable salts thereof.

110. The pharmaceutical composition of claim 20, wherein said ACE-2 inhibiting compound is 2-[2-(3-Benzyl-3H-imidazol-4-yl)-1-carboxy-ethylamino]-butyric acid, or pharmaceutically acceptable salts thereof.

111. The pharmaceutical composition of claim 20, wherein said ACE-2 inhibiting compound is 2-{1-Carboxy-2-[3-(4-trifluoromethyl-benzyl)-3H-imidazol-4-yl]-ethylamino}-4-methyl-pentanoic acid, or pharmaceutically acceptable salts thereof.

112. The pharmaceutical composition of claim 20, wherein said ACE-2 inhibiting compound is 2-(1-Carboxy-2-[3-(4-chloro-benzyl)-3H-imidazol-4-yl]-ethylamino}-4-methyl-pentanoic acid, or pharmaceutically acceptable salts thereof.

113. The pharmaceutical composition of claim 20, wherein said ACE-2 inhibiting compound is 4-{5-[2-Carboxy-2-(1-carboxy-3-methyl-butylamino)-ethyl]-imidazol-1-ylmethyl}-benzoic acid, or pharmaceutically acceptable salts thereof.

114. The pharmaceutical composition of claim 20, wherein said ACE-2 inhibiting compound is 2-[1-Carboxy-2-(2-phenyl-thiazol-4-yl)-ethylamino]-4-methyl-pentanoic acid, or pharmaceutically acceptable salts thereof.

115. The pharmaceutical composition of claim 20, wherein said ACE-2 inhibiting compound is 2-{1-Carboxy-2-[3-(3,4-dichloro-benzyl)-3H-imidazol-4-yl]-ethylamino}-4-methyl-pentanoic acid, or pharmaceutically acceptable salts thereof.

116. The pharmaceutical composition of claim 20, wherein said ACE-2 inhibiting compound is 2-{1-Carboxy-2-[3-(4-cyano-benzyl)-3H-imidazol-4-yl]-ethylamino}-4-methyl-pentanoic acid, or pharmaceutically acceptable salts thereof.

117. The pharmaceutical composition of claim 20, wherein said ACE-2 inhibiting compound is '2-{1-Carboxy-2-[3-(3-chloro-benzyl)-3H-imidazol-4-yl]-ethylamino}-4-methyl-pentanoic acid, or pharmaceutically acceptable salts thereof.

118. The pharmaceutical composition of claim 20, wherein said ACE-2 inhibiting compound is '2-{1-Carboxy-2-[3-(3,5-dichloro-benzyl)-3H-imidazol-4-yl]-ethylamino}-4-methyl-pentanoic acid, or pharmaceutically acceptable salts thereof.

119. The pharmaceutical composition of claim 20, wherein said ACE-2 inhibiting compound is '2-{1-Carboxy-2-[3-(4-methyl-benzyl)-3H-imidazol-4-yl]-ethylamino}-4-methyl-pentanoic acid, or pharmaceutically acceptable salts thereof.

120. The pharmaceutical composition of claim 20, wherein said ACE-2 inhibiting compound is '2-{2-[3-(4-Butyl-benzyl)-3H-imidazol-4-yl]-1-carboxy-ethylamino}-4-methyl-pentanoic acid, or pharmaceutically acceptable salts thereof.

121. The pharmaceutical composition of claim 20, wherein said ACE-2 inhibiting compound is '2-{1-Carboxy-2-[3-(3,4-dimethyl-benzyl)-3H-imidazol-4-yl]-ethylamino}-4-methyl-pentanoic acid, or pharmaceutically acceptable salts thereof.

122. The pharmaceutical composition of claim 20, wherein said ACE-2 inhibiting compound is '2-[2-(2-Benzylamino-thiazol-4-yl)-1-carboxy-ethylamino]-4-methyl-pentanoic acid, or pharmaceutically acceptable salts thereof.

123. The pharmaceutical composition of claim 20, wherein said ACE-2 inhibiting compound is '2-{1-Carboxy-2-[3-(3-methyl-benzyl)-3H-imidazol-4-yl]-ethylamino}-4-methyl-pentanoic acid, or pharmaceutically acceptable salts thereof.

124. The pharmaceutical composition of claim 20, wherein said ACE-2 inhibiting compound is '2-{1-Carboxy-2-[3-(3,5-dimethyl-benzyl)-3H-imidazol-4-yl]-ethylamino}-4-methyl-pentanoic acid, or pharmaceutically acceptable salts thereof.

125. The pharmaceutical composition of claim 20, wherein said ACE-2 inhibiting compound is '2-{1-Carboxy-2-[3-(4-trifluoromethoxy-benzyl)-3H-imidazol-4-yl]-ethylamino}-4-methyl-pentanoic acid, or pharmaceutically acceptable salts thereof.

126. The pharmaceutical composition of claim 20, wherein said ACE-2 inhibiting compound is '2-{1-Carboxy-2-[3-(4-isopropyl-benzyl)-3H-imidazol-4-yl]-ethylamino}-4-methyl-pentanoic acid, or pharmaceutically acceptable salts thereof.

127. The pharmaceutical composition of claim 20, wherein said ACE-2 inhibiting compound is '2-{1-Carboxy-2-[3-(2-methyl-benzyl)-3H-imidazol-4-yl]-ethylamino}-4-methyl-pentanoic acid, or pharmaceutically acceptable salts thereof.

128. The pharmaceutical composition of claim 20, wherein said ACE-2 inhibiting compound is '2-{2-[3-(4-tert-Butyl-benzyl)-3H-imidazol-4-yl]-1-carboxy-ethylamino}-4-methyl-pentanoic acid, or pharmaceutically acceptable salts thereof.

129. The pharmaceutical composition of claim 20, wherein said ACE-2 inhibiting compound is '2-{2-[3-(2-Benzenesulfonylmethyl-benzyl)-3H-imidazol-4-yl]-1-carboxy-ethylamino}-4-methyl-pentanoic acid, or pharmaceutically acceptable salts thereof.

130. The pharmaceutical composition of claim 20, wherein said ACE-2 inhibiting compound is '2-{1-Carboxy-2-[3-(4-nitro-benzyl)-3H-imidazol-4-yl]-ethylamino}-4-methyl-pentanoic acid, or pharmaceutically acceptable salts thereof.

131. The pharmaceutical composition of claim 20, wherein said ACE-2 inhibiting compound is '2-[2-(3-Biphenyl-2-ylmethyl-3H-imidazol-4-yl)-1-carboxy-ethylamino]-4-methyl-pentanoic acid, or pharmaceutically acceptable salts thereof.

132. The pharmaceutical composition of claim 20, wherein said ACE-2 inhibiting compound is '2-{2-[3-(3,5-Bis-trifluoromethyl-benzyl)-3H-imidazol-4-yl]-1-carboxy-ethylamino}-4-methyl-pentanoic acid, or pharmaceutically acceptable salts thereof.

133. The pharmaceutical composition of claim 20, wherein said ACE-2 inhibiting compound is '2-{1-Carboxy- 2-[3-(4-fluoro-benzyl)-3H-imidazol-4-yl]-ethylamino}-4-methyl-pentanoic acid, or pharmaceutically acceptable salts thereof.

134. The pharmaceutical composition of claim 20, wherein said ACE-2 inhibiting compound is '2-[1-Carboxy-2-(2-phenyl-thiazol-4-yl)-ethylamino]-4-methyl-pentanoic acid, or pharmaceutically acceptable salts thereof.

135. The pharmaceutical composition of claim 20, wherein said ACE-2 inhibiting compound is '2-[2-(1-Benzyl-1H-pyrazol-3-yl)-1-carboxy-ethylamino]-4-methyl-pentanoic acid, or pharmaceutically acceptable salts thereof.

136. The pharmaceutical composition of claim 20, wherein said ACE-2 inhibiting compound is '2-{1-Carboxy-2-[3-(2,3-dimethoxy-benzyl)-3H-imidazol-4-yl]-ethylamino}-4-methyl-pentanoic acid, or pharmaceutically acceptable salts thereof.

137. The pharmaceutical composition of claim 20, wherein said ACE-2 inhibiting compound is '2-{1-Carboxy-2-[3-(2-methyl-biphenyl-3-ylmethyl)-3H-imidazol-4-yl]-ethylamino}-4-methyl-pentanoic acid, or pharmaceutically acceptable salts thereof.

138. The pharmaceutical composition of claim 20, wherein said ACE-2 inhibiting compound is '2-{1-Carboxy-2-[3-(2,3-difluoro-benzyl)-3H-imidazol-4-yl]-ethylamino}-4-methyl-pentanoic acid, or pharmaceutically acceptable salts thereof.

139. The pharmaceutical composition of claim 20, wherein said ACE-2 inhibiting compound is '2-{1-Carboxy-2-[1-(2,3-difluoro-benzyl)-1H-imidazol-4-yl]-ethylamino}-4-methyl-pentanoic acid, or pharmaceutically acceptable salts thereof.

140. The pharmaceutical composition of claim 20, wherein said ACE-2 inhibiting compound is '2-{1-Carboxy-2-[3-(2,3-dichloro-benzyl)-3H-imidazol-4-yl]-ethylamino}-4-methyl-pentanoic acid, or pharmaceutically acceptable salts thereof.

141. The pharmaceutical composition of claim 20, wherein said ACE-2 inhibiting compound is '2-{1-Carboxy-2-[3-(3-trifluoromethyl-benzyl)-3H-imidazol-4-yl]-ethylamino}-4-methyl-pentanoic acid, or pharmaceutically acceptable salts thereof.

142. A compound that is:

2-{1-Carboxy-2-[3-(3-nitro-benzyl)-3H-imidazol-4-yl]-ethylamino}-4-methyl-pentanoic acid;

2-[2-(3-Benzyl-3H-imidazol-4-yl)-1-carboxy-ethylamino]-hexanoic acid;

2-[2-(3-Benzyl-3H-imidazol-4-yl)-1-carboxy-ethylamino]-4-methyl-pentanoic acid;

2-[2-(3-Benzyloxymethyl-3H-imidazol-4-yl)-1-carboxy-ethylamino]-4-methyl-pentanoic acid;

2-[2-(1-Benzyl-1H-imidazol-4-yl)-1-carboxy-ethylamino]-4-methyl-pentanoic acid;

2-{1-Carboxy-2-[1-(4-chloro-benzyl)-1H-imidazol-4-yl]-ethylamino}-4-methyl-pentanoic acid;

2-[2-(1-Benzyl-1H-imidazol-4-yl)-1-carboxy-ethylamino]-4-methyl-pentanoic acid;

2-{1-Carboxy-2-[1-(2,4-dinitro-phenyl)-1H-imidazol-4-yl]-ethylamino}-4-methyl-pentanoic acid;

2-[2-(1-Benzyl-1H-imidazol-4-yl)-1-carboxy-ethylamino]-4-methyl-pentanoic acid;

2-{1-Carboxy-2-[1-(4-methoxy-benzyl)-1H-imidazol-4-yl]-ethylamino}-4-methyl-pentanoic acid;

2-{1-Carboxy-2-[1-(4-trifluoromethyl-benzyl)-1H-imidazol-4-yl]-ethylamino}-4-methyl-pentanoic acid;

2-{1-Carboxy-2-[1-(4-methoxy-benzyl)-1H-imidazol-4-yl]-ethylamino}-4-methyl-pentanoic acid;

2-(1-Carboxy-2-[1-(4-trifluoromethyl-benzyl)-1H-imidazol-4-yl]-ethylamino}-4-methyl-pentanoic acid;

2-{1-Carboxy-2-[3-(4-trifluoromethyl-benzyl)-3H-imidazol-4-yl]-ethylamino}-4-methyl-pentanoic acid;

2-{1-Carboxy-2-[3-(4-chloro-benzyl)-3H-imidazol-4-yl]-ethylamino}-4-methyl-pentanoic acid;

2-[1-Carboxy-2-(2-phenyl-thiazol-4-yl)-ethylamino]-4-methyl-pentanoic acid;

2-[2-(1-Benzyl-1H-benzoimidazol-2-yl)-1-carboxy-ethylamino]-4-methyl-pentanoic acid;

2-{1-Carboxy-2-[3-(3,4-dichloro-benzyl)-3H-imidazol-4-yl]-ethylamino}-4-methyl-pentanoic acid;

2-{1-Carboxy-2-[3-(4-cyano-benzyl)-3H-imidazol-4-yl]-ethylamino}-4-methyl-pentanoic acid;

2-{1-Carboxy-2-[3-(3-chloro-benzyl)-3H-imidazol-4-yl]-ethylamino}-4-methyl-pentanoic acid;

2-{1-Carboxy-2-[3-(3,5-dichloro-benzyl)-3H-imidazol-4-yl]-ethylamino}-4-methyl-pentanoic acid;

2-{1-Carboxy-2-[3-(4-methyl-benzyl)-3H-imidazol-4-yl]-ethylamino}-4-methyl-pentanoic acid;

2-{2-[3-(4-Butyl-benzyl)-3H-imidazol-4-yl]-1-carboxy-ethylamino}-4-methyl-pentanoic acid;

2-{1-Carboxy-2-[3-(3,4-dimethyl-benzyl)-3H-imidazol-4-yl]-ethylamino}-4-methyl-pentanoic acid;

2-[2-(2-Benzylamino-thiazol-4-yl)-1-carboxy-ethylamino]-4-methyl-pentanoic acid;

2-{1-Carboxy-2-[3-(3-methyl-benzyl)-3H-imidazol-4-yl]-ethylamino}-4-methyl-pentanoic acid;

2-{1-Carboxy-2-[3-(3,5-dimethyl-benzyl)-3H-imidazol-4-yl]-ethylamino}-4-methyl-pentanoic acid;

2-{1-Carboxy-2-[3-(4-trifluoromethoxy-benzyl)-3H-imidazol-4-yl]-ethylamino}-4-methyl-pentanoic acid;

2-{1-Carboxy-2-[3-(4-isopropyl-benzyl)-3H-imidazol-4-yl]-ethylamino}-4-methyl-pentanoic acid;

2-{1-Carboxy-2-[3-(2-methyl-benzyl)-3H-imidazol-4-yl]-ethylamino}-4-methyl-pentanoic acid;

2-{2-[3-(4-tert-Butyl-benzyl)-3H-imidazol-4-yl]-1-carboxy-ethylamino}-4-methyl-pentanoic acid;

2-{2-[3-(2-Benzenesulfonylmethyl-benzyl)-3H-imidazol-4-yl]-1-carboxy-ethylamino}-4-methyl-pentanoic acid;

2-{1-Carboxy-2-[3-(4-nitro-benzyl)-3H-imidazol-4-yl]-ethylamino}-4-methyl-pentanoic acid;

2-[2-(3-Biphenyl-2-ylmethyl-3H-imidazol-4-yl)-1-carboxy-ethylamino]-4-methyl-pentanoic acid;

2-{2-[3-(3,5-Bis-trifluoromethyl-benzyl)-3H-imidazol-4-yl]-1-carboxy-ethylamino}-4-methyl-pentanoic acid;

2-{1-Carboxy-2-[3-(4-fluoro-benzyl)-3H-imidazol-4-yl]-ethylamino}-4-methyl-pentanoic acid;

2-[1-Carboxy-2-(2-phenyl-thiazol-4-yl)-ethylamino]-4-methyl-pentanoic acid;

2-[2-(1-Benzyl-1H-pyrazol-3-yl)-1-carboxy-ethylamino]-4-methyl-pentanoic acid;

2-{1-Carboxy-2-[3-(2,3-dimethoxy-benzyl)-3H-imidazol-4-yl]-ethylamino}-4-methyl-pentanoic acid;

2-{1-Carboxy-2-[3-(2-methyl-biphenyl-3-ylmethyl)-3H-imidazol-4-yl]-ethylamino}-4-methyl-pentanoic acid;

2-{1-Carboxy-2-[3-(2,3-difluoro-benzyl)-3H-imidazol-4-yl]-ethylamino}-4-methyl-pentanoic acid;

2-{1-Carboxy-2-[1-(2,3-difluoro-benzyl)-1H-imidazol-4-yl]-ethylamino}-4-methyl-pentanoic acid;

2-{1-Carboxy-2-[3-(2,3-dichloro-benzyl)-3H-imidazol-4-yl]-ethylamino}-4-methyl-pentanoic acid;

2-{1-Carboxy-2-[3-(3-trifluoromethyl-benzyl)-3H-imidazol-4-yl]-ethylamino}-4-methyl-pentanoic acid;

2-{1-Carboxy-2-[3-(2,5-dichloro-benzyl)-3H-imidazol-4-yl]-ethylamino}-4-methyl-pentanoic acid;

2-{1-Carboxy-2-[3-(2,6-dichloro-benzyl)-3H-imidazol-4-yl]-ethylamino}-4-methyl-pentanoic acid;

4-Methyl-2-[1-methylcarbamoyl-2-(3-phenylamino-3H-imidazol-4-yl)-ethylamino]-pentanoic acid;

2-[2-(4-Benzyl-furan-3-yl)-1-carboxy-ethylamino]-4-methyl-pentanoic acid;

2-[1-Carboxy-2-(3-phenyl-3H-imidazol-4-yl)-ethylamino]-4-methyl-pentanoic acid;

2-[1-Carboxy-2-(3-phenethyl-3H-imidazol-4-yl)-ethylamino]-4-methyl-pentanoic acid;

2-{1-Carboxy-2-[3-(pyridin-3-yloxy)-3H-imidazo}-4-yl]-ethylamino}-4-methyl-pentanoic acid;

2-{1-[3-(4-nitro-phenoxy)-3H-imidazol-4-yl]-ethylamino}-4-methyl-pentanoic acid;

2-[1-Carboxy-2-(3-phenoxy-3H-imidazol-4-yl)-ethylamino]-4-methyl-pentanoic acid;

2-{1-Carboxy-2-[3-(2-nitro-benzyl)-3H-imidazol-4-yl]-ethylamino}-4-methyl-pentanoic acid;

2-{1-Carboxy-2-[3-(3-nitro-benzyl)-3H-imidazol-4-yl]-ethylamino}-4-methyl-pentanoic acid;

2-{1-Carboxy-2-[3-(2-trifluoromethyl-benzyl)-3H-imidazol-4-yl]-ethylamino}-4-methyl-pentanoic acid;

2-{1-Carboxy-2-[3-(3-trifluoromethyl-benzyl)-3H-imidazol-4-yl]-ethylamino}-4-methyl-pentanoic acid;

2-{1-Carboxy-2-[3-(2-methyl-benzyl)-3H-imidazol-4-yl]-ethylamino}-4-methyl-pentanoic acid;

2-{1-Carboxy-2-[3-(3-methyl-benzyl)-3H-imidazol-4-yl]-ethylamino}-4-methyl-pentanoic acid;

2-{1-Carboxy-2-[3-(2-chloro-benzyl)-3H-imidazol-4-yl]-ethylamino}-4-methyl-pentanoic acid;

2-{1-Carboxy-2-[3-(3-chloro-benzyl)-3H-imidazol-4-yl]-ethylamino}-4-methyl-pentanoic acid;

2-{1-Carboxy-2-[3-(2-hydroxy-benzyl)-3H-imidazol-4-yl]-ethylamino}-4-methyl-pentanoic acid;

2-{1-Carboxy-2-[3-(3-hydroxy-benzyl)-3H-imidazol-4-yl]-ethylamino}-4-methyl-pentanoic acid;

2-{1-Carboxy-2-[3-(2-fluoro-benzyl)-3H-imidazol-4-yl]-ethylamino}-4-methyl-pentanoic acid;

2-[2-(3-Benzyl-3H-imidazol-4-yl)-1-carboxy-ethylamino]-4-methyl-pentanoic acid;

2-[1-Carboxy-2-(3-phenylamino-3H-imidazol-4-yl)-ethylamino]-4-methyl-pentanoic acid;

2-{[2,3-Dioxo-1-(3-phenylamino-3H-imidazol-4-ylmethyl)-butyl]-methyl-amino}-4-methyl-pentanoic acid;

2-{[2,3-Dioxo-1-(4-phenylamino-furan-3-ylmethyl)-butyl]-methyl-amino}-4-methyl-pentanoic acid;

2-[2,3-Dioxo-1-(4-phenylamino-furan-3-ylmethyl)-butylamino]-4-methyl-pentanoic acid;

2-[1-Carboxy-2-(4-phenylamino-furan-3-yl)-ethylamino]-4-methyl-pentanoic acid;

2-[1-Carboxy-2-(2-o-tolyl-2H-isoindol-1-yl)-ethylamino]-4-methyl-pentanoic acid;

2-[2-(2-Benzyl-2H-isoindol-1-yl)-1-carboxy-ethylamino]-4-methyl-pentanoic acid;

2-[1-Carboxy-2-(2-phenyl-2H-isoindol-1-yl)-ethylamino]-4-methyl-pentanoic acid;

2-{1-Carboxy-2-[2-(3-nitro-phenyl)-2H-isoindol-1-yl]-ethylamino}-4-methyl-pentanoic acid;

2-{1-Carboxy-2-[2-(4-nitro-phenyl)-2H-isoindol-1-yl]-ethylamino}-4-methyl-pentanoic acid;

2-{1-Carboxy-2-[2-(4-nitro-benzyl)-2H-isoindol-1-yl]-ethylamino}-4-methyl-pentanoic acid;

2-{-Carboxy-2-[3-(3-trifluoromethyl-benzyl)-3H-imidazol-4-yl]-ethylamino}-4-methyl-pentanoic acid;

2-{1-Carboxy-2-[3-(2,5-dichloro-benzyl)-3H-imidazol-4-yl]-ethylamino}-4-methyl-pentanoic acid;

2-{1-Carboxy-2-[3-(2,6-dichloro-benzyl)-3H-imidazol-4-yl]-ethylamino}-4-methyl-pentanoic acid;

2-[1-Carboxy-2-(3-phenethyl-3H-imidazol-4-yl)-ethylamino]-4-methyl-pentanoic acid;

2-{1-Carboxy-2-[3-(3-iodo-benzyl)-3H-imidazol-4-yl]-ethylamino}-4-methyl-pentanoic acid;

2-[1-Carboxy-2-[3-(3-fluoro-benzyl)-3H-imidazol-4-yl]-ethylamino]-4-methyl-pentanoic acid;

2-[1-Carboxy-2-(2-phenylethynyl-1H-imidazol-4-yl)-ethylamino]-4-methyl-pentanoic acid;

2-[1-Carboxy-2-(1-methyl-2-phenylethynyl-1H-imidazol-4-yl)-ethylamino]-4-methyl-pentanoic acid;

2-[1-Carboxy-2-(2-phenethyl-1H-imidazol-4-yl)-ethylamino]-4-methyl-pentanoic acid;

2-[1-Carboxy-3-(3-phenyl-3H-imidazol-4-yl)-propylamino]-4-methyl-pentanoic acid;

2-[1-Carboxy-2-(3-phenyl-3H-imidazol-4-yl)-ethylamino]-4-methyl-pentanoic acid;

2-[2-(3-Benzyl-2,5-dimethyl-3H-imidazol-4-yl)-1-carboxy-ethylamino]-4-methyl-pentanoic acid;

2-[1-Carboxy-4-(3-phenyl-3H-imidazol-4-yl)-butylamino]-4-methyl-pentanoic acid;

2-[2-(2-Benzyl-thiazol-4-yl)-1-carboxy-ethylamino]-4-methyl-pentanoic acid;

2-[2-(5-Benzyl-2-methyl-thiazol-4-yl)-1-carboxy-ethylamino]-4-methyl-pentanoic acid;

or pharmaceutically acceptable salts thereof.

143. A compound that is:

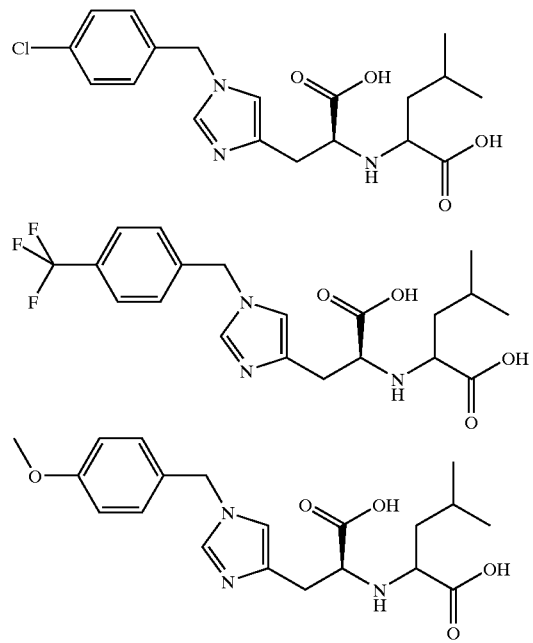

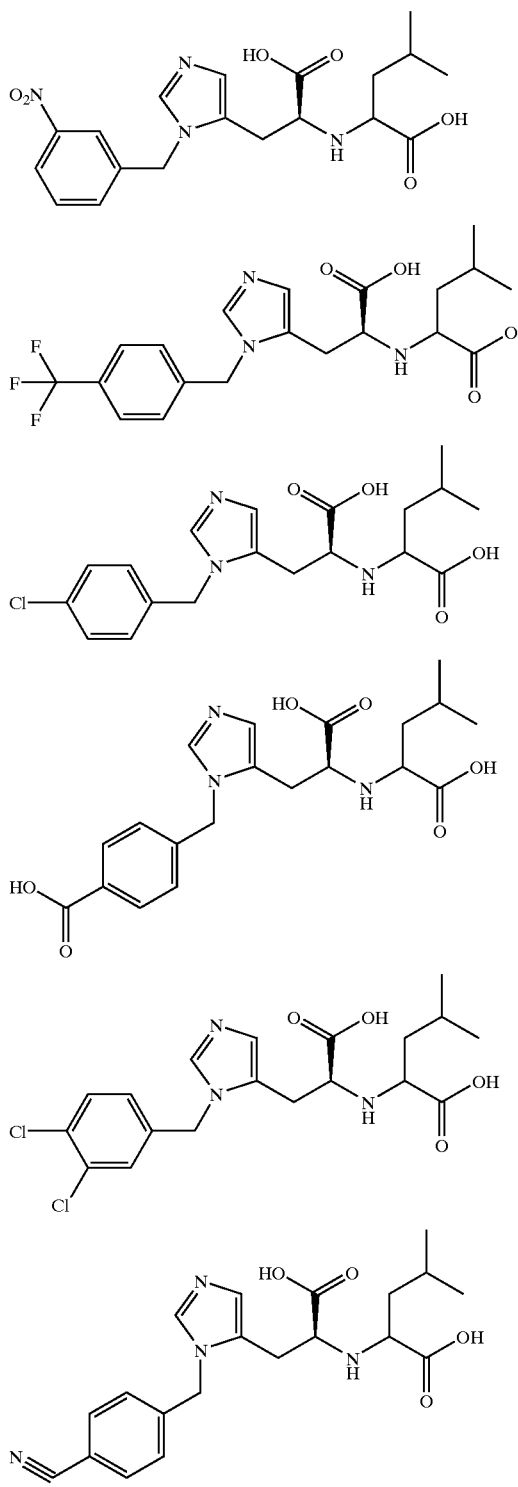
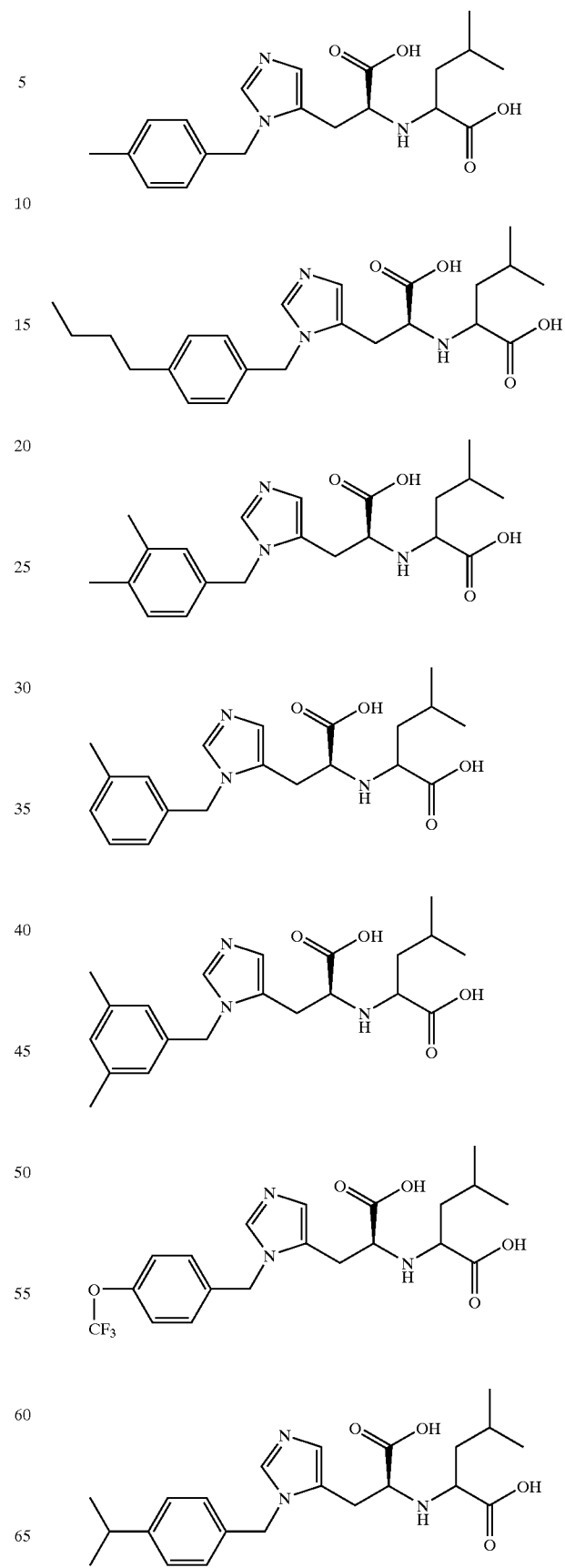

191
-continued
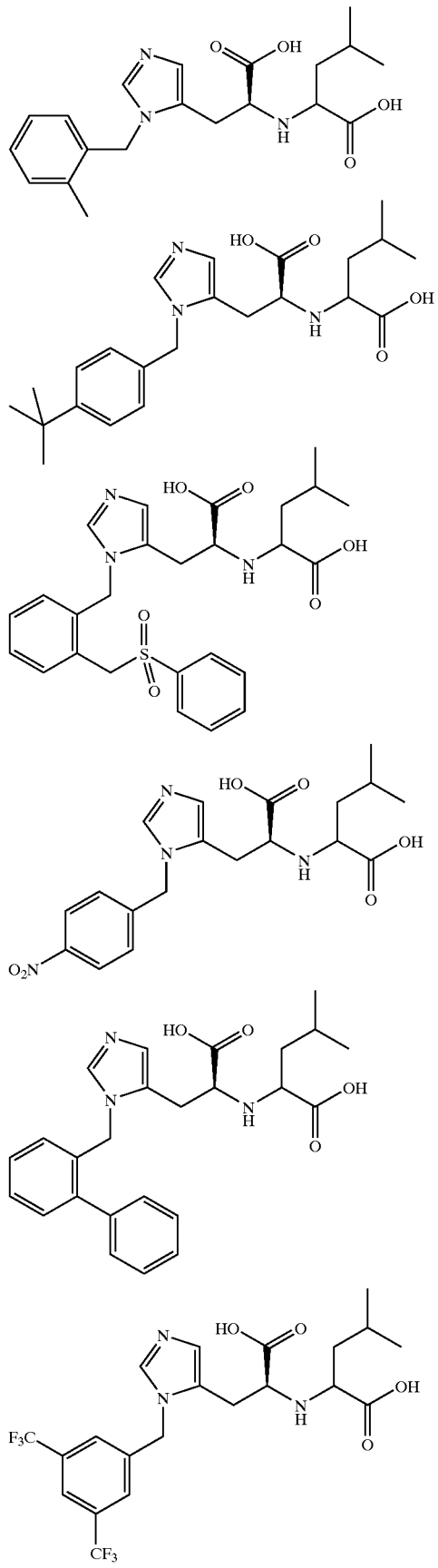
192
-continued
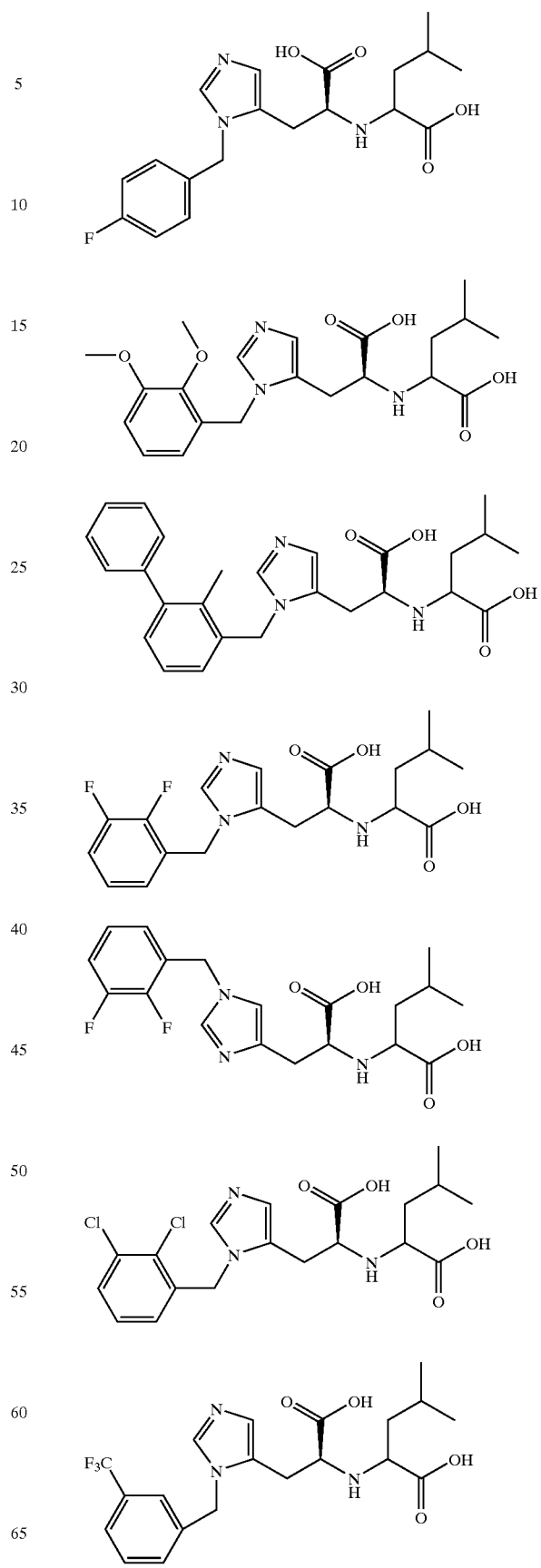

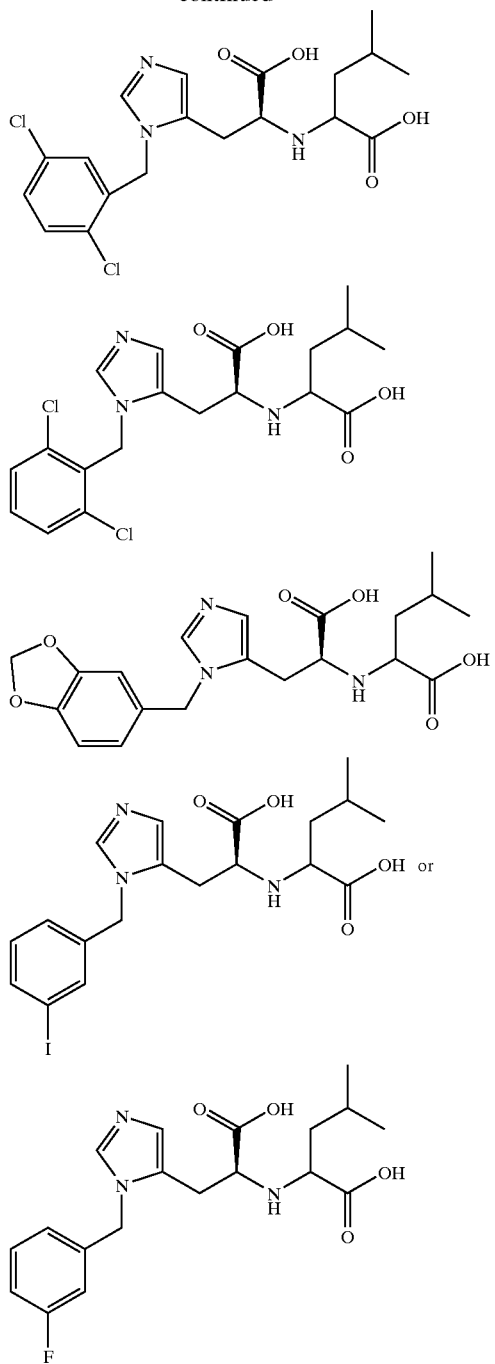
or pharmaceutically acceptable salts thereof.
144. A compound that is:
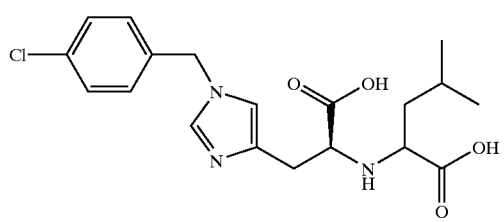
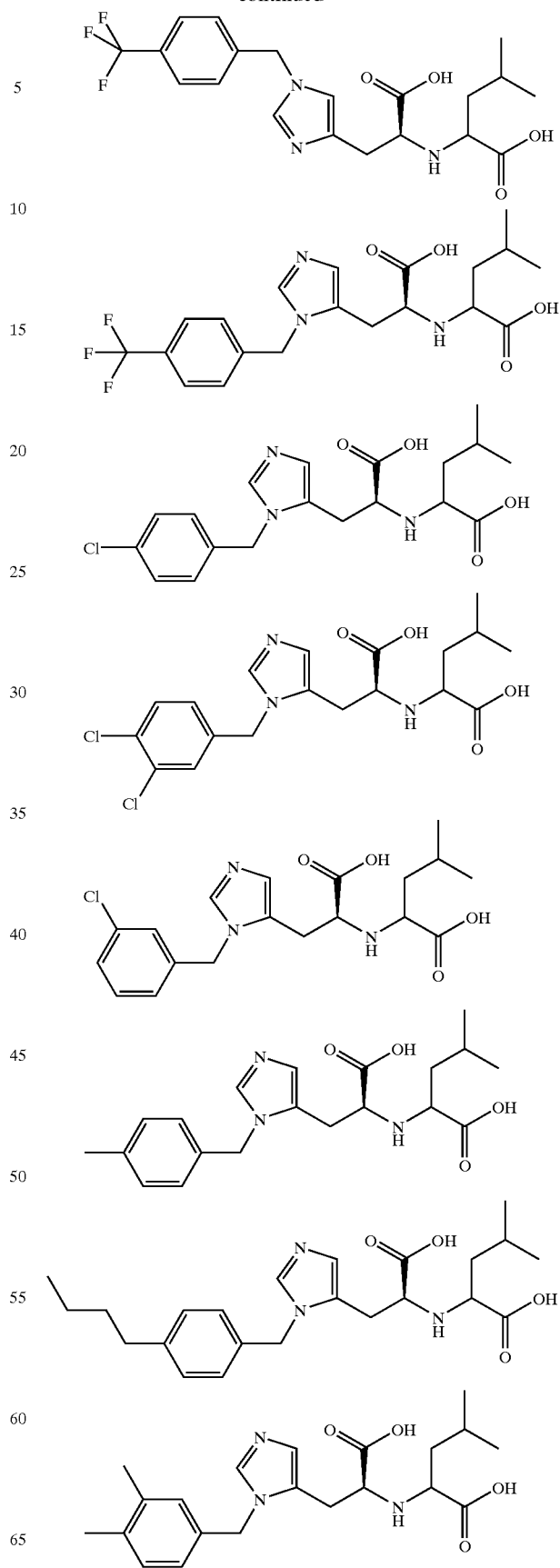

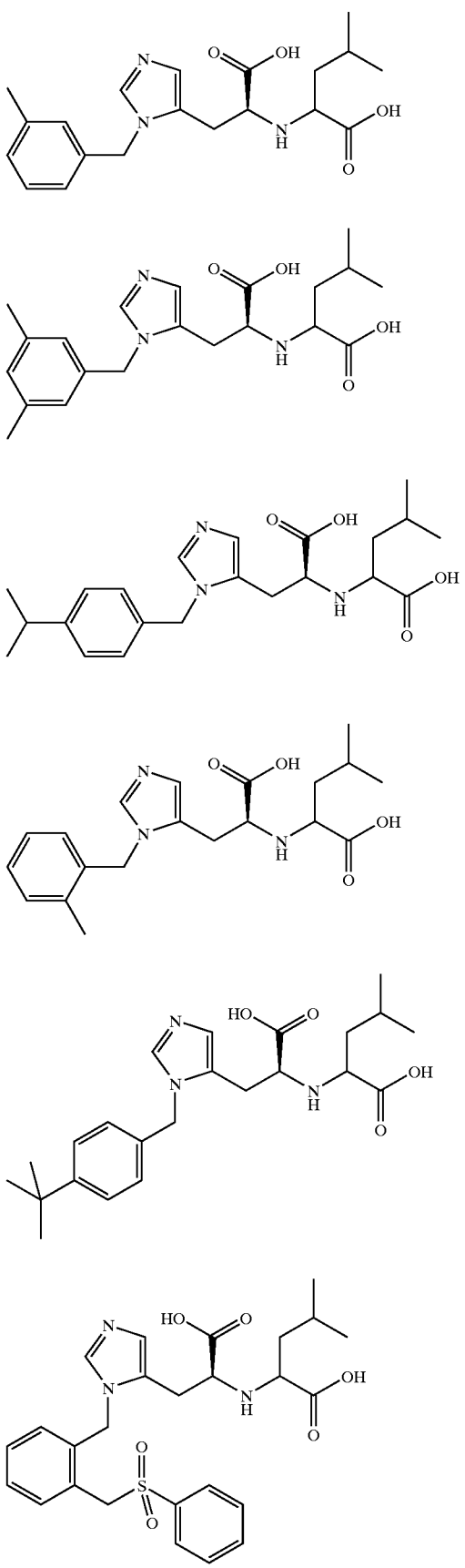
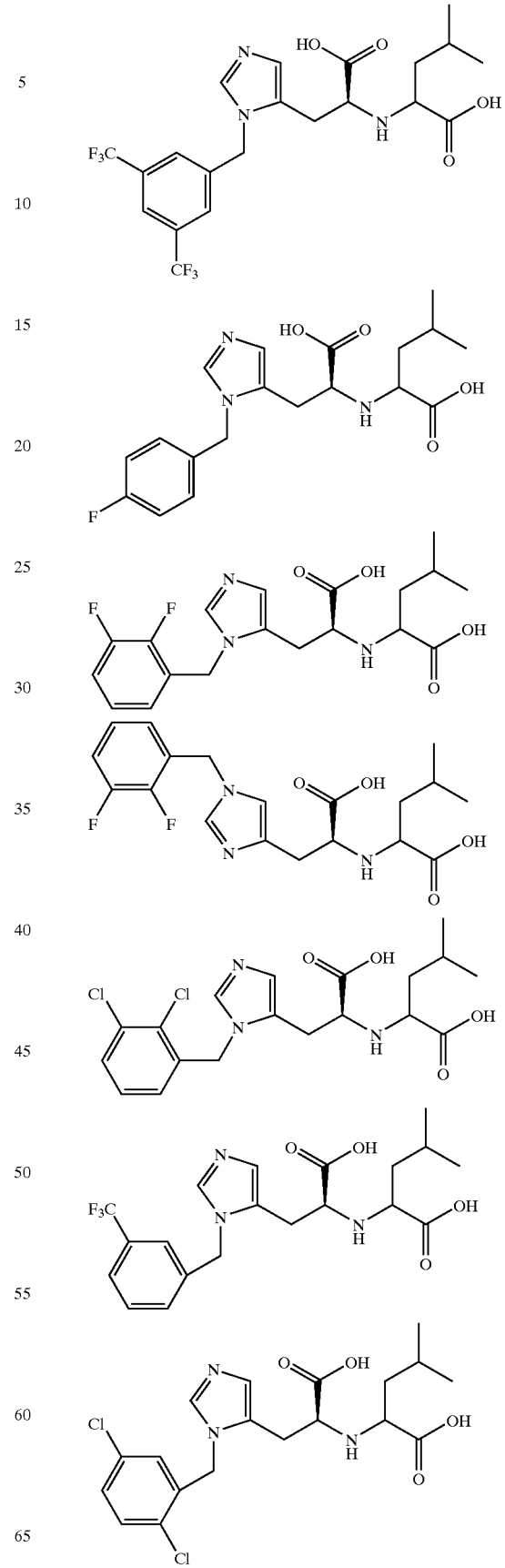

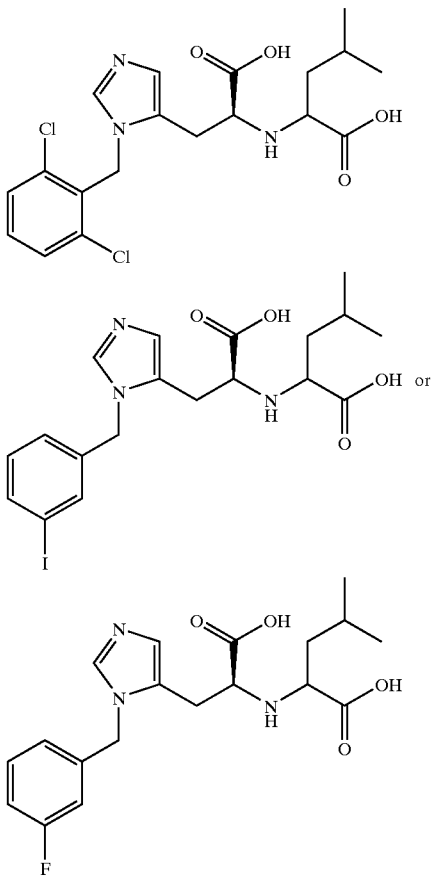
or pharmaceutically acceptable salts thereof.
145. A pharmaceutical composition comprising a pharmaceutically acceptable carrier and an effective amount of a compound that is:
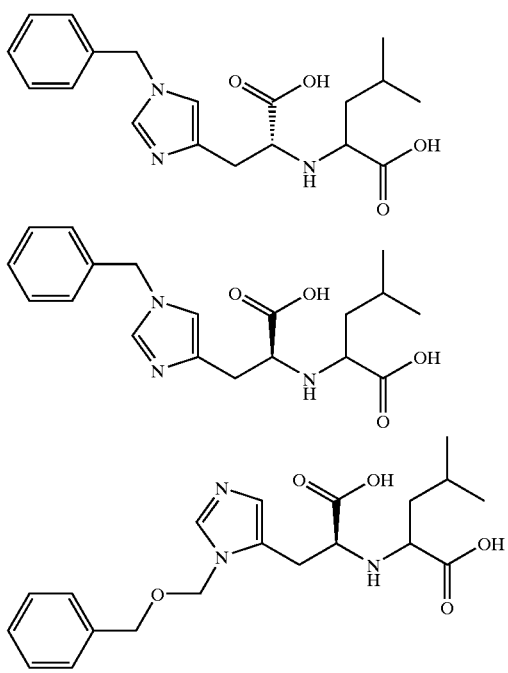
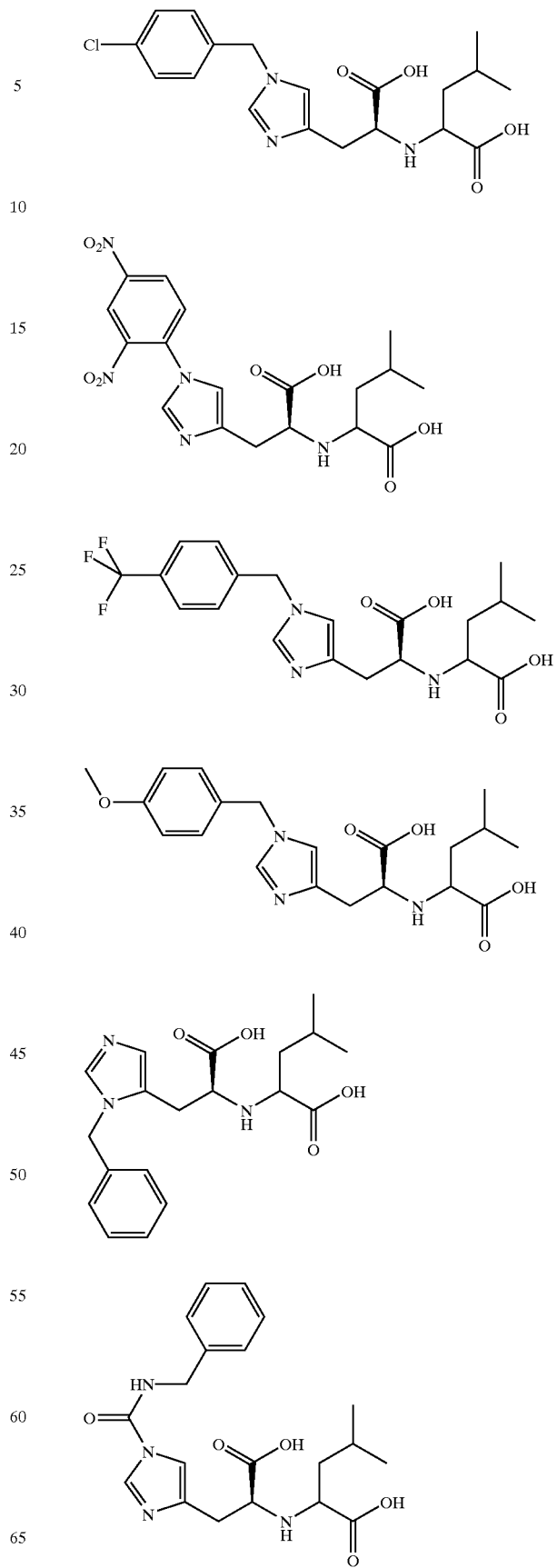

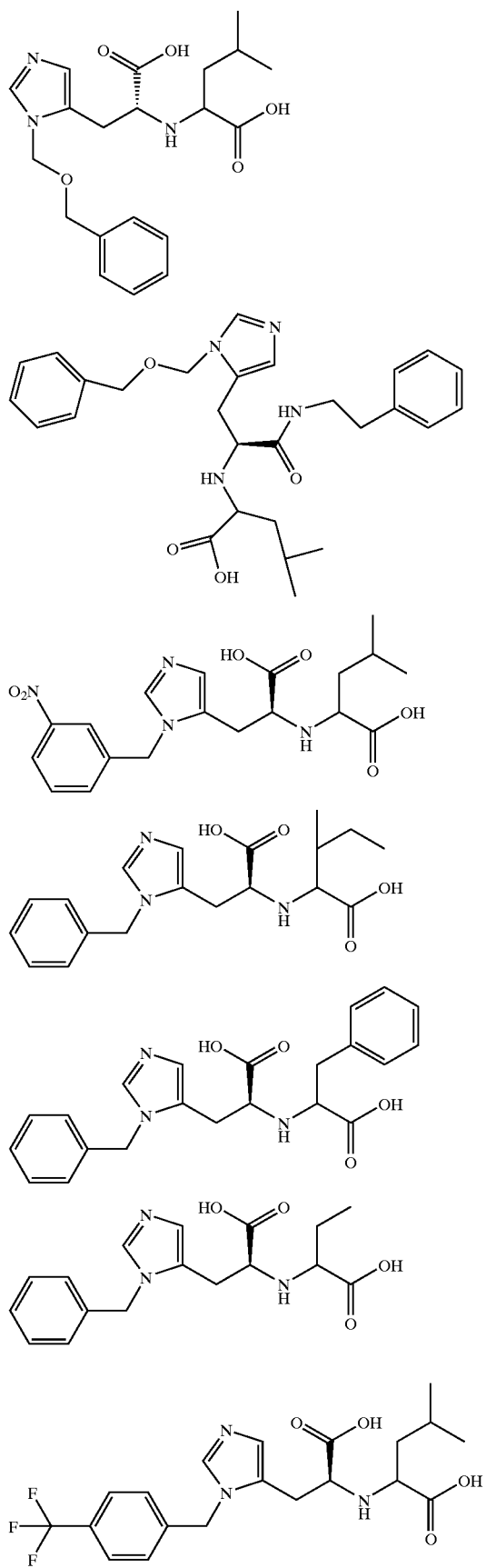
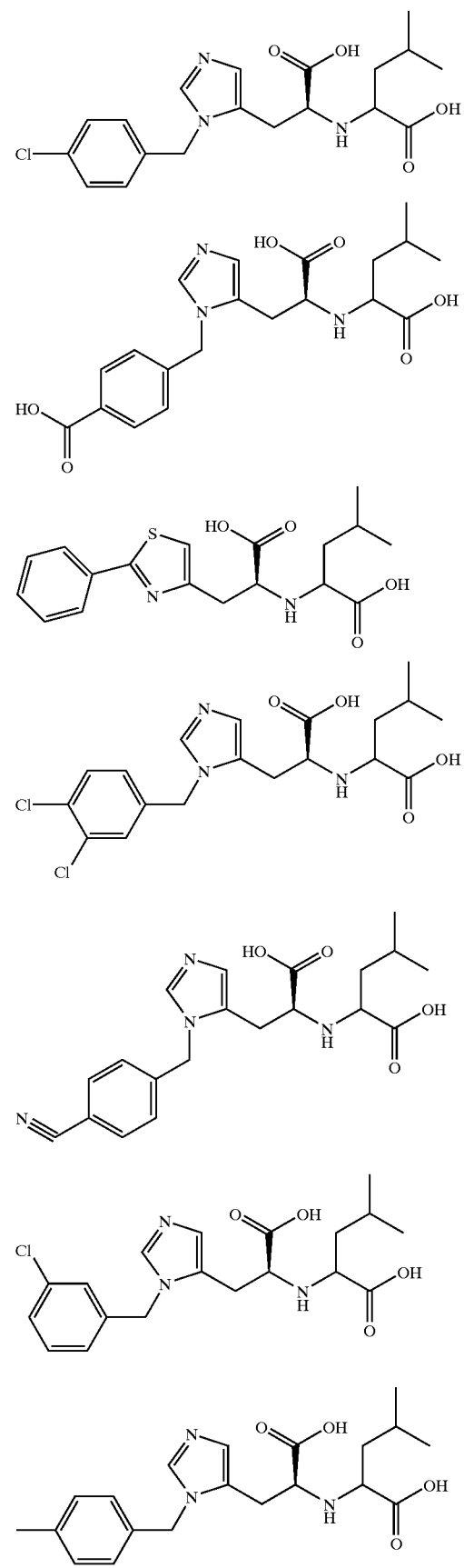

-continued
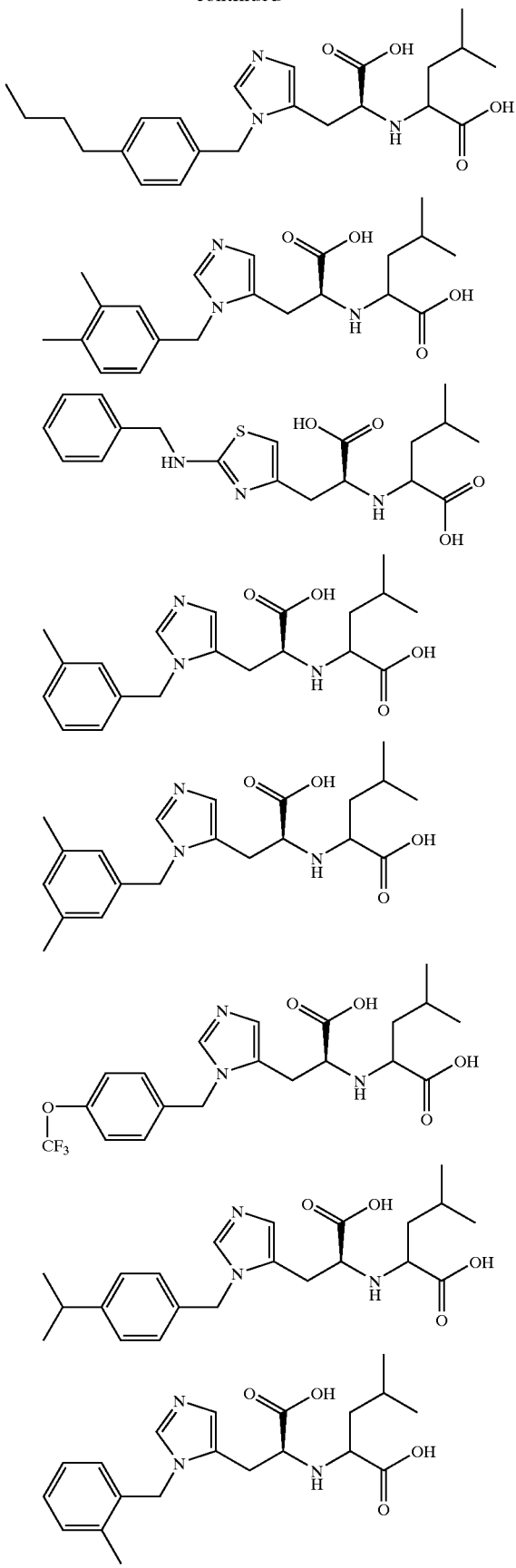
-continued
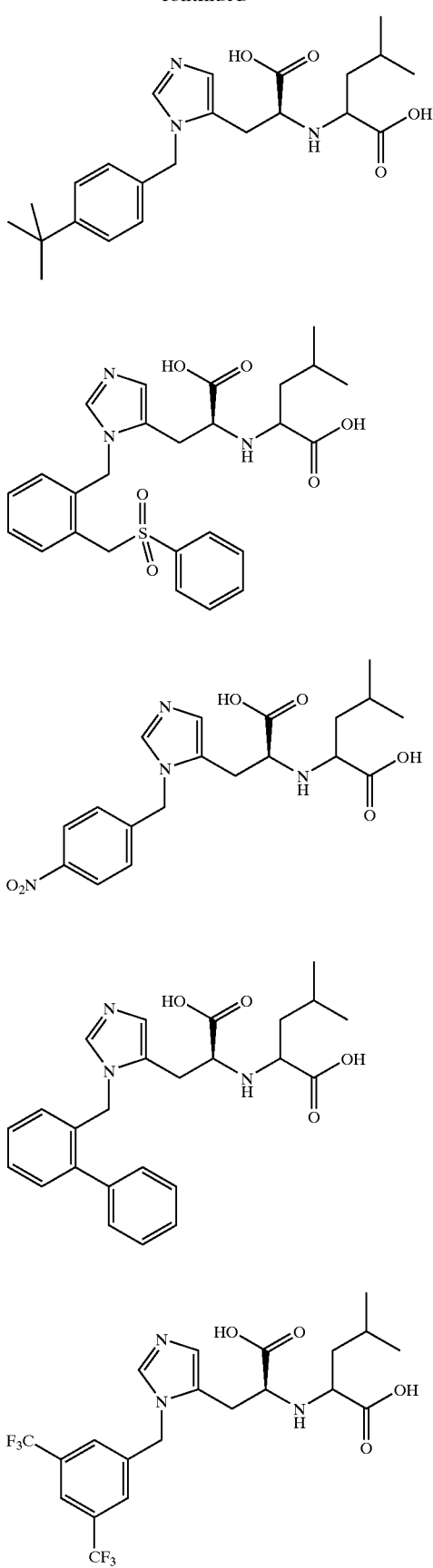

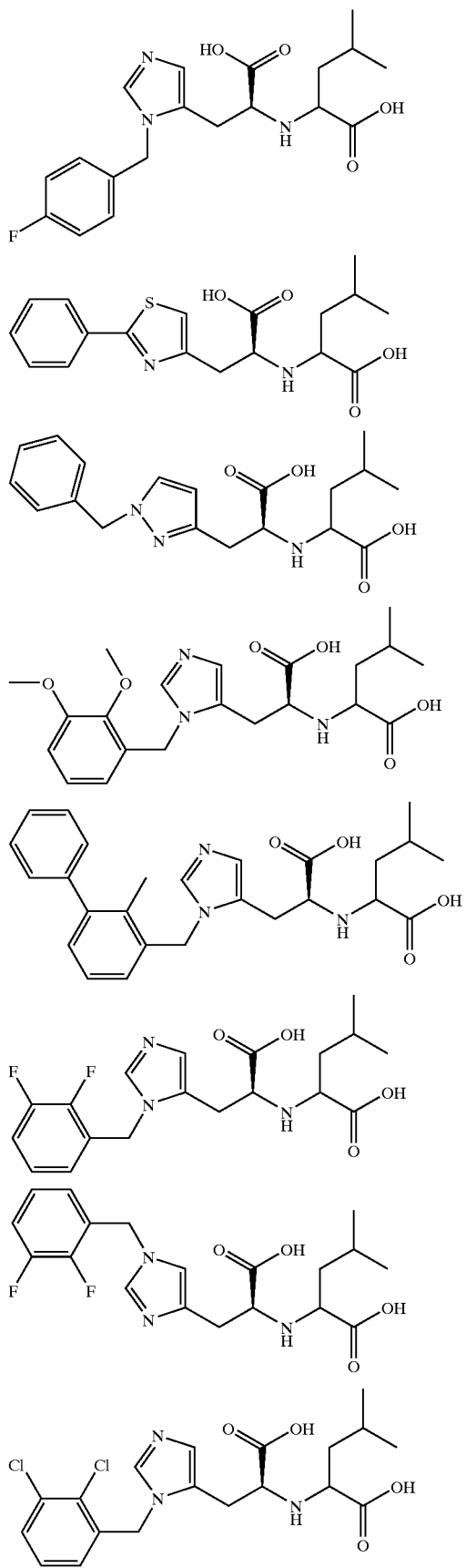
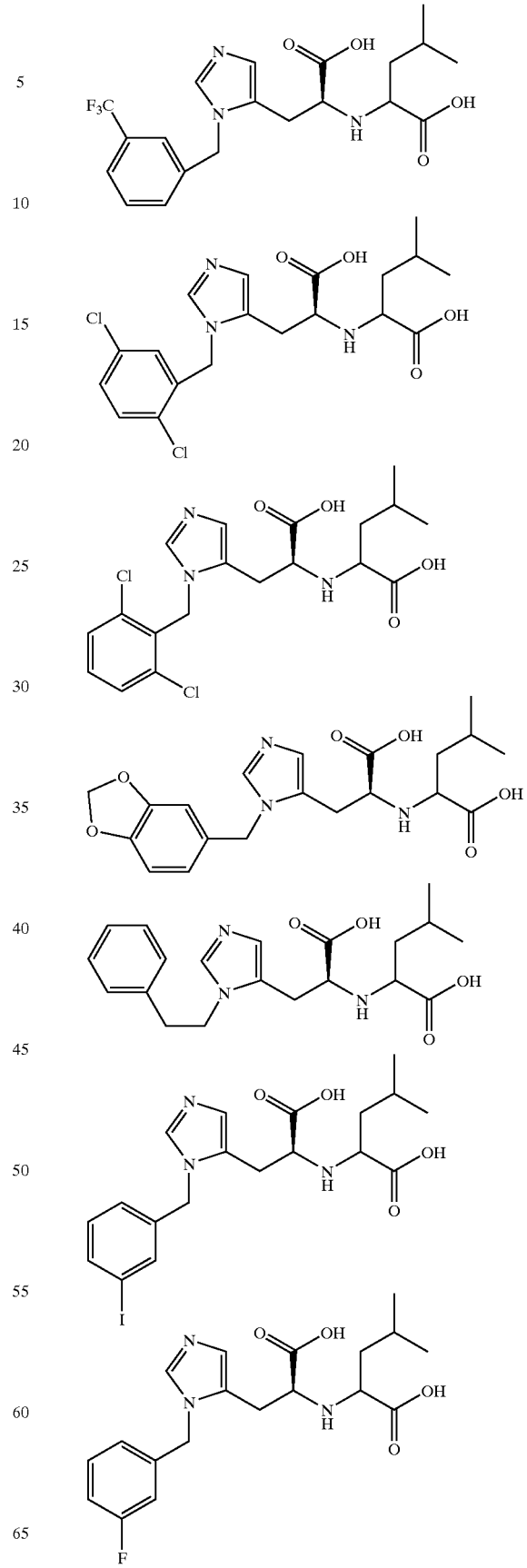

205
-continued
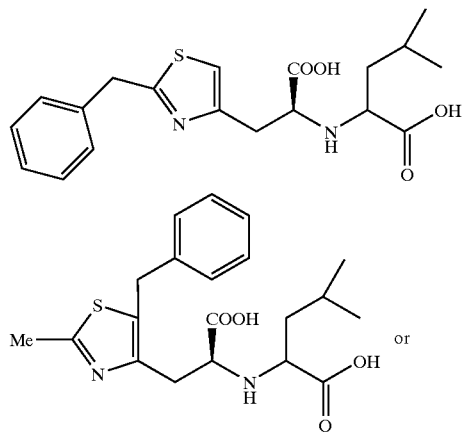
206
-continued
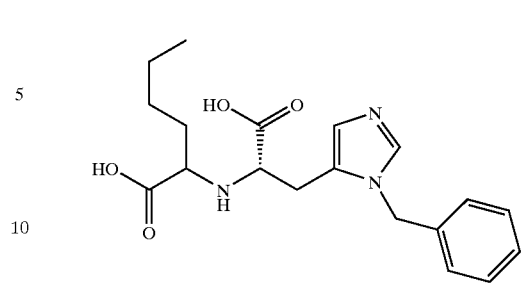
or pharmaceutically acceptable salts thereof.
* * * * *